US010221218B2

(12) United States Patent
Chiu et al.

(10) Patent No.: US 10,221,218 B2
(45) Date of Patent: Mar. 5, 2019

(54) ADENOVIRUS ISOLATED FROM TITI MONKEYS

(71) Applicants: THE REGENTS OF THE UNIVERSITY OF CALIFORNIA, Oakland, CA (US); Jacquelyn Dieter, Davis, CA (US)

(72) Inventors: Charles Chiu, San Francisco, CA (US); Eunice Chen, Palo Alto, CA (US); Nicholas W. Lerche, Davis, CA (US); Karen Lisa Bales, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/996,127

(22) Filed: Jan. 14, 2016

(65) Prior Publication Data

US 2016/0264629 A1 Sep. 15, 2016

Related U.S. Application Data

(63) Continuation-in-part of application No. 13/469,011, filed on May 10, 2012, now Pat. No. 9,267,112.

(60) Provisional application No. 61/484,536, filed on May 10, 2011.

(51) Int. Cl.

| | |
|---|---|
| ***C12N 15/67*** | (2006.01) |
| ***C07K 14/005*** | (2006.01) |
| ***C12Q 1/70*** | (2006.01) |
| ***G01N 33/569*** | (2006.01) |
| ***C12N 7/00*** | (2006.01) |

(52) U.S. Cl.

CPC .............. *C07K 14/005* (2013.01); *C12N 7/00* (2013.01); *C12Q 1/701* (2013.01); *G01N 33/56983* (2013.01); *C12N 2710/10321* (2013.01); *C12N 2710/10322* (2013.01); *C12N 2710/10334* (2013.01); *G01N 2469/20* (2013.01)

(58) Field of Classification Search

CPC ............ A61K 2039/525; A61K 39/235; C12N 2710/10345

See application file for complete search history.

(56) References Cited

U.S. PATENT DOCUMENTS

| | | | |
|---|---|---|---|
| 4,235,877 | A | 11/1980 | Fullerton |
| 4,372,945 | A | 2/1983 | Likhite |
| 4,474,757 | A | 10/1984 | Arnon et al. |
| 4,603,112 | A | 7/1986 | Paoletti et al. |
| 4,676,980 | A | 6/1987 | Segal et al. |
| 4,769,330 | A | 9/1988 | Paoletti et al. |
| 4,777,127 | A | 10/1988 | Suni et al. |
| 5,017,487 | A | 5/1991 | Stunnenberg et al. |
| 5,556,752 | A | 9/1996 | Lockhart et al. |
| 5,578,832 | A | 11/1996 | Trulson et al. |
| 5,593,839 | A | 1/1997 | Hubbell et al. |
| 5,599,695 | A | 2/1997 | Pease et al. |
| 5,631,734 | A | 5/1997 | Stern et al. |
| 7,820,441 | B2 | 10/2010 | Chamberlain et al. |
| 2008/0090281 | A1 | 4/2008 | Wilson et al. |
| 2010/0247490 | A1 | 9/2010 | Roy et al. |

FOREIGN PATENT DOCUMENTS

| | | | |
|---|---|---|---|
| EE | 03089 | B1 | 11/1994 |
| EP | 0345242 | A2 | 12/1989 |
| EP | 0721016 | A2 | 10/1995 |
| EP | 0728520 | A1 | 8/1996 |
| EP | 0785280 | A2 | 7/1997 |
| EP | 0799897 | A1 | 10/1997 |
| GB | 2200651 | | 8/1998 |
| WO | WO 198901973 | | 3/1989 |
| WO | WO 1991/00904 | | 1/1991 |
| WO | WO 199100360 | | 1/1991 |
| WO | WO 1991/02805 | | 3/1991 |
| WO | WO 199200373 | | 1/1992 |
| WO | WO 1993/08829 | | 5/1993 |
| WO | WO 199522058 | | 8/1995 |
| WO | WO 199702357 | | 1/1997 |
| WO | WO 1997/29212 | | 8/1997 |
| WO | WO 2002/27007 | | 4/2002 |
| WO | WO 2003/076592 | | 9/2003 |
| WO | WO 2010/138675 | | 12/2010 |

OTHER PUBLICATIONS

Åkerström, B. et al., "Protein G. A Powerful Tool for Binding and Detection of Monoclonal and Polyclonal Antibodies", *The Journal of Immunology*, vol. 135, pp. 2589-2542 (1985).

Altschul, S. et al., "Basic Local Alignment Search Tool", *J. Mol. Biol.*, vol. 215, pp. 403-410 (1990).

Altschul, S. et al., "Gapped BLAST and PSI-BLAST: a new generation of protein database search programs", *Nucleic Acids Research*, vol. 25, No. 17, pp. 3389-3402 (1997).

Bányai, K. et al., "Molecular detection of novel adenoviruses in fecal specimens of captive monkeys with diarrhea in China", *Veterinary Microbiology*, vol. 142, pp. 416-419 (2010).

Basnight, B. et al., "Characterization of Four New Adenovirus Serotypes Isolated from Chimpanzee Tissue Explants", *Am., J. Epidemiol*, vol. 94, pp. 166-171 (1971).

Batzer, M. et al., "Enhanced evolutionary PCR using oligonucleotides with inosine at the 3'-terminus", *Nucleic Acids Research*, vol. 19, No. 18, p. 5081 (1991).

(Continued)

*Primary Examiner* — Bao Q Li

(74) *Attorney, Agent, or Firm* — Morgan, Lewis & Bockius LLP; Jeffry S. Mann; Louis T. Nguyen

(57) ABSTRACT

Provided is a Titi Monkey Adenovirus (TMAdV) that can infect both human and non-human primates. Further provided are nucleic acid sequences, proteins, expression vectors and host cells, anti-TMAdV antibodies, vaccines, compositions, methods of detecting TMAdV, methods for assaying for anti-TMAdV compounds, and methods for treating or preventing a TMAdV infection.

2 Claims, 34 Drawing Sheets

Specification includes a Sequence Listing.

(56) References Cited

OTHER PUBLICATIONS

Bergelson, J. et al., "Isolation of a Common Receptor for Coxsackie B Viruses and Adenoviruses 2 and 5", Science, vol. 275, pp. 1320-1323 (1997).
Berkner, K., "Development of Adenovirus Vectors for the Expression of Heterologous Genes", *BioTechniques*, vol. 6, pp. 616-627 (1988).
Carrigan, D., "Adenovirus Infections in Immunocompromised Patients", *Am. J. Med.*, vol. 102, pp. 71-74 (1997).
Chen, E. et al., "Cross-Species Transmission of a Novel Adenovirus Associated with a Fulminant Pneumonia Outbreak in a New World Monkey Colony", *PLoS Pathogens*, vol. 7, No. 7, p. e1002155 (2011).
Chiu, C. et al., "Microarray Detection of Human Parainfluenzavirus 4 Infection Associated with Respiratory Failure in a Immunocompetent Adult", *CID*, vol. 43, e71-e76 (2006).
Cohen, J., "Naked DNA Points Way to Vaccines", *Science*, vol. 259, pp. 1691-1692 (1993).
Echavarria, M. et al., "PCR Method for Detection of Adenovirus in Urine of Healthy and Human Immunodeficiency Virus-Infected Individuals", *Journal of Clinical Microbiology*, vol. 36, No. 11, pp. 3323-3326 (1998).
Eisen, M. et al., "Cluster analysis and display of genome-wide expression patterns", Proc. Natl. Acad. Sci. USA, vol. 95, pp. 14863-14868 (1998).
Ersching, J. et al., "Neutralizing antibodies to human and simian adenoviruses in humans and New-World monkeys", *Virology*, vol. 407, pp. 1-6 (2010).
Fisher-Hoch, S.P. et al., "Protection of rhesus monkeys from fatal Lassa fever by vaccination with a recombinant vaccinia virus containing the Lassa virus glycoprotein gene", Proc. Natl., Acad. Sci. USA, vol. 86, pp. 317-321 (1989).
Flexner, C. et al., "Attenuation and immunogenicity in primates of vaccinia virus recombinants expressing human interleukin-2", *Vaccine*, vol. 8, pp. 17-21 (1990).
Fodor, S. et al., "Light-Directed, Spatially Addressable Parallel Chemical Synthesis", *Science*, vol. 251, pp. 767-773 (1991).
Fox, J. et al., "The Seattle Virus Watch", *Am. J. Epidemiol.*, vol. 105, pp. 362-386 (1977).
Frank and Döring, "Simultaneous Multiple Peptide Synthesis Under Continuous Flow Conditions on Cellulose Paper Discs as Segmental Solid Supports", *Tetrahedron*, vol. 44, No. 19, pp. 6031-6040 (1988).
Geysen, H.M. et al., "Strategies for epitope analysis using peptide synthesis", *Journal of Immunological Methods*, vol. 102, pp. 259-274 (1987).
Ghosh, S. et al., "Adenoviral Vectors", *Applied Biochemistry and Biotechnology*, vol. 133, pp. 9-29 (2006).
Greninger, A. et al., "A Metagenomic Analysis of Pandemic Influenza A (2009 H1N1) Infection in Patients from North America", *PLoS ONE*, vol. 5, No. 10, e13381 (2010).
Guzman, R. J. et al., "Efficient and selective adenovirus-mediated gene transfer into vascular neointima", *Circulation*, vol. 88, pp. 2838-2848 (1993).
Guzman, R. J. et al., "Efficient Gene Transfer Into Myocardium by Direct Injection of Adenovirus Vectors", *Circulation Research*, vol. 73, No. 6, pp. 1202-1207 (1993).
Henikoff, S. and Henikoff, J., "Amino acid substitution matrices from protein blocks", *Proc. Natl., Acad. Sci. USA*, vol. 89, pp. 10915-10919 (1992).
Hierholzer, J. et al., "Detection of Adenovirus in Clinical Specimens by Polymerase Chain Reaction and Liquid-Phase Hybridization Quantitated by Time-Resolved Fluorometry", *Journal of Clinical Microbiology*, vol. 31, No. 7, pp. 1886-1891 (1993).
Kajon, A. et al., "Molecular Epidemiology and Brief History of Emerging Adenovirus 14-Associated Respiratory Disease in the United States", JID, vol. 202, pp. 93-103 (2010).
Kass-Eisler, A. et al., "Quantitative determination of adenovirus-mediated gene delivery to rat cardiac myocytes in vitro and in vivo", *Proc. Natl. Acad. Sci. USA*, vol. 90, pp. 11498-11502 (1993).
Kolls, J. et al., "Prolonged and effective blockade of tumor necrosis factor activity through adenovirus-mediated gene transfer", *Proc. Natl. Acad. Sci. USA*, vol. 91, pp. 215-219 (1994).
Kozal, M. et al., "Extensive polymorphisms observed in HIV-1 clade B protease gene using high-density oligonucleotide arrays", *Nature Medicine*, vol. 2, No. 7, pp. 753-759 (1996).
Kronvall, G. et al., "A Surface Component in Group A, C, and G Streptococci with Non-Immune Reactivity for Immunoglobulin G", *The Journal of Immunology*, vol. 111, No. 5, pp. 1401-1406 (1973).
Lee, W. et al., "High-Throughput, Sensitive, and Accurate Multiplex PCR-Microsphere Flow Cytometry System for Large-Scale Comprehansive Detection of Respiratory Viruses", Journal of Clinical Microbiology, vol. 45, No. 8, pp. 2626-2634 (2007).
Lewis, P. et al., "A Community-Based Outreak of Severe Respiratory Illness Caused by Human Adenovirus Serotype 14", *JID*, vol. 199, pp. 1427-1434 (2009).
Lole, K. et al., "Full-Length Human Immunodeficiency Virus Type 1 Genomes from Subtype C-Infected Seroconverters in India, with Evidence of Intersubtype Recombination", *Journal of Virology*, vol. 73, No. 1, pp. 152-160 (1999).
Marks, J. et al., "By-Passing Immunization: Building High Affinity Human Antibodies by Chain Shuffling", *Biotechnology*, vol. 10, pp. 779-783 (1992).
McCafferty, J. et al., "Phage antibodies: filamentous phage displaying antibody variable domains", *Nature*, vol. 348, pp. 552-554 (1990).
Merrifield, R.B., "Solid Phase Peptide Synthesis I. The Synthesis of a Tetrapeptide", *J. Am. Chem. Soc.*, vol. 85, pp. 2149-2154 (1963).
Moss and Flexner, "Vaccinia Virus Expression Vectors", *Ann. N.Y. Acad. Sci.*, vol. 569, pp. 86-103 (1989).
Mwenda J. M. et al., "Serological Detection of Adenoviruses in Non-Human Primates Maintained in a Colony in Kenya", *East African Medical Journal*, vol. 82, pp. 371-375 (2005).
NCBI, Genbank accession No. HQ913600.1, Titi monkey adenovirus ECC-2011, complete genome, (2012).
NCBI, Genbank accession No. AF394196.1, "Simian adenovirus 25, complete genome", (2001).
Needleman, S. et al., "A General Method Applicable to the Search for Similarities in the Amino Acid Sequence of Two Proteins", J. Mol. Biol., vol. 48, pp. 443-453 (1970).
Ohtsuka, E. et al., "An Alternative Approach to Deoxyoligonucleotides as Hybridization Probes by Insertion of Deoxyinosine at Ambiguous Codon Positions", *The Journal of Biological Chemistry*, vol. 260, No. 5, pp. 2605-2608 (1985).
Pearson and Lipman, "Improved tools for biological sequence comparison", *Proc. Natl. Acad. Sci. USA*, vol. 85, pp. 2444-2448 (1988).
Renaut, L. et al., "Abolition of hCAR-dependent cell tropism using fiber knobs of *Atadenovirus* serotypes", *Virology*, vol. 321, pp. 189-204 (2004).
Rosenfeld, M. et al., "Adenovirus-Mediated Transfer of a Recombinant $\alpha$1-Antitrypsin Gene to the Lung Epithelium in Vivo", Science, vol. 252, pp. 431-434 (1991).
Rossolini, G. et al., "Use of deoxyinosine-containing primers vs degenerate primers for polymerase chain reaction based on ambiguous sequence information", *Molecular and Cellular Probes*, vol. 8, pp. 91-98 (1994).
Roy, S. et al., "Isolation and Characterization of Adenoviruses Persistently Shed from the Gastrointestinal Tract of Non-Human Primates", *PLoS Pathogens*, vol. 5, No. 7, e1000503 (2009).
Sheldon, E. et al., "Matrix DNA Hybridization", Clinical Chemistry, vol. 39, No. 4, pp. 718-719 (1993).
Smith and Waterman, "Comparison of Biosequences", *Advances in Applied Mathematics*, vol. 2, pp. 482-489 (1981).
Sorber, K. et al., "The Long March: A Sample Preparation Technique that Enhances Contig Length and Covderage by High-Throughput Short-Read Sequencing", *PLoS ONE*, vol. 3, No. 10, e3495 (2008).

(56) References Cited

OTHER PUBLICATIONS

Suresh, M.R. et al., "Bispecific Monoclonal Antibodies from Hybrid Hybridomas", *Methods in Enzymology*, vol. 121, pp. 210-228 (1986).
Tong, S. et al., "Short Report: Identification of Adenoviruses in Fecal Specimens from Wild Chimpanzees (*Pan trogylodytes schweinfurthii*) in Western Tanzania", *Am. J. Trop. Med. Hyg.*, vol. 82, No. 5, pp. 967-970 (2010).
Traunecker, A. et al., "Bispecific single chain molecules (Janusisns) target cytotoxic lymphocytes on HIV infected cells", *The EMBO Journal*, vol. 10, No. 12, pp. 3655-3659 (1991).
Ulmer, J. et al., "Heterologous Protection Against Influenza by Injection of DNA Encoding a Viral Protein", *Science*, vol. 259, pp. 1745-1749 (1993).
Urisman, A. et al., "E-Predict: a computational strategy for species identification based on observed DNA microarray hybridization patterns", *Genome Biology*, vol. 6, R78 (2005).
Walsh, M. et al., "Evidence of Molecular Evolution Driven by Recombination Events Influencing Tropism in a Novel Human Adenovirus that Causes Epidemic Keratoconjunctivitis", *PLoS ONE*, vol. 4, No. 6, e5636 (2009).
Wang, D. et al., "Microarray-based detection and genotyping of viral pathogens", *PNAS*, vol. 99, No. 24, pp. 15687-15692 (2002).
Welch, T., "A Technique for High-Performance Data Compression", *Computer*, pp. 8-19 (1984).
Wevers, D. et al., "A novel adenovirus of Western lowland gorillas (*Gorilla gorilla gorilla*)", *Virology Journal*, vol. 7, No. 303, pp. 1-8 (2010).
Wickham, T. et al., "Integrins $\alpha_v\beta_3$ and $\alpha_v\beta_5$ Promote Adenovirus Internalization but Not Virus Attachment", *Cell*, vol. 73, pp. 309-319 (1993).
Woods, L.W. et al., "Systemic Adenovirus Infection Associated with High Mortality in Mule Deer (*Odocoileus hemionus*) in California", Vet Pathol., vol. 33, pp. 125-132 (1996).
Wu, Z. et al., "Single Amino Acid Changes Can Influence Titer, Heparin Binding, and Tissue Tropism in Different Adeno-Associated Virus Serotypes", *Journal of Virology*, vol. 80, No. 22, p. 11393-11397 (2006).
Xiang, Z. et al., "Chimpanzee Adenovirus Antibodies in Humans, Sub-Saharan Africa", *Emerging Infectious Diseases*, vol. 12, No. 10, pp. 1596-1599 (2006).
Xu, W. et al., "Species-Specific Identification of Human Adenoviruses by a Multiplex PCR Assay", *Journal of Clinical Microbiology*, vol. 38, No. 11, pp. 4114-4120 (2000).

Figure 9

| FEATURES | Location/Qualifiers |
|---|---|
| CDS | order(complement(9059..11095),complement(14260..14268))(SEQ ID NO 2) |
| CDS | order(complement(6203..6215),complement(4564..5924))(SEQ ID NO 3) |
| CDS | 2042..3643 (SEQ ID NO 4) |
| CDS | order(complement(33500..33904),complement(34657..34794)) (SEQ ID NO 5) |
| repeat_region | 1..145 (SEQ ID NO 6) |
| repeat_region | complement(36698..36842)(SEQ ID NO 7) |
| CDS | order(complement(14260..14268),complement(5688..9212))(SEQ ID NO 8) |
| CDS | 19374..22163 (SEQ ID NO 9) |
| CDS | 24447..26891 (SEQ ID NO 10) |
| CDS | 12371..14200 (SEQ ID NO 11) |
| CDS | 14357..15997 (SEQ ID NO 12) |
| CDS | complement(22878..24410) (SEQ ID NO 13) |
| CDS | 31955..33472 (SEQ ID NO 14) |
| CDS | 11155..12417 (SEQ ID NO 15) |
| CDS | 16703..17893 (SEQ ID NO 16) |
| CDS | 29786..30727 (SEQ ID NO 17) |
| CDS | 18311..19195 (SEQ ID NO 18) |
| CDS | complement(33913..34794) (SEQ ID NO 19) |
| CDS | 3764..4513 (SEQ ID NO 20) |
| CDS | 28468..29178 (SEQ ID NO 21) |
| CDS | 27509..28192 (SEQ ID NO 22) |
| CDS | 1677..2333 (SEQ ID NO 23) |
| CDS | 22178..22792 (SEQ ID NO 24) |
| CDS | 16038..16631 (SEQ ID NO 25) |
| CDS | 29195..29779 (SEQ ID NO 26) |

Figure 9 (continued)

CDS 26593..27162 (SEQ ID NO 27)

CDS complement(34697..35149) (SEQ ID NO 28)

CDS 31335..31730 (SEQ ID NO 29)

CDS complement(35561..35953) (SEQ ID NO 30)

CDS 31004..31354 (SEQ ID NO 31)

CDS 28185..28529 (SEQ ID NO 32)

CDS complement(35163..35471) (SEQ ID NO 33)

CDS complement(35975..36277) (SEQ ID NO 34)

CDS 30720..31007 (SEQ ID NO 35)

CDS 17933..18178 (SEQ ID NO 36)

CDS complement(31753..31938) (SEQ ID NO 37)

ORIGIN (SEQ ID NO 1)

1 gcccatcatc aataatatac ctcaaaaacg tccaaattta catccggttg tggtgaaaaa 61 cgcggagtgt ggggattggg ggttgagggg tgtggggcgg gacttccggc gtgtttggcg 121 cggggcggcc atgttggtag ttttccgaga tttttccgtt ttgaggggtt ttggactaca 181 aatgaagcaa gatggcggct gggaggagcc aaaatggact ttgcccagag aaaatgacgt 241 catccgggga ttttccacgg attgggcggc agatttgcaa gtttttagac aaaattttta 301 cgcggaagtg aaacccgaaa attcagaagt tgacgtgaca ggtgtggttt tattgccggg 361 ccatttgacc tttgaccgcc acgtcgacag cgggccgggg aatttttttgt gctgacattt 421 ccgggtttcg gtgtcaaagt ccccgctggg caccgcggag tcagctgacc cgctgggtat 481 ttaatgccga gcgctcccgt caagaggcca ctcttgagtg caccgcgaga agagttttct 541 ccgagctccc gtctgaaccg tgggaaaaaa tgaagacttg gcagtgtcag tctctggccg 601 acctggagct ggtgcaggag atcctggacg agatgggaga aggtaaccac ggtcactttg 661 tgcccgagga cggtggggac ccgggggaca gcggcttcgt tccggaaccg ctttcgcttc 721 acgatctctt cgacgtgccg acggatcctc tgacccagga gcatgccgag gcggtagatc 781 tcttgttccc ggacccggtc gagcccgata gcacccagga ggatgttgac cgcccgctcc

Figure 9 (continued)

841 gaaccccttc tccgcctcag ctttctcccg tgaatcttgt gtgtagacga gaacaagaac 901 tggaagagct cggggccgag atagatctca cctgtcacga gaagatgttt acagacagcg 961 aggacgaggg agaaggtgct cctcaaaatg gcggttccgg tgagcgagat ggcttccgtc 1021 tggattgtcc tgagcagccc ggtcagggtt gtttgtcttg tcacgtccat cgctgtacca 1081 tgggtgatcc caccttgatg tgttcgctgt gttacatgcg cttgaacagc cactgtatct 1141 acagtaagtg tttctcgctt ggggatgtgt gaagtgtctg gagtagggaa aaagctaggg 1201 gaattttcca ttcgagtgtg tctcattatt cttgttctta atgtgacagg tcctgtctct 1261 gagccagaag aagaggaggg agatgaaagt tcccgggaac ggccgcggcc ttccacgagt 1321 gctcaggggg tgactcagcg accacagaaa cgccaacatg cagatgtcct taccgacccc 1381 ccccagctgg gggcggtgtg cgccttgctg ggccccgcagg aggaaccttt ggacttgagc 1441 tgcaagcgtt cccgcccaga gtcataaaac cacagacact tgagattgtt tgttgaactc 1501 agggaggggt ggccgggggtg agtcagtgtg tgcaataaac gacttgttgg aactggactc 1561 tgtcccggcg atgtttgttc agggctcaag tgggtgcggt ggggaggtat aaacatgggg 1621 cggccgggcg ggttgattca gagcgagagc ggcagccggg ctgagctttt ctctcaatgg 1681 atctcttgaa gttcctggaa gactttgaga attgcagaca agttttgcag caggcgtcca 1741 agaggactgg gggttggagc cgctggctgc ttggcaatca gctggttcgc acggtcgctc 1801 aggtcaagac agactatagc gagcatttcg agcagctttt gcaggagcag aaccgacttc 1861 tgctgaacaa cttggaactc ggtcacacca gggcactgaa cggtgtgctg agggaactgg 1921 actttgagaa tacgggacgg gtggtagctg gtcttgcttt cctcgcgtac ctgctcgatc 1981 ggtgggacga gaacagcgtc ctcagcccgg gctaccgcct cgattgcttg gccctcgcga 2041 tatggaagca cacgctgagg gaggggatcc tgagaggggt gatgcagggg ccccgggcgc 2101 gggtgaaccg ggagatcagg cgggaggtgg aggagcggct gacgcaggtg cagcgggagt 2161 tggaagagag ggagagggag aggcagcagc gggagaggga gcagcagcag caggaggggg 2221 aaatgactac gagcatatgg aggccttcca tggaggcgga gtggccgccg cgggcgggga 2281 tggaccccccc gctggaggag cagtgggagg cggaccacga cccggaggca taattcagca 2341 ggtggctagg ttgtttcccg agctggccgg gcagttgcga gctcccttgc atcggcccgt

Figure 9 (continued)

2401 gcctcgaccc ccaccgagga atgtggatga gcggcggggc atagtcagac cctgggatga 2461 ggccaatccc cagccagccg atgagcaagc gggcccctcg gaccgcacgc gatcttggat 2521 gatgagacgc cgtctggaga acattacttg gcaagaagtc tgggatgact ttttgagggg 2581 tgacatgttt ctgagggata gatacacgtt tgagcagatc cgcacgcact gggtggaccc 2641 ccacgaggat ctgggcctgg cgatcgctac ccattgcaag gtggctttgc atccagacag 2701 gacctatcgt gtgagggaca aaatatttat ccagaactgt tgctatgtca ttgggaacgg 2761 ggccacgatt atggtggaga cgagcgagcg ggtggctttc cagttgggaa tgcaacagat 2821 gagcccatcc atcacgggga tgtttggatg tacttttgta aactgtcgct tcagttgcga 2881 ccctaacgtg ttccgaggaa tttgcatcgc cgcgaacacg tcatttctgg tccacggttg 2941 tcatttcttt ggtttcccgg gagattgtat cgtggccaac gtgggtggtc gggtgcgggg 3001 cacgaccttc acttcttgct ttaaggggat ctataatccc gggcgccatg ctctgtcggt 3061 gagcaagtgc atctttgaca aatgtatgat agccatcagc accctgggct tttccaagat 3121 cagacacaat gtggccaccg agtgtttgtg ctttttactg tgccggggct tgggtcgcat 3181 ccagggcaac acggtgcacg ggccttacct gagctcccac cggatggtga cctgcgggga 3241 cgggaccatc cagaccctgc gtaccatcca catcgtggcc caccgcgccc gcacctggcc 3301 cgtgtttgag cataacgtgc tgatgcgcac cagcatgtac ctgggcaacc ggcggggcat 3361 ctttatgccg cgccagagtc aggccttcca caccaacctg gtgctggacc agcatgcctc 3421 gacccaggtg tccatcagcg ggctgtatga catgagcctg cagatatatc ggacgctgcg 3481 cgtggacgag acccgcagtc ggctgatgca ttgcgagtgc ggcgagtctc acctggtgaa 3541 tggacacgtt ttgggaatct gtacggacga catgcgagtg gatccgctcc aatactcggc 3601 ggctcggacc gagtactctt cttcggagga tgaagcggac tgagtaagga agggttaagc 3661 cctgtggggt gggcggggtc tggtcggtgg cgggaagctg gcagggggcg tggtgggaaa 3721 aagagggggt tggagggcgt gggcggttat tattgccgcg gccatggcta gcaacgggag 3781 ctccacctcc tctggagtca gttttgacgg ggccgtgtac agcccatttc tgacgtgtcg 3841 cctgccccact tgggcgggag tccgtcagaa tgtcatcggg tccaccatcg atgggagccc 3901 ggtgcttcct actaacgcat cttccatgcg ttatgagaca gttagcgcga cgggcggcca

Figure 9 (continued)

3961 ggcaactctg cctatttcta gcttcgggac tcgtgttcta cctgcagatc ctgcagcacg 4021 cttctcgacg atccagaccc ccgcggcagc ctacgcggcg gcagcggcgg ctcgcaacgc 4081 agacttcgaa gaacgcatcg tcgcgggact gacggatctg gcggagaaga ttaacctgct 4141 gaacgtgcgc caggagatgg acgagcgcgc cttggacacc gtgggagccg acatcgtgca 4201 gctgaagcag ggcttggaat tcttcgcgca gcgtgtggag gccctgaccg ggctgtgac 4261 tcagctccag gaacaggtcc aacagctgca agaggccgcc agcgccgcgg ctgtcgtcat 4321 tcccgccact cctgcttctc cccagcctgt ggttccacca gcagctgctg ccgaggttgt 4381 gccgctgccc gtcacccccc ctgattcccc gcatgcagcc gcccccaccg ctccacagcc 4441 tgccgagacc cccgtggctg cacccctcac ctctcccgct tcccccgccc ccgctctcaa 4501 ccctgctgtg taatcaataa agaggcacga gatgcttttt gaatctgaat cacgtgttgg 4561 tttttattgc tgttgggggg agggtagggc tttgcgggcg tggtaggctc ggacccagcg 4621 gttgcggtcg gtgagggtgc gatggatctt ttccaggact cggtagagat gggtctgcac 4681 gttgaggtac atgggcatga ggccttcgcg gggatgcagg tagagccatt ggagggcctc 4741 gtgctcgggg gtggtgttgt agatgatcca gtcgtactgg gaggtctggg cgtggtggga 4801 gaagatgtct ttgagaagca tgctgatggc cacggggagc cccttggtgt aggtgttgat 4861 gaagcgggag agctgggagg gatgcatgcg gggggctgatg agatgcatct tggcctggat 4921 cttgagattg gcgatgttgc cgcccaggtc tcgacggggg ttcatgttgt gcaggacgac 4981 gaggacggtg tagccggtgc acttggggaa cttgtcatgc aacttggaag ggaaggcgtg 5041 gaagaatttg gcgacgcctt tgtgaccgcc gaggttctcc atgcattcgt ccatgatgat 5101 ggcgatgggt ccccgggcgg cggcgcgggc gaaggcgttg cgggggtcgg tgacgtcata 5161 gttgtggtct tgggtgagct cgtcgtagga cattttgatg aatttggggg tgagggtccc 5221 cgattggggg atgagggtgc cttcgggccc gggggcgtag ttgccttcga agatttgcat 5281 ctcccaggct ttgatctcgg aggggggat catgtcgacc tggggggcga tgaagaagac 5341 ggtctcgggg gcgggctgga tgagctgggt ggacatgagg ttgcggagga gctgtgactt 5401 gccgcagccg gtgggaccgt agatgacccc gatgacgggt tgcatgttgt aattgagcga 5461 gcggcaggtg ccgtccgcgg ggttgaggta gggcatgacc gagttgagca tgtctcgcat

Figure 9 (continued)

5521 gatgaggttt tcttggacga gatcctggag cagcttggaa ccgccgaggg agaggagttc 5581 ttggaaggac tggaagttct tgagtggttt caggccgtcg gccagcgaca tcttggcgag 5641 tgagtcagcg agggtttggg tttttccca gatctcgcgg acgtgttcta gggcatctcg 5701 atccagcagg tttcttggtt tcttgggttg ggatggctgt tggagtaggg ccggagccga 5761 tgcatctccc cgggggtgag cggggccagg gtccggtctt tccagggtct gagggtcctc 5821 cggagggtgg tttcggtgac ggtgaagggg tgggcttgag cttgcacgct ggcgagcgag 5881 cgcttgaggg tgaggcgact ggtctcgtag cgggcgtttc cgccttggta ttcctcgaga 5941 taacaattga gcaagagttg gtaggagagt tctgaggcgg ggtgtccctt ggctcggagc 6001 ttgcctttgc cctcgtgacc gcactggggg cagcggaggg atttgagggc gtagagtttg 6061 ggggcgagga agacggactc tgggctgtag gcgtcggcgc cgcacttgct acactgggtc 6121 tcgcattcga cgagccaggt gagctgggga tgctgggggt caaagactag gcctccgcca 6181 tttttcttga tgcgatgctt acctcgggtt tccatgagtc gatggccgcg ttcggtgacg 6241 aagagggagt cggtgtctcc gtagacagat ttcaggggtc gcaggtggag ggggtgccg 6301 cggtcctcgt cgtagaggaa gccggcccac tcggagacga aggctctggt ccaggcgagg 6361 acgaagctgg caatgtgcga ggggtagcgt tcgttctcga tcaaggggtc gttcttttcc 6421 agggtgtgga gacagagcgc gtcctcgtcg cagtccagga aggtgattgg cttgtaagtg 6481 taggtcacgt gatctgggtc cccgggggtc ggctgcgggg gggtataaaa gggggcgtgt 6541 tctgggggt cctcattgtc ctcctcggga tcgctaccgc tgccggcgac gaccgtgggc 6601 tcttgcagcg ccagctgtcc aggtaagaat tctgccgccc aggcgtccat gtattcagaa 6661 ctgaggttgt cagtttcaat gaaggaggag gatttgatgg aatagtgccc cgaggccacg 6721 cccttgacga gggcccctc catctggtca gaaaacaccg tctttttatt gtccagcttg 6781 gtggcgaagg agccatagag ggcgttggag agcaatttgg cgatggagcg gagcgtttgg 6841 ttttgtcgc gatcggcgcg ttccttggcg gcgatgttga gttgcacgta ctcgcgggcg 6901 acacagcgcc actcggggaa gacggtggcc cgctcgtcgg gttgcaagcg cacgcgccag 6961 ccgcggttgt gcagggtcat gacgtcgatg ctggtggcca cctcgccgcg caggctctcg 7021 ttggtccagc agagacggcc gcccttgcgc gagcagaagg ggggcaggac gtcgagcatg

Figure 9 (continued)

7081 tcctcgggcg gggggtcggc gtcgatggtg aagatgccgg gcagcaggtc ggggtcaaag 7141 tagtccaggg gcgtgtcgcg gcggtcgagc cgttgctgcc aggcgtgcag ggccagggcc 7201 cgctcgtagg ggttgagggg cgcccccgcg gggaagggat gggtgagggc ggaggcgtac 7261 atgccgcaga tgtcgtagac gtagaggggc tcctcgagga cgccgatgaa ggtggggtag 7321 cagcgccccc cgcggatgct ggcgcggacg tagtcataca actcgtggga gggggcgagg 7381 aggacggagc cgaggtgggg tttctggggg cgctcggctc ggtagaccac ctggcggaag 7441 atggcgtggg agttggagga gatggtgggc cgttggaaga tgttgaaggc gcagaggggg 7501 aggttgacgg actcgtggac gaagcgggcg taggagtctt gcaagcggag gacgagctcg 7561 gcggtgacga ggacgtcgag ggcgcagtag tcgagggtct gcttgacgag atcgtagcgc 7621 tcatcgtggg tctttttgct ttgcagccac agctccttgt tgaggcgata ctcttcggag 7681 tccttccaat acccttcgtc ggggaatcca tcgctgtctg tccggtaagt gcctttcatg 7741 tagaactcgt tgacggcctg gtagggggcag cagcccttct ccacggagag ctcgtaggcc 7801 tgggcggcct tgcgaagaga ggtgtgggtg agggcgaagg tgtcgcggac catgaatttg 7861 agggattggc acttgaaatc ggcgtccccg cagccccccct gctcccagag ggcgtagtcg 7921 gtgccccccct ctttgctgta ctgggggttg ggcagggcga aggtgatgtc gttgaagagg 7981 atcttgccgc agcggggcat gaagttgcga gtgacccgga agggcggggg gatctcgccg 8041 cggtggttga ccacctgggc ggccatgacg atctcgtcga agccgctgat gttgtggccg 8101 atgatgtaaa tttcccagaa gcggggtcgg ccctggaatt tgaggctttt gaagtgttcg 8161 ggttgcaagt cgtctgggga ggagagccct tccttggcgg cgaggtcgtg caggagttgg 8221 aagttttcca gtttgaagag tcgccagagc tggcgggcaa agtgttgctg cagggagtcg 8281 cggaactctt tgaagcggca gccgatggct ttgggctggg gggtgagcag gtagaagacc 8341 cgggggtggg tgagggaccg ccagacttgc cagccctggt cacgtgctag ctgctgggcc 8401 tcggcggcca tctgctcgtc gccgccgata tgcatgacga gcatgaaggg catgagctgc 8461 ttgccgaagc ggttgatgct ggtgtaggtt tccacgtcgt aggtgacaaa gagccgacgg 8521 gtgtctgggt gggccccgag gggaagaac ttgatctcct gccaccagtg cgaggagtgg 8581 gcttgcacgt gatggaagta gaagtcgcgg cggcggacgg agcaggtgtg ggtctgcttg

Figure 9 (continued)

8641 tagtagcgcc cgcagaattc acattttctg ttctgagatg agcgagtgga tgaggtagag 8701 ttggtgttgg cggacgagga agtgcagggg gaagggcagg agatgatgct cgtcgaggtc 8761 ggggacgggg gccacttggg cctgggcccg tccgggttcc acgcgccaga tctcggaggc 8821 ggtgggccgg agctcttgca tcttggagat gagggtgtgc acgtggaggt cttggaaaaa 8881 tgcgtcggga ggctcgtcgc agagatgcac gcgacagagg gtgcggatgg gcgcggcgag 8941 atgcccggcg acgccatagt acttgatttc ggtgggcacg ccggagcggg ggtcgatgac 9001 gtgcagggac ttggtaccgc gggggcgagg acgttgccgc gcagcgggtt gagggggact 9061 actcgggggg tggcagctcg acgtcggcgg cgttgagcgg gggcagggcg agatgcctgg 9121 cccggagact ggaggcgtag tcgatgactc ggcggttcat gcgttggatc tggggtctct 9181 gggtgaagac caccggtccc gtggttttga acctgaaaga caattcgaca gaatcaatct 9241 cggcatcgtt gacggcggcc tgcctgagga tttcgctgac gtcgccggag ttgtcttggt 9301 aggcgatctc ggccatgaac tgctcgactt cctcctcctc gagttccccg tgtccggcgc 9361 gttcgacggt ggcggcgagg tcgttgctga tgcgcccgat gagttgttgg aaggcgttga 9421 ggccgttctc gttccagacg cgcgagtaga ccacgtctcc gtggacgtcg cgggcgcgca 9481 tgaccacctg ggcgaggttg agctccacgt ggcgggcgca gacggggtag ttgcgcagcc 9541 gctggtagag gtaattgagg gtggtggcgg cgtgctcggt gacgaagaag tacatgaccc 9601 agcgccggag ggtgagttcg ttgatgtcgc cgagggcctc gagccgttgc atggcctcgt 9661 agaagtccac ggcgaagttg aagaactggc tgttgcgcgc cgagaccgtg agctcttctt 9721 ccaagagccg gatgagttcg gccaccgtgg cccrgacctc gcggacgaaa gcttcgggtt 9781 cctcttcctc ctcctcttct tcttccaaga tttcttcttc ttcctctacc aactcgggga 9841 tctctgccgg gggtgctaac tcctcttctt ctacagccgc cgctggtgga acagcagcag 9901 caggggggcgc tcgacgacga cggcggcgga tgggcagacg gtccacgaac cgttctatca 9961 tctctccgcg gcgacggcgc atggtttcgg tgacgggcac tccgtcttcg cgggggcgca 10021 ggatgaaagt gccggcgtag cgcgtgcgcc tcccggcggt gggccgacgc ctgagcccgg 10081 gccgtgcccc gccttccaag tcatggcggc ggcggtcggg gttgggcagc gacagggcat 10141 tgacgatgca tctgattaaa ttttgtgtag tgagaccagc gtgggatctc aagagctgca

Figure 9 (continued)

10201 gatcgacggg atctgagaag cgttgaacga aagcttcgag ccaatcgcaa tcgcaaggta 10261 ggctgagcac cgtgctcatc gtgggggtcc cgcctgatgg aggaaggcct tcttggttct 10321 gtccccccag aggttccgca gaggaagagg aggggggcgg gggttgttgc agcgagagca 10381 ggtagttgaa gtaggccgac ttgagacggc ggatggcggc gaggatgacc aggtccttcc 10441 ttccggcttg ctggacgcgc aatctgtcgg ccatgcccca ggcttgatct tgacacacgc 10501 cgaggtcctt gtagaagtct tgcaggagtc tctcgacggg cacgtcttcg gcctgcccac 10561 cttccatgtg ggtgcggccc agcccgcgca ggggctcgat gagggcgagg tcggccacga 10621 ccctttcgct gaggatggcc tgttggatgc tggcgagggt gccttggaag tcgtcgaggt 10681 ccacgaagcg gtggtaggcg ccggtgttga tggcgtagga gcagttggcc atgagggacc 10741 agttgacggt ctgcgagccg gcgtgcacct gttcgcggta cttgaggcgg ctgtaggccc 10801 tggagtcgaa gacgtagtcg ttgcagacgc gcacgaggta ctggtagccc acgaggaagt 10861 ggggcggcgg caggttgtaa cagggccagt gccgggtggc ggcggcgcgc ggggcgaggt 10921 tggccagcat gaggcggtgg tagtggtaga cgtagcgcga catccaagtg atcccggtgg 10981 cggtggkgct ggccccgcgtg ractcccggg cgcggttcca gatgttgcgc agcggtcgga 11041 agtattccat ggtcggcacg gtctgaccgg tgagccgggc gcagtcgggg atgctctgcg 11101 aatggaggag atatagaatc ttaggcccca ttctgctggt gtgttctttg gcagatgcat 11161 ccggtgctac gtcagatgaa accgccggcg acggcgaccg cctcgtaccc acccccgccc 11221 accacggccc aggcggcggt agctagtgga gccggcgcgg cagcagcagg aggaggagag 11281 ctgacggggg gtcgccgcgt gcccgagggt cttttggacg agggcgaggg tctggcgcgt 11341 ctgggggcgc acgaccccga gcggcacccc cgcgtgcagc tgaagcggga cacgcgcgag 11401 gcgtacgtgc cgcgacgcaa cgcgttcagg gagcgtgagg gccaggaacc cgaggagatg 11461 agggatttga ggtttcgggc cggtcgggag ttgcatgatc tggatcgcga gcgggtgctg 11521 cgatcggagg atttcgaggt ggacccgcgg acgggcgtga gtcccgcgcg ggcgcacgtg 11581 gaggcggcca acctggtgag cgcgtacgag gagacggtga agcaggagat gaactttcag 11641 aagagtttca acaaccacgt gcgcacgttg atcgcgcgcg aggaggtggc catcgggctg 11701 atgcatctgt gggactttgt ggaggcgttc gtgagcaacc ccaacagcaa gcctctgacg

Figure 9 (continued)

11761 gcgcagctgc tgctgatcgt gcaacattcg cgggacaacg aggtgtttag ggaggcgctg 11821 ctgaacatcg ccgagcccga gggtcgctgg ctgctggacc tgatcaacat cctgcagagt 11881 atcgtggtgc aggagcgttc gctgagtctc ggggagaagg tggccgccat caattatagc 11941 atgttgagtc tgggcaaaca ctacgcccgc aagatttaca agagcccctt cgtgcccatc 12001 gacaaggagg tgaagatcga tagcttttac atgcgcatgg ccctgaaggt gctgacgctg 12061 agcgacgacc tgggcgtcta ccgcaacgac cgcatccaca aggccgtgag cgccagtcgc 12121 cggcgcgagc tcagcgaccg cgagctgatg cactgcttgc atcgggcgct gacctcccac 12181 ggcgacgagc gtctggaggc cgaggagttg ctggccggct cgggcgctct ccgcagtgct 12241 gaaaggcagg agcccagcta ctttgacgcc ggggcggatc tgcgatggca gccgagtcac 12301 cgggccgcgg ccgccgccat ggccctgagc cgctacggtc cgcccgaggc cgaggaggag 12361 gaggcaggct atgaggagta tgatgactac gaggacgaag acgggctcat ggactagaat 12421 tttttgtta gggcaggaag cgagcaagat ggaccccaac ccaccaccac cacgtcagct 12481 gaaccccgag gcccgggcgg tcgtgcagag ccagccttcg gcgcccaccg cctccgacga 12541 ctgggatggc atgatgcagc ggatcatggc gctgacggcg cgcaatcccg acgcgttccg 12601 gcagcagcct caggccaacc gattcgcggc catcttggaa gccgtggtgc cctcgcgccc 12661 cgaccccacc cacgaaaagg tcttggccat cgtcaacgcc ctggcggacg cgggggccat 12721 ccgtcccgac gagggtgggc agatctacag cgccctcttg cagcgcgtgg cccgttacaa 12781 cagcaccaac gtgcagacca atctggaccg cctggtcacg gacgtgaagg aggcggtggc 12841 ccagcgcgag cgttatttca aggagggcaa tctcgggtcc ctggtggccc tgaacgcctt 12901 catcggctcg ctgccggcca acgtggtccg cgggcaggag gactacacgg ctttcatcag 12961 cgcgctgcgg ttgatggtgg ccgaggtgcc ccagagcgag gtctaccagt cgggaccccca 13021 atactttttc cagaccagtc gtcagggctt gcagacggtt aatctgacgc gggcctttga 13081 gaacttgcat cagttgtggg gcgtcaaggc ccccgtgggc agcgaccgct cgaccatctc 13141 gtccctgctg acccccaaca cgcgcctgct gctcttgctc atcgcccccct tcacggacag 13201 cgggctgatc tcccgcgaca cttacatcgg ccatctgctg accctgtacc gggaggccat 13261 cggccagaac cgggtggatg aaagcacttt ccaggagatc acgagcgtga gccgggccct

Figure 9 (continued)

13321 gggccaggag gaccccggca gcttggaggc cacgttgaac tttttgctga ccaacaagcg 13381 gcagcgtatc cccacccagt acgccctgaa cacggaggag gagcgcatct tgcgctacgt 13441 gcagcagtcg gtgtccctgt atctgatgcg cgaggggggcg agtcccaccg ccgcgctgga 13501 cctgacggct gccaatctgg agcccagctt ctacgccagc aaccgggcct tcatcaaccg 13561 cctgatggac tacttgcatc gggcggcggc cattaatccc gattacttta ccaacgccat 13621 tctgaacccc cactggttgc cccctcaggg ctttttcacg ggggagtttg acctgcccga 13681 ggccaacgat ggctttttgt gggacgatat cgacagcagt ctggtggcca agaaggaggg 13741 cggtgacgag cagagccggc gcacgagcct ggcagacctg ggggcggcta gcagcttccc 13801 cagcttgggc tcgttgtttg agagtagcag cagttcagct agcagcagca gacgcccgag 13861 ttctagtacg gggcgggtga cgcggccgcg gctgccgggg gaggacgagt acctgcgcga 13921 ccccctgttg ctgcccagtc gggacaagaa ctttcccaac aacggggtgg agaccctggt 13981 ggataagctg cggcgttgga agacctacgc ccaggagcag cgcgagttga ctcagggcgc 14041 gcggccccgg gaccctcggg atgactcagc gtggcatcag catcggcgcc agcgggagta 14101 tgacgaggac gcggctagcg acagcagcgt gttggatctg ggcgggagcg ggaacccctt 14161 cgcccacctg atgccccgcg gcgggagtcg gcgtctgtaa gcccgcacgc ggtgtgtggc 14221 acgtgcaaaa aagaaaaata aaaaaacacg agtacttacc aaggccatga cggagccgcg 14281 ttgttgtgtc tctctcctct cctctttttt cttctttctc tatctgatcg gcggtgtggc 14341 ggtggcggcg tagaagatgc aacgcagtgt gccggtgccc gcgagcccac ctccgtctta 14401 tgaggaggcg atggcgtcag tgggggcggt gcttcctccg ccggtgatgc aggctccgta 14461 cgtgcctccg cgctacctgg ggccgacaga ggggcggaac agcatccgtt actctgagat 14521 gcaggcgctg tacgacacga cgcggctgta cctggtggac aacaagtccg ccgatatcgc 14581 gtccctgaac taccagaacg accacagtag tttcttgacg agcgtggtgc agaacagcga 14641 ctttagccct caggaggcga gcacgcagac ggtgaatctg gacgagcgct cgcgctgggg 14701 cggggagctc aagaccatcc tgcacacgtg catgcccaac gtcaacgagt tcatgttcag 14761 caacagcttc cgggcgaggc tgatgactca gaaaaagaat ggggtggccg agtacaagtg 14821 ggtggagctg accatccccg agggcaattt cagtgagatc atgaccctgg acctgatgaa

Figure 9 (continued)

14881 taacgcggtg gtggagcact atttgcaagt ggggcgtcag aacggggtgg aggaggcgga 14941 catcggggtg aagtttgaca cacgcaactt ccgcctgggg tacgacccgg tgacgaagct 15001 ggtgacgccg ggcagctata cgtacgaggc ctttcatccc gacatcattt tgctgcccgg 15061 gtgcgcggtg gactttacct acagccgcct gagcaacctg ctgggcatcc gcaagcggca 15121 gcccttccag gagggtttca tcatcgagta cgatgacctg gtgggggggca acatcccggc 15181 tctcctcgac gtggcggcct atgaaggtag tctgcagggt ggcggtggca gcggcggcgg 15241 atcgaccacc gcggccgaga cgcgagacgg gcctgctgaa gacgctgacg gccccgtcct 15301 cgtggacgct gatgacgtgg agtacgagat gcgcggcgat ggtcacatgg tccgcaagag 15361 gcgtagcgcc tcacctgtgg cggagcctgc ggcagatcct atccctaaca gccccgttat 15421 caaaccaatt acaaaagact caaaaaaccg aacctaccat gtagacgagg taaccaacca 15481 gacggcctac cgcagctggt acctggccta caactacggg gacccggaga agggcgtgcg 15541 ctcgtggacg ctgctgacga cgcccgacgt cacgtgcggc tcggagcagg tctactggtc 15601 gctgcccgac atgatggtgg accccgtgac cttccgcccc tcgcagtcgc ccagcaacta 15661 cccggtggtg ggcgccgagc tcatgcccgt gcagtcgcgc accttttca acgaccaggc 15721 cgtctactcg cagctcatcc gccagaacac ctccaagacg cacgtcttca accgcttccc 15781 cgacaaccag atcctcgtca ggcccccgc gcccaccatc accgccgtca gcgaaaacgt 15841 gcccgcgcac accaaccacg gcacgctggc catgcgtcac agcctgcgcg gcgtgcagcg 15901 ggtcaccgtc accgacgcca ggcggcgcac ctgtccctac atctacaaga ccttgggcat 15961 tgtcaccccg cgggtcctct ccagtcgcac cttttaagca tgtccttctc cctcctccat 16021 cctcagcgcg cgcgcggatg tccattctca tctctcccag caacaacacc gggtggggct 16081 tagggaccaa caaaatgtac ggaggagcca agcgccggtc cagcgaatac cccgtgctcg 16141 tcagacgcca tttcagggcc ccctggggag cccgcaaggg acgcctacgt cagcgcacca 16201 ccgtagatga cgtcatcgac agtgtggtcg acgacgcccg cgcctgggcg gatgctcagc 16261 cggcccccgc ggccgtggct gccgccgtgg gtcgtcgggt ggccagacgg gcccgtcgcc 16321 ggccccgggc cagcgcccgc tccaccgtgg acgcggtcat cgatagcgta gtcaggggcg 16381 cgaggcggta cgccgatcgc aaggcccgtc gcgggcgtcg cagcgccgcc gtgtcggccg

Figure 9 (continued)

16441 ccaggaggct ggtgcgcgga gcccaccgcg tgtaccgccg caagctgcgg cgacgggaca 16501 gtcgacggag gggggccgcc cgggccgcgg ccgctgccat cagaagcatg gcgccgcgcc 16561 ggcgcaacgt gtactgggtc cgggacgcca cgaccggcac ccgggtcccc gtgtattccc 16621 gccccaagta aatttaataa aaattacacc tgattgcacc tcctagctcg cctccgcctt 16681 ttccatccat ccaaccaaca acatgaccac gcgaaagatc aaagaagagc tgctgcaggc 16741 ggtggcgccg gaggtgtaca cgccgctggt ggtgccccaag cgggagatta agagggagtt 16801 gaaaagggag atcaagggcg agctcaagcg ggagcggggg gacgttaagc cctttagaag 16861 caggaagcgc aagaaggacg aggacggcga cgtcctgcta gtgggcgccc ccggcaccga 16921 gggggtggag tttgtcaggg agtttgcccc gcggcgacga gtgcagtgga agggacgcaa 16981 ggtgaggcct ttcttgcggc cgggcgcggt cgtgcagttc accccgggcg agcggtccac 17041 atggcgcctg cacaagcgga gctacgacga ggtgcacacg gacgaagaca tcctgcaaca 17101 ggcggcggcg ttggacaacg agttccgcta cggcaaaaga ccccgaccct acgaggatct 17161 catgatcccg ctggacgagg gcaaccccac gcccagcctc aagcccgtca ccctgcaaca 17221 agtgctgccc gtctccacca ccacggaccg caaacgcgga gtcaaacgcg agcggctggg 17281 cgacctgcag cccaccgtgc agctcatggt gcccaagcgc cgcaagatgg aagacatgct 17341 cgaagacgcc ttcatggacc ccgcggagcc ccccgaggtc aagatccgac ccatcaaggc 17401 ggtggcgccc ggcatcggcg tgcagaccgt ggacgtggag atccccctgc gacaggcggc 17461 cgccgccgtc gccgacgtgg acatgggccc cagcgtgcaa gaagtgggca cggaccccat 17521 tccccagccg ccggcccccg tgtcctccct gatcccgatg ggagcggccg tggcagcggc 17581 ttccaagacg gtctcggcgg ggacgcagac ggacccctgg atgggggcgc ccgtgcagcc 17641 cgcccggcgc cgtcgccgct acccgaccgc cagctcggtg atgcccaact acttgttgca 17701 tccgtccatc accccgacgc ccggctaccg gggtcgacgg gcccctcgcc ggcgcgccgc 17761 cgcctcgtct tcctaccgca gccggaggag acccgcttcg cgccggagcc gcgcggtgac 17821 ccgagtggtg acccgccgcg ggaggcgcct gactctgccc gccgtgcgct accatccgtc 17881 gatcgtcttg taagcttttc cactgctcct accttgcagc tgcgcagcga acatggcttc 17941 caaaatgacg tgccgaatcc gcatccccgt gccctaccac ccgtcgagac ggcggaggag

Figure 9 (continued)

18001 aggcggactg agcgggagcg gcctgggtgg tggcgcccgg cggctgaggc gacgacgggc 18061 cgtgcgcgga cacatgcgag gggcttttt gcaggccctg atccccatca tcgccgcggc 18121 cgtgggcacc atcccgggca tcgcgtcggt ggccttgcag gcttcgcggc gcaactaggt 18181 tgcttgttcc tcctcctcat caccatggtc tctctgctcc tcctgctgat ctcgtcgccg 18241 cctctgccgc cgccaccaac gttgccgctg tcggacttca ccaggacact ccatcaccgg 18301 cgcttcgagg atggaagata tcaatttttc ttccctggcc ccgcggcaag gctcgcgtcc 18361 cctgatgggc gcgtggggtg agatcgggac gaaccagatg aacggcgggg ccttcaactg 18421 gggcagcatc tggagcgggc tgaagagttt cggctccacg gtgaaaaatt acggtagcaa 18481 ggcgtggaac agcaccaccg ggcagatgct tcgcgacaag cttaaggaca cgggggtgcg 18541 ggaaaagatc gtggagggcg tcacctcggg catccacggg gcgctggatc tggcgcgcca 18601 ggagatggag aagcatatca actcccgcct ggaccatccg cgtcccgacg tggaggtcga 18661 ggagatgctg ccgggcttga acgagaagcc ccccctggcc ccgtcggcgc ctcccaagga 18721 ggaccgtctg cccgagaagc gtccccggcc cgaggctgag gaggagctgg tgatccgcac 18781 ggacgagaag ccccccagct acgaggagat ctttggcaag gacatggcgc ccccgccccc 18841 ggtggcctcc acgtacccca tgacgaagcc gatcgccccc ctggcgcggc cggtgatcgg 18901 gacgtcttct agcaacaaga aagtgccccc tccgcgtcct ccaccgccca cgagacgtcc 18961 caccgtcccg gccgtggccc ccgcgggtcc cgtggatgtt ccggtgacct tggatcttcc 19021 gccgccgccg tctgccgtgg tgactccggc tgctccgcct gtggccatcg cgacccccgc 19081 caccccggcc gccccgtccct cgtactctcg ccccagccgc cagagttggc agtcgaccct 19141 gagcagcatc acgggtctgg gagttaggag cctgaaacgc cgccgctgtt actaagcaat 19201 ccttcaatac aaccacgact ctgctttacc atgaacacct gtccgctgtt gttttttcat 19261 cgtcgttgcc gtcgccgccg cctccgtcat cgtcgtcgtc tggtctgctg cgcgcgtgtg 19321 acgtcaccat catcaggaag taggaagcta cctccactac acagcctgcg aagatggcga 19381 ccccctcgat gatgccgcaa tggtcttaca tgcacatcgc cggtcaggat gctacggagt 19441 acctgagtcc gggtctggtg cagtttgccc gggcgacgga aagctacttt tctctgggca

Figure 9 (continued)

19501 acaagttcag gaacccgacg gtggctccga cccacgatgt gaccacggac cgttcccagc 19561 gtctgacgct gcgcttcgtg cccgtggaca aggaggacac cgtgtactcc cacaagtgcc 19621 gcttcaccct ggcggtgggc gacaaccgcg tgctggacat ggccagcact tactttgaca 19681 tccgcgggry mmtcgaccgg gggcccagct tcaaacccta cagcggcacc gcctacaact 19741 gcctcgcccc caagggcgct cccaacaatt gccagtggat gaccacagga gaaaacccta 19801 aaaccagaac atatggccag gcgccatttg aaacagattt cattaaccaa aataacaaca 19861 taggtgttca ggttggttgg acaacagctg aagttcccca accaataata gccgactcca 19921 aataccaacc agaaccacag tctggacaaa atcaatggca gtcagctgta acatcaacgg 19981 ttactgaatt ttctggcaga gttctgaaac cagatactcc tcaacttcca tgctatggtt 20041 cttatgctag acccactaat gattatgggg gtcagtgcag ggaaggtcaa caggtggatc 20101 aagtgtattt caatgttgaa aatcaagtca atgctcctaa agtcattctg tactctgaaa 20161 atgttaacat agaatcgcca gacactcata ttatctttca ccctacaccc aacggtacac 20221 atccaaatgc attggaagat atgttaggac aacaggcctc tcccaataga cccaattaca 20281 ttggtttcag agacaatttc attgggttta tgtactacaa cagcactggc aatcttgggg 20341 tcctggcggg gcaggcgtct cagctcaacg ctgtggtgga cttacaagac agaaacactg 20401 agctgtcgta ccaactgatg cttgatgcgc tgagtgatag aacgcggtac tttgcaatgt 20461 ggaatcaggc tgtggacagt tatgatcccg acgtgaggat cattgaaaac catggttgtg 20521 aagatgaaat gcccaactat tgcttccctc tgggcggggt tggtccaata gagaagtgga 20581 ttggtttaaa aatcaacaaa accgccaatc cagctacttt cagtcaagac aatgaaatat 20641 ctacggacaa tagaattggt actggtaaca tcaatgccat ggagatcaac atccaggcga 20701 atctgtggcg gagtttcttg tattccaacg tggccctcta cctgcccgac tcatacaaga 20761 tcacccccga taacgtggcc atctctgaca atgaaaattc atacgattac atgaacgggc 20821 gcatcgcccc cgtaggtctg atcgattact tcatagatat cggggcccgg tggtcgccca 20881 accccatgga caacgtcaac cccttcaacc accaccgcaa cgcggggctg cgctaccgtt 20941 cccagatcct gggcaacggc cgatacgtac ccttccacat ccaagtgccc caaaagttct 21001 ttgccatcaa aaacctcctc ctgctgcccg ggtcctacac ctacgagtgg accttccgca

Figure 9 (continued)

21061 aggacgtcaa catgatcctg cagagcacgc tgggcaatga cctgcgagtg gatggcgcca 21121 aggtcagcat cgacagcgtc aacctctacg ccaacttctt ccccatggcc cacaacaccg 21181 cttccaccct ggaagccatg ctccgcaacg acaccaatga ccaaaacttc aacgactacc 21241 tcagcggagc caacatgctc taccctatcc cggccaacgc caccaacgtg cccatctcca 21301 tcccctcgag aaactgggcc gccttccgag gctggagctt cacccgcatc aaggccaagg 21361 aaaccccctc catcggggcc ggtttcgacc cctatttcaa ctactcgggc accattccct 21421 acctcgatgg caccttctac ctcaaccaca ccttccgccg cgtctccatc atgtatgact 21481 cctccgtcag ctggccgggc aacgaccgcc tgctcacgcc caacgagttt gaaatcaaac 21541 gggccgtgga cggagagggc tacaccgtct gccagagtaa catgaccaag gactggttcc 21601 tcatccagat gttgagccac tacaacatcg gataccaggg cttcttcgcc cccgagtcct 21661 acaaggaccg gctgtactcc ttcttccgca acttccagcc catgagcagg caggtggtcg 21721 accccatcaa ctacaaggac tacaagaagg tcaccgtgcg ctaccagcac aacaacacgg 21781 gcttcacggg cgatgtcacc cccgcggcca tccgggaggg acacgcctac cccgccaacg 21841 ccccctaccc cctcatcggg gccaccgcgg tgccctcgct cacccagaaa aagttcctct 21901 gcgaccgcgt catgtggcgc atcccctcct cctccaactt catgtccatg ggcgccctca 21961 ccgacctggg gcagaacatg ctctacgcca actcggccca cgccctggac atgaccttcg 22021 aggtcgaccc catggacgag cccaccctgc tgtatgtctt gtttgaagtc tttgacgtgg 22081 tccgcgtgca ccaacctcac aggggcgtca tcgaggccgt ctacctgcgt accccattct 22141 cggctggtaa cgccaccaca taaacaactg ctgactgatg ggttccagcg aagaggagct 22201 caaagccatc gcgcgagatc tgggctgcgg gccctctttc ttgggcactt tcgataaacg 22261 ttttcccggt ttcatctccc cccacaagct cgcctgcgcc atcgtcaaca ccgcgggccg 22321 agagaccggg ggcgtgcact ggctcgcgct gggatggaac cccaaatcca agacggtcta 22381 cctgttcgac cccttcggct tttcagatca gaggctcatg caaatctatc agttccagta 22441 cgagagcctc ctcaaacgca gcgccctggc cagtaccgag gaccactgcg tgactctggt 22501 caagagcact cagacggtcc agggacccca cagcgcggcc tgcgggctct tctgctgtct 22561 tttcttgcat gccttcgttc actggcccga ccgacccatg tctggaaacc cgaccatgga

Figure 9 (continued)

22621 cctcgttgac ggagtcccca acgccctcct caactccccc accgtccaac ccaccctgcg 22681 caagaaccag gaggccctct acgccttcct ccgctcccac tccgcttact tccgtcaaca 22741 cgagacccag atccgcgagg ccacccgctt cgataaagcc ctcaaaatgt aaaagaacca 22801 cactggaaac tgttttttgt ctgactgaaa aataaattcc agctttattt gaaaaatcag 22861 acacggctca gactggctca atcaaacagg tcttggcacc cgtcgtccac cgccgcgggg 22921 aaagcgacgt tgcggtactg caagcggggg gaccacttgt gctcggggaa tttcaggggg 22981 ggaagccgct cgccctcaaa cacctccaaa aacatgttgc gcgccagctg cacgctggtg 23041 atcaggtcag gggcagagat cttgaaatcg caattgcgct gggggttggc cttggtattg 23101 cgatacaccg ggttgcaaca ctggctcacc agcaccacgg ggtacttggc gctggcccgc 23161 atcacgggat cccgaatctc ctcggggtcg ataccctccg agttgggaat gttaaagggg 23221 gtcagcttgc acacctgccg tccgctcagc ggcccccgagc gggggtggtg attgcagaag 23281 caggtcatgc acagtaacag acagtcgcga cccttcttgg cctgagggta gcatgcccgc 23341 atgaacgccg ccgcctgttg gaaacccacc tgcgccttgg tgacgtcaga gtaggacatt 23401 ccgcaagaca ggttgctaaa gaccccgtta gggttgctcg cgtcgtgcaa gcacaccacc 23461 gcctcctcgt tacgcaactg caccacgtta cgaccccatc ggttctgggc aatcctggcc 23521 ttctggggct gctctttcaa agcccgttgg gcattctcgc tatttacatc catctccacc 23581 gtctgctcct tcctgatcat catcatgccg tgcaggcact tcacctcccc ctccttcacc 23641 gcactctggt ggtcccacat cacacacccc gtggggttcc agccctcggg ctccacccgc 23701 aactccgcaa agttggccac cagctgccac agcatgcgtc ccattatgtg gacgaagctc 23761 ttgtaagaag tgaaggtcag ctggggcgtg ttgtggctct gattcagcca gctctgacag 23821 accttggaca tcatctcaga atctaccggg ctcatattca agccctccgg gggcagctgc 23881 accttgaact tgttggtcag cgtgaccagc atgttctgag cggtggtgta agcctcaaag 23941 ggaacggccc tcccaacact caaaagcgct acggagccag cgccgctgga cccggcagtc 24001 gtagcactcg ctgcccccga ggtaacagag ggacccgtgt tcgaaccctc cgtctgcccc 24061 ttgctcgggt ccatcttttt tttttaaga ggagcgttcc cgctcaagtc caggctcgtg 24121 ggtctcttca gctgctgctc gctgatgcgt tccttgcttc cgtcggcgtg caccacggtg

Figure 9 (continued)

24181 ggcgggttgg taaacagcac cttcacgatc tcgggctctg ccgccggctc ttcctcttct 24241 tcgctgctgc ttccgctgct cacgctcacg ggcgacggag gcagctccgg tttcgtttcc 24301 agcttctgct tgcggcggct ccgcttgggg ggcagcggag gcgggggatt tccctcctcc 24361 tgcggctggt tgctgctgct ggtgctctgc tggggcggtt ggtcgctcat ttttttcttc 24421 tcctaggttt ttgggagagg aacagcatga gcgactccgt catcagcatg gaagactttg 24481 aaccaccccca gcaagatcaa tcgacagcac cacccaccga tgatgacgtg cccatagaat 24541 cagacgtgga gttcctcact gaggagcagc accgcctgcg tctagagcag gaggctgatc 24601 agcagataat gaagaaagag caggaaaccc agacagagga tgagcaggca aatcatgacg 24661 cagttcagga ggaggatgat tctggggaga agcagcagca gcgacatggc gatggctaca 24721 tcacagacga gatcctgctg acacacatcg cgcgccagag tctcatcgtg caagacgccc 24781 tggccgaccg cagccagatc cccctcaccg cccgcgacct caccgaggcc tacgagcaat 24841 gcctcttctc gccgcgcgtg ccccccaaac gccaacccaa cggcacctgc gagcccaacc 24901 cccgtctcaa cttctacccg cccttcgtcg tgcccgaggt cctcgccacc tatcacatct 24961 tcttccaaaa ttgcaagatc cccctctcct gccgcgccaa ccgcaccgcg gccgacgagc 25021 gcctcgccct cggcgaaggg gatagcatac ctgatatcgc ctccctggaa gaggtgccta 25081 agatcttcga gggtctcggt cgcgacgaga agcgcgcggc aaactccctg caaggcaacg 25141 gagacggaga agagagtcag tcggcgctcg tggagctcga aggcgacaac gccccgtctcg 25201 cggtgctcaa acgcagcatc gatgtcaccc acgcggccta ccccgccatc aacctcccgc 25261 ccaaagtcat gtcggccctc atggatcagc tgctcatcaa acgcgcggcc cccatcgacg 25321 ccgaacgcga aacatacaac cccgacgagg acgacagcga ggacggcaag cccgtggtct 25381 ccgaccagga gctcgctcgc tggctcaacg tggccctcga ctcccccctg ctggaggaac 25441 gacgcaagac cctcaccgcc gtcctcctcg tcaccctcaa cctcgaatgc ctgcgccgct 25501 tcttctccca ccccgacacc ctgcgcaagc tggaagagtc cctgcactac accttccgcc 25561 acggctacgt caggcaggcc tgcaagatct ccaacgtgga gctctccaac ctcgtctcct 25621 acatgggtat cctgcacgag aaccgactcg ggcagaacgt cctccactcc accctcaagg 25681 gcgaggcccg tcgcgactac atccgcgact gcatctacct ctacctggtc tacacctggc

Figure 9 (continued)

25741 agaccgccat gggcgtctgg cagcagtgtc tcgaggagcg caacgtccag gagctggaaa 25801 agatcctgca gaagcagcgt cgcgccctct acacgggctt cgacgagcgc accatcgccg 25861 ccgaactggc caccctcgtc ttccccgaga agctcatgca gaccctgcag aacggcctgc 25921 ccgattttgt cagccagagc atgctgcaca acttccgcag cttcatcctc gaacgctcag 25981 gcatcctccc ggccatgtcc tgcgccctcc cgtcagattt cgtccccatc tccttccgcg 26041 agtgtccccc gccgctgtgg gcctacacct acttgtttca gctggccaac tacctcatgt 26101 accacagcga cgtggtcgag gacgccacgg gcgagggtct catggagtgt cactgccgct 26161 gcaacctctg caccccccac cgctcgctga tttgcaaccc cgcgctgttg agcgagagcc 26221 aggtcatcgg taccttcgag attcaagggc cagacgccaa aaagcaagag gccggtgagg 26281 aaacggccgt gggatccacc tccggcttca aactcaccgc gggtctgtgg acctcagcct 26341 acctgcgcaa atttgtacct gaggactacc acgcccacac catcaagttc tacgagcacc 26401 aatccccggt caagagccgg gtcgaaccct cggcctgcgt catcacccag agcagcatcg 26461 tggcccaatt gcaagccatc caaaaagccc gcgagtcctt cctcctgaaa aagggcaaag 26521 gggtctatct ggacccccag accggtgagg agctcaaccc ccttcccccc gccgcgcagt 26581 tatccctcag agatggcccc gcgaaagccg gctcccgcga agaagcaacc tccaccaccg 26641 ccagtccacc ccatctggga ggacgacgag gaggagtaca cggaggacga ggaggacctg 26701 ctgacagacg aggaggacat ggagggtctg gaagacatcg aggaggaaga cgaggaggag 26761 gatctggacg aggatccgca ggaggagccc agggagcagg cggttgcaga cagccagcac 26821 ctagcgccca gggcccctca ggcggctcct gccccgtcag cagcagcagc tccttccaag 26881 agtcgcagta gatgggaccg caagccagct gccgcgggta agggatctta caagtcttgg 26941 cgagcccaca aagcccgact gctgtggtgc ctgggcgaga gcgggggcga cgtgaatttc 27001 acccggcgct acatgctctt ccaccacgga gtcaacatcc cccgtaacgt catccactac 27061 tatcatcaat cctacagcgg cagcgactgg gccgaaatcg ccgcggcagc cagcctcctc 27121 gaggaaggga aaaaccagca gcagcaacag cagcagaagt aaaatccccc tgaggaaaac 27181 acctgctacc ggtagcagca gcggcgaaca gggcagcacg cgagcgctcc gggagaagat 27241 cttccccacc ctctacgcca tcttccaaca gggccgcgga cacagcctcg atctcaaaat

Figure 9 (continued)

27301 caaaaaccgc tctctgcgtt cccttacccg cagctgtctc taccacaaga gcgaggatca 27361 gctccaacgc actctcgagg acgccgaggc gctctttaat aaatactgcg cctccaccct 27421 cccgcccctc ggtgatcatt aacccgcccg gcccgcgcgc gggaaaacgc cgctgactca 27481 cacctgaggt cagagtccga ttcccaccat gtccaaagtg attcccacgc cttacatgtg 27541 gagctaccag ccgcagatgg gactggcggc gggggcgtcc caagactact ccacgcgcat 27601 gaactggctc agcgccggac ctagcatgat cgcccgggtc aacggggtcc gcgacgagcg 27661 caaccagatc ctcatgaagc aagcggccat caccgccacg ccccgaggga ctctgaaccc 27721 gccaagttgg cccgcggatt tggtgtacca ggaaacgccg ccgccccgaca ccgtgctcct 27781 cccgcgtgac gcacaggccg aagtccagat gacgaattcg ggtgcccagt tggccggggg 27841 cggagtcagg ttcacgccct accgccggcc gggcataaat accctgcgct ttcggggcag 27901 aggcgtacag ctcaacgacg agacagtcag ctcctcgttg ggattgagac cagacggagt 27961 cttccaaatc ggaggatccg gcctctcgtc tttcacacct cgccaggtct acctcaccct 28021 ccagaccgct tccagccggc ctcgctccgg tggcatcgga accctccagt tcatcgagga 28081 gttcgtgccc tcggtctacc tcaacccctt ctcgggacac cccggtcact acccggacga 28141 cttcatcccc aactacgatg ccgtcagcga ctcggtagac gggtatgact gatggagatc 28201 tagaggctga agttgaaaaa gctcgcctcc gccatctcgt ccactgccgt cggcctcggt 28261 gctacgcccg ggacctgctc ctgctcgagg gtttcttcta cccgcccaac catcccgaag 28321 gccccgctca cggcctccgc ctcaccgtac ccgagaccca gcgctcccgc ctggacaact 28381 tcttcaccgg tcggcccttg ctcgtcgaga ccacccacgg acccgtgacc ctcagcgtca 28441 cctgcatctg cgccgccaca cagctgcatg aagagctgtt tgagcgtctg tgtactatct 28501 tcaatacttc tacttgccct cagcagtgag ttaataaact tgaactgcac tgaacaacca 28561 gccactcggg gtgatctgtt ctacaacgcc aacgggtcac tgatcgtctt ccttcagtgt 28621 cccaaccact ccagcctctc ctaccccatc cactggtctt acaacttctc cgtccccgtc 28681 gccaacttca ccccggccgt caacgccact cgacagccgc ctctgctcgc ccatcagggt 28741 tggaacgaga ccgtcgccaa cggggttgag tctgtgatcg tcctcgagaa cccaccggag 28801 ggcgtctact gctgcctctc caacctcacc gtctgcagtt gctggaactt cactgacttc

Figure 9 (continued)

28861 aaccgcaccc tcgagggctt cagcaccacc accacccttg ctaccactac tacctcggta 28921 gaaaccacca gcaccgccgt cgccaccact accgccaccg tcgacctccc actacccgag 28981 ggagctcagg aaggacagga cttttacttt gtggaggaga gggaaactca tctccagcta 29041 gactccaagt tctggactgg tctgactctg ggactagtgc tcttcgtctc cttggttctc 29101 ctctgcctgg tggaatacag gcgaaaccaa gtcggtgatt cctacaccac tcaggagcct 29161 ctcttgcaca cagtctgaga ccactcaggt aaatatgagg gtctggcaat acctcgtcag 29221 ggggctcatg ctctctctgt tttttctcct caaagctgcg agtcccttca cttacatctt 29281 ctccattctc ccgtgggatc atatggttaa cctgccttgt catggggatg ggtctgtggg 29341 cccctgtccc cattcccggg tccacgaatg gaccttcaac gggtcttaca taggctcctt 29401 ccagtgctcc aacggggtga ttcctaatga ctggtctaac atcttagctg gaaacttcac 29461 caccttgtct gtcctcaatc cccctcgagg aaaatactgc tgcactctca gggatcgata 29521 cgaggaatgc ttcggggtgg gcttagaatc ctacgtccac cagttgggag cccatgatag 29581 gaatgtctat gaagaaacca cctctgctcc ttctcttccc ttctccatta tgccttccaa 29641 tcccggggag tttgtgctgc tggtctttct gtttgtgtgc atgttcttgg gggcctacct 29701 cctgtaccgc atcaggcggc tgtatgtgac taaccaggag tctttttctt atgttcaatt 29761 tactaacagc ccagaataaa tcagcatggc caacccacgt ctgctcaccg tcctcgcttg 29821 tctcgctatt cttcttacct ttctaccact ctgtcaaact acttgccatg aaagagattt 29881 cgaggttgaa ataggcggag atttagacat tgatgtattc caagtttttg aacattggca 29941 tatcaccttt aaaaggttgt acaacagaac tgttggccaa cgtttagtat gtgatagcag 30001 ctcaggtcct actgactatg gtttttcttt taatgaccat tttttacaac tcagacatgc 30061 caccaaagat cacattggca tttttacgct ggaagtggaa tacaatgacc ccacatactg 30121 gtttccagca gtagcaagat gtcctattaa cattactctg gttgatttca ctgaaccaaa 30181 atgtattctg ggatgcactg ttgaagacca tggcttcatt aaagatgtaa tgcttatgtg 30241 caacacaagc catgacataa taatgacagt tgtcagcgat actgtttcga ctgacatgca 30301 ccaccgtttt ttagctactg cttacacttc aaatttagtc attttagtgg tggctttcaa 30361 taatcagtct actgcaatta cccactttgt aatgacacct ccatggatca atgacaccag

Figure 9 (continued)

30421 ctgtcccaat ctcattacta ttaacatcac aacaagacac ggtttcaatg acaacagtga 30481 atgggaagaa gttggacagc ttgggttttc acacagtgca cagtcagatg ctgtttgtga 30541 tcacgaccac acttcctaca ttttgatcat cgtcatcgcc ttcctcttca tgctagcaga 30601 gctgctcttt atcctctacc tctaccacaa gtacttcaac tggggcaggg ggtacagagg 30661 gccgcccatc atcctcgaaa acaaatctga cgcacctgcc cccaaatatt cctacaggta 30721 tgcctaggcc gtctgtcatc ctcacagcag tcacagttct ccctgtgctc tgttctctag 30781 tggccctcag cgcatccaac tccctccaag gcacctgcct tccctcctgg gccggactct 30841 tggccttcgc tttgcttaac atcacctgtc tgctcagcac cctctgcttc ttcttctccc 30901 tcgcccaact cattgactac gcgagattca gaagaaatca cagactcaat cgagaagcag 30961 gaccagccgt catcaacctc atcaacctcc cccgcgccca accatgaact gcaccctaga 31021 cttctacgga aaaatcttct tctttagaga cccctgtgaa tgtaccacca tggactatgg 31081 catctacctc atatatgaga tcatgctgct aatctctgcc gggttagcag cggctatcat 31141 gcacactaac tacctcaaac taccatgggt aaaaagcccc aattccaacg ctcctccctc 31201 tccacccccc agccctcctc ctcagcctcc tgccgctgtc gctctcatcc ctccaccgcc 31261 acctccgccc cccgtgtacg cgcgagtaga ccccgacccg ccaccagcct acttcgagat 31321 ctactttgga gacgatggaa cagaatcaga ctgacgtgca gctagagatg gatggcctca 31381 tggcagagca gcgtctcctc ctccagcaag ccaacgaccg ccaccgcaaa atgaaaacag 31441 acgaggtcag aacctatgcc aacctgcacc aatgcaagcg cggcaactac tgcctcgtca 31501 aacaatgcca tctcgagttc accacctgcg ctaacgggga ccacgagctc atcttctccc 31561 taccctgtaa ccgcttctcc agcgtctaca ccgtgggtca gcacaccgtc aggctgggca 31621 tcacccgcgg tgagacttca ggatctatcc gctgctcctg ccacaatcct gattgtctac 31681 acactctaat gaagaccctg tgtggtctca aagataattg ccccatctga ttaaactgtg 31741 attcaataaa gattacctga aatctgacag caggtctccc aagtctagtt tgtctagcac 31801 ctccacgtag cgcccctctt cccagctctg gtactccaga ccccggcggg tggcatactt 31861 cctccacagg ctgaatggga ggtgggtggt ggtaagactg gaaccgcacc agacgtgcat 31921 cgcggtgggg ggtctcatct ctgctctctt gcagatgaag cgggcgcggg tggaagtgga

Figure 9 (continued)

31981 aggggacttc aaccccgtgt atccctttga taaggatgac gaacaggaca atcaagacgt 32041 caacagcacc ctcccaccct tcctctcctc caatgggctc actgaatccc cggcggggtt 32101 cctcgccctg aaaacttcca accccatgga tttcactgac aaaggcgcac tcacagtcaa 32161 aaccaatccc cccatagagg tcaattcaag tggacagctc agtctcaaat taggatctgg 32221 tctcacagtc tctggggggg cactgcaggc catgggtgag accgtctcag tcacagctcc 32281 catcaccaag actaatggaa acataggctt acaactggcc agtaacccag gcctgcaagt 32341 cagtaatggt ttaaagctta aagtcacagc accattcacc ctcaataata atggtctgaa 32401 cataggcgtg gacgcgccac tcagaataca agataacaaa cttcaattat ccacgggaaa 32461 tggcatagaa gttgccagta acagaacact ggctgttaaa cttaaaagaa caggaaacaa 32521 caatcaagga ttagactttg atggtgtaca gctagtctta aaattgggag atgggttgaa 32581 attaggcaac actgggtatg ttgacataag attaggaaat gccaataact gtggcttaca 32641 acttgaaaac ggggaattaa aattcaaaat gggggatgga ctgatttatg gcaacacagg 32701 atatgttgat gtcaacgttg ggcaaggtat agagattaat caaagaaagg ttaaagtgaa 32761 aacagcagaa ggcctagcct tcgacaacca aaataggtta aaaatcaagt gcaatacccc 32821 actaggattt gatggcactg gtaatttgaa agtgggttta ggagatggcc tctatatagc 32881 caatgataaa attttttatg aagctcccac actatggaca accgcatctc cacaaactaa 32941 tgccaatgtg agatctgaaa gcgataatca aacaactaaa aatgctaaag tgcagctgac 33001 cctatccaga tgtggagcca tggttctagg gtacatctca gtttatggca ctggagcccc 33061 cctcattccc atcaatacag gtactacgac taatttaaga ctattgctag cctttgatgg 33121 agagggtaga ttagttaatg gtaataacat gctgacgtcc tctttagaag tgaaggcagg 33181 agccacagtt aatgcatcat caggaataga caggagaatc tttatgccca ataaaggttc 33241 ctatctaaac tcaggctctg attcaggaca ggctcacaac gccatattta gaaaggtcta 33301 ccttaacaaa gacataaata aaacatgtga tctaactcta acattaaatg aaaacagagc 33361 aaatggacaa tattcattat actttaagtg gaccaacttc agcgccagtg ttaataatca 33421 aacctttttcc acctgtgtaa cccactttgt ctatctgggt gaaaatccat gaaaataaaa 33481 ccaaactatt ttaaacaaat caacttttta ttttattctg agaaaaagaa gaagcaccgc

Figure 9 (continued)

33541 caccacgctg gggtctctgg ggagagtaag gaacaaaggt aatcttcttc acgtgtttgg 33601 tgcggatccc cccaccgccc ggccacttcc acccgtacgt caccggtccc acgggaacca 33661 tcaccagtgg ggcgatgtgg ctctggcccc acaccttcac acagtcctgg tgggcgcaac 33721 gggaatcatc cagttgcaaa aagccctgag acacatggga cacatccaaa cagttcttaa 33781 gtctgggatc tgaggtcttc tccaccggct caggctgtgc tgctggcgct gctgccgtcg 33841 acggtgccgg gtcacggggc atctcaaaca aggggtcggg aatctgcagg atctgagcca 33901 gcatgtcggt gtctatctgc ggtgagaagg agggcggtac ggtcgcacgt tgcggcaccg 33961 gtcatacaca tcataactca gcgcccggga ccgccacatc acgctgtcaa acatccgctg 34021 gcgctgccgc tcggtccggc tcgccctcaa aggatgacgg gaaatactgt ccaattcccg 34081 caccgagcga gccagcaggc gccgcgtccg tctggcgcaa cacctgaacc tgatctcctc 34141 gcccgtgcgg cagtacgagc agaccagaac cagcatgttg ttcatcaccc cataatggaa 34201 agcagacagt ccaaaattca cagtcctgat caggtgctcg gcatgctcat cgtatctcac 34261 gttgatgtaa atcagatgca gtcccctcac atacacgctg cccacataca tcatctcctt 34321 gggcatatgg tcgttcaccc aggggcggta ccacgggatc ctcagattca ccaaggatcc 34381 caccaccaac agatagaacc atctcctcaa caacaccgcc cccgcccgac actgcagaga 34441 ccccgggcgg ctacagtgac aatgcaacat ccacacctcc gagcccctga tcatccgaca 34501 gtggacaatg accagcgtcg cgggacaagc acacacatgc atgtactgtc tcatgagatg 34561 ttgttcatac gggctcaaaa agaaatggaa cggagccggc cattccaagt acactgtaaa 34621 catcacactg gacgggaccg atcttaccgt gatcacatcg tgcagggtgt tggtgtcaca 34681 gcgccgggcg aaacattcac cttgggctgg gggatcgggg tccgggagag gtagctgatg 34741 ctgatgaaaa ggggccaagg ggcccggagg cggttgaggg ttccgttgat ccatgagatg 34801 acgaagaaga agaatacaag caggaatatt ccagttctcg ctgctgatcc agttgacggc 34861 gcaccagatt gtatttccga aagcaaaaga aggcccgctg ccaagccgca ggtgaaactc 34921 gccgggaggg tgaggtcacc ctctgcctct caaagtaggc ggcgtgagcc aacaactgac 34981 tcagcccggt caacagtcgc cactgatgac ctgtcaactc ccagcccgtg cgagagcaat 35041 aagcgatgag gtcatccacc aaagcgcgag tgccgcgaag ccagtccaaa gcagagtggc

Figure 9 (continued)

35101 ggtcgcgtac cagaggagga gcagggacgg cgggaagaaa aggcaccatg agaagagccc 35161 ccttactgct gaagcaggtc gtccaggatt tcaaactgga ggtcccgaag gtagcatctg 35221 cgtccccgc tgtgctgatg ataggtcacc gccagatcaa aatggacacg gttctccaag 35281 cccgacacca ccgcatccac caacgcagga agatgaagct tgagataaat caaaaatgtc 35341 accttctggg gattcagatc gttatcctcg aaacaataca tagaacactc atcgatctgc 35401 tgcaactcgt tctcctgctt ccagccatta acgatgcccg tcaggacatc atcaaacacc 35461 aaaattagca tggcggaaga gctgaacgag agcaatctcc acctccagac ggagacacaa 35521 gcggaccatg ggacggtgtg ggcggtgggg gcggcgacgt ttagtcgctg agcgcctcag 35581 gctcttcaga aacctgcaac agatccagaa ggccatcagg cacggtaatc tgctccaaat 35641 gagcctgcca ggtgatctgc tgctttaacg catcgagcag atcttccaac accgcctggg 35701 tctctggcgt ccctgaatct agctcctggg tccccacgca acacaaaagt ctcagctccg 35761 gctcccgctg cagcacgtgt acccccacgt aaacgttctg cctctccccg cgcatgtcta 35821 gaaaacatct ccaaaaaagc tcgaactctt gtttcaggag gcgtaacagg tcaaagccac 35881 gcccctccag gtaagacacc aggggagcgg gcgcttgcaa cagacaccac agaggacggt 35941 ggacagacgc catacctggg agaatacaag aagatcagag ctcagttatt tccaccactt 36001 gcggaaaact ggtgccctgt aagactagac gggccacggg ctccccgcg cggccgtgat 36061 agtcaaaggg cccattgttc accagcagat tttcaactcg gcctcgaggt tgcagggcac 36121 cagatcggcc tccacataca ggctgtgggt gctcacgttc cgctggagtg aagatagacg 36181 ccccacaaaa ccaacaggca cccgaacaga aggccggtat acaagagcga gcgacctccg 36241 gcatagacag taaaatctgt aagagcataa agatcatagc tgccggtgcc gggtcgctgc 36301 gtcggcaggt gcgcggtctc ctcgaggcgt tgcacaaaaa ggttcagacg ctgccgagaa 36361 gccatacagt aggaaaaaag tggccctcct taccgtctgc tcgctcgggc ggcagtcagc 36421 gagagaaaat ggcgatcgct gactccacac gcgagcccgg cgcaatatat agaccctaac 36481 ccctcccatc gcgtcagaga ccacaggtcg gtatgccctc gttaatggtt aacccgggaa 36541 ttactcggaa aattttccgc cgcacccgtc tgcgcgcgaa aacctgaact tccgcctccc 36601 gcgttcccac gtgacgtcac cgacttacaa catccacttc ccacacccgc gcacaaaatg

Figure 9 (continued)

36661 gctgccgtgg gaaccgcctc aaaactacag aatccccgaa aactaccaac atggccgccc 36721 cgcgccaaac acgccggaag tcccgcccca cacccctcaa cccccaatcc ccacactccg 36781 cgtttttcac cacaaccgga tgtaaatttg gacgtttttg aggtatatta ttgatgatgg 36841 gc

SEQUENCE LISTING

<160> NUMBER OF SEQ ID NOS: 45

<210> SEQ ID NO 1
<211> LENGTH: 36842
<212> TYPE: DNA
<213> ORGANISM: Titi Monkey Adenovirus

<400> SEQUENCE: 1
gcccatcatc aataatatac ctcaaaaacg tccaaattta catccggttg tggtgaaaaa 60
cgcggagtgt ggggattggg ggttgagggg tgtggggcgg gacttccggc gtgtttggcg 120
cggggcggcc atgttggtag ttttccgaga tttttccgtt ttgaggggtt ttggactaca 180
aatgaagcaa gatggcggct gggaggagcc aaaatggact ttgcccagag aaaatgacgt 240
catccgggga ttttccacgg attgggcggc agatttgcaa gtttttagac aaaattttta 300
cgcggaagtg aaacccgaaa attcagaagt tgacgtgaca ggtgtggttt tattgccggg 360
ccatttgacc tttgaccgcc acgtcgacag cgggccgggg aatttttttgt gctgacattt 420 ccgggtttcg gtgtcaaagt ccccgctggg caccgcggag tcagctgacc cgctgggtat 480
ttaatgccga gcgctcccgt caagaggcca ctcttgagtg caccgcgaga agagttttct 540
ccgagctccc gtctgaaccg tgggaaaaaa tgaagacttg gcagtgtcag tctctggccg 600
acctggagct ggtgcaggag atcctggacg agatgggaga aggtaaccac ggtcactttg 660
tgcccgagga cggtggggac ccgggggaca gcggcttcgt tccggaaccg ctttcgcttc 720
acgatctctt cgacgtgccg acggatcctc tgacccagga gcatgccgag gcggtagatc 780
tcttgttccc ggacccggtc gagcccgata gcacccagga ggatgttgac cgcccgctcc 840 gaacccccttc tccgcctcag ctttctcccg tgaatcttgt gtgtagacga gaacaagaac 900
tggaagagct cggggccgag atagatctca cctgtcacga gaagatgttt acagacagcg 960
aggacgaggg agaaggtgct cctcaaaatg gcggttccgg tgagcgagat ggcttccgtc 1020
tggattgtcc tgagcagccc ggtcagggtt gtttgtcttg tcacgtccat cgctgtacca 1080
tgggtgatcc caccttgatg tgttcgctgt gttacatgcg cttgaacagc cactgtatct 1140
acagtaagtg tttctcgctt ggggatgtgt gaagtgtctg gagtagggaa aaagctaggg 1200
gaattttcca ttcgagtgtg tctcattatt cttgttctta atgtgacagg tcctgtctct 1260
gagccagaag aagaggaggg agatgaaagt tcccgggaac ggccgcggcc ttccacgagt 1320
gctcaggggg tgactcagcg accacagaaa cgccaacatg cagatgtcct taccgaccct 1380
ccccagctgg gggcggtgtg cgccttgctg ggcccgcagg aggaaccttt ggacttgagc 1440

```
tgcaagcgtt cccgcccaga gtcataaaac cacagacact tgagattgtt tgttgaactc   1500

agggaggggt ggccggggtg agtcagtgtg tgcaataaac gacttgttgg aactggactc   1560

tgtcccggcg atgtttgttc agggctcaag tgggtgcggt ggggaggtat aaacatgggg   1620

cggccgggcg ggttgattca gagcgagagc ggcagccggg ctgagctttt ctctcaatgg   1680

atctcttgaa gttcctggaa gactttgaga attgcagaca agttttgcag caggcgtcca   1740

agaggactgg gggttggagc cgctggctgc ttggcaatca gctggttcgc acggtcgctc   1800

aggtcaagac agactatagc gagcatttcg agcagctttt gcaggagcag aaccgacttc   1860

tgctgaacaa cttggaactc ggtcacacca gggcactgaa cggtgtgctg agggaactgg   1920

actttgagaa tacgggacgg gtggtagctg gtcttgcttt cctcgcgtac ctgctcgatc   1980

ggtgggacga gaacagcgtc ctcagcccgg gctaccgcct cgattgcttg gccctcgcga   2040

tatggaagca cacgctgagg gaggggatcc tgagaggggt gatgcagggg ccccgggcgc   2100

gggtgaaccg ggagatcagg cgggaggtgg aggagcggct gacgcaggtg cagcgggagt   2160

tggaagagag ggagagggag aggcagcagc gggagaggga gcagcagcag caggaggggg   2220

aaatgactac gagcatatgg aggccttcca tggaggcgga gtggccgccg cgggcgggga   2280

tggacccccc gctggaggag cagtgggagg cggaccacga cccggaggca taattcagca   2340

ggtggctagg ttgtttcccg agctggccgg gcagttgcga gctcccttgc atcggcccgt   2400

gcctcgaccc ccaccgagga atgtggatga gcggcggggc atagtcagac cctgggatga   2460

ggccaatccc cagccagccg atgagcaagc gggcccctcg gaccgcacgc gatcttggat   2520

gatgagacgc cgtctggaga acattacttg gcaagaagtc tgggatgact tttgaggggg   2580

tgacatgttt ctgagggata gatacacgtt tgagcagatc cgcacgcact gggtggaccc   2640

ccacgaggat ctgggcctgg cgatcgctac ccattgcaag gtggctttgc atccagacag   2700

gacctatcgt gtgagggaca aaatatttat ccagaactgt tgctatgtca ttgggaacgg   2760

ggccacgatt atggtggaga cgagcgagcg ggtggctttc cagttgggaa tgcaacagat   2820

gagcccatcc atcacgggga tgtttggatg tacttttgta aactgtcgct tcagttgcga   2880

ccctaacgtg ttccgaggaa tttgcatcgc cgcgaacacg tcatttctgg tccacggttg   2940

tcatttcttt ggtttcccgg gagattgtat cgtggccaac gtgggtggtc gggtgcgggg   3000

cacgaccttc acttcttgct ttaaggggat ctataatccc gggcgccatg ctctgtcggt   3060

gagcaagtgc atctttgaca aatgtatgat agccatcagc accctgggct tttccaagat   3120

cagacacaat gtggccaccg agtgtttgtg ctttttactg tgccggggct tgggtcgcat   3180

ccagggcaac acggtgcacg ggccttacct gagctcccac cggatggtga cctgcgggga   3240

cgggaccatc cagaccctgc gtaccatcca catcgtggcc cacccgcgcc gcacctggcc   3300

cgtgtttgag cataacgtgc tgatgcgcac cagcatgtac ctgggcaacc ggcggggcat   3360

ctttatgccg cgccagagtc aggccttcca caccaacctg gtgctggacc agcatgcctc   3420

gacccaggtg tccatcagcg ggctgtatga catgagcctg cagatatatc ggacgctgcg   3480

cgtggacgag acccgcagtc ggctgatgca ttgcgagtgc ggcgagtctc acctggtgaa   3540

tggacacgtt ttgggaatct gtacggacga catgcgagtg gatccgctcc aatactcggc   3600

ggctcggacc gagtactctt cttcggagga tgaagcggac tgagtaagga agggttaagc   3660

cctgtggggt gggcggggtc tggtcggtgg cgggaagctg gcagggggcg tggtgggaaa   3720

aagagggggt tggagggcgt gggcggttat tattgccgcg gccatggcta gcaacgggag   3780

ctccacctcc tctggagtca gttttgacgg ggccgtgtac agcccatttc tgacgtgtcg   3840
```

```
cctgcccact tgggcgggag tccgtcagaa tgtcatcggg tccaccatcg atgggagccc   3900
ggtgcttcct actaacgcat cttccatgcg ttatgagaca gttagcgcga cgggcggcca   3960
ggcaactctg cctatttcta gcttcgggac tcgtgttcta cctgcagatc ctgcagcacg   4020
cttctcgacg atccagaccc ccgcggcagc ctacgcggcg gcagcggcgg ctcgcaacgc   4080
agacttcgaa gaacgcatcg tcgcgggact gacggatctg gcggagaaga ttaacctgct   4140
gaacgtgcgc caggagatgg acgagcgcgc cttggacacc gtgggagccg acatcgtgca   4200
gctgaagcag ggcttggaat tcttcgcgca gcgtgtggag gccctgaccg ggctgtgac    4260
tcagctccag gaacaggtcc aacagctgca agaggccgcc agcgccgcgg ctgtcgtcat   4320
tcccgccact cctgcttctc cccagcctgt ggttccacca gcagctgctg ccgaggttgt   4380
gccgctgccc gtcacccccc ctgattcccc gcatgcagcc gcccccaccg ctccacagcc   4440
tgccgagacc cccgtggctg cacccctcac ctctcccgct tcccccgccc ccgctctcaa   4500
ccctgctgtg taatcaataa agaggcacga gatgcttttt gaatctgaat cacgtgttgg   4560
tttttattgc tgttgggggg agggtagggc tttgcgggcg tggtaggctc ggacccagcg   4620
gttgcggtcg gtgagggtgc gatggatctt ttccaggact cggtagagat gggtctgcac   4680
gttgaggtac atgggcatga ggccttcgcg gggatgcagg tagagccatt ggagggcctc   4740
gtgctcgggg gtggtgttgt agatgatcca gtcgtactgg gaggtctggg cgtggtggga   4800
gaagatgtct ttgagaagca tgctgatggc cacggggagc cccttggtgt aggtgttgat   4860
gaagcgggag agctgggagg gatgcatgcg gggctgatg agatgcatct tggcctggat    4920
cttgagattg gcgatgttgc cgcccaggtc tcgacggggg ttcatgttgt gcaggacgac   4980
gaggacggtg tagccggtgc acttggggaa cttgtcatgc aacttggaag ggaaggcgtg   5040
gaagaatttg gcgacgcctt tgtgaccgcc gaggttctcc atgcattcgt ccatgatgat   5100
ggcgatgggt ccccgggcgg cggcgcgggc gaaggcgttg cgggggtcgg tgacgtcata   5160
gttgtggtct tgggtgagct cgtcgtagga cattttgatg aatttggggg tgagggtccc   5220
cgattggggg atgagggtgc cttcgggccc gggggcgtag ttgccttcga agatttgcat   5280
ctcccaggct ttgatctcgg aggggggat catgtcgacc tgggggggcga tgaagaagac  5340
ggtctcgggg gcgggctgga tgagctgggt ggacatgagg ttgcggagga gctgtgactt   5400
gccgcagccg gtgggaccgt agatgacccc gatgacgggt tgcatgttgt aattgagcga   5460
gcggcaggtg ccgtccgcgg ggttgaggta gggcatgacc gagttgagca tgtctcgcat   5520
gatgaggttt tcttggacga gatcctggag cagcttggaa ccgccgaggg agaggagttc   5580
ttggaaggac tggaagttct tgagtggttt caggccgtcg gccagcgaca tcttggcgag   5640
tgagtcagcg agggtttggg ttttttccca gatctcgcgg acgtgttcta gggcatctcg   5700
atccagcagg tttcttggtt tcttgggttg ggatggctgt tggagtaggg ccggagccga   5760
tgcatctccc cgggggtgag cggggccagg gtccggtctt tccagggtct gagggtcctc   5820
cggagggtgg tttcggtgac ggtgaagggg tgggcttgag cttgcacgct ggcgagcgag   5880
cgcttgaggg tgaggcgact ggtctcgtag cgggcgtttc cgccttggta ttcctcgaga   5940
taacaattga gcaagagttg gtaggagagt tctgaggcgg ggtgtccctt ggctcggagc   6000
ttgcctttgc cctcgtgacc gcactggggg cagcggaggg atttgagggc gtagagtttg   6060
ggggcgagga agacggactc tgggctgtag gcgtcggcgc cgcacttgct acactgggtc   6120
tcgcattcga cgagccaggt gagctgggga tgctgggggt caaagactag gcctccgcca   6180
tttttcttga tgcgatgctt acctcgggtt tccatgagtc gatggccgcg ttcggtgacg   6240
```

```
aagagggagt cggtgtctcc gtagacagat ttcaggggtc gcaggtggag gggggtgccg   6300
cggtcctcgt cgtagaggaa gccggcccac tcggagacga aggctctggt ccaggcgagg   6360
acgaagctgg caatgtgcga ggggtagcgt tcgttctcga tcaaggggtc gttcttttcc   6420
agggtgtgga gacagagcgc gtcctcgtcg cagtccagga aggtgattgg cttgtaagtg   6480
taggtcacgt gatctgggtc cccgggggtc ggctgcgggg gggtataaaa gggggcgtgt   6540
tctgggggt cctcattgtc ctcctcggga tcgctaccgc tgccggcgac gaccgtgggc   6600
tcttgcagcg ccagctgtcc aggtaagaat tctgccgccc aggcgtccat gtattcagaa   6660
ctgaggttgt cagtttcaat gaaggaggag gatttgatgg aatagtgccc cgaggccacg   6720
cccttgacga gggccccctc catctggtca gaaaacaccg tctttttatt gtccagcttg   6780
gtggcgaagg agccatagag ggcgttggag agcaatttgg cgatggagcg gagcgtttgg   6840
tttttgtcgc gatcggcgcg ttccttggcg gcgatgttga gttgcacgta ctcgcgggcg   6900
acacagcgcc actcggggaa gacggtggcc cgctcgtcgg gttgcaagcg cacgcgccag   6960
ccgcggttgt gcagggtcat gacgtcgatg ctggtggcca cctcgccgcg caggctctcg   7020
ttggtccagc agagacggcc gcccttgcgc gagcagaagg ggggcaggac gtcgagcatg   7080
tcctcgggcg gggggtcggc gtcgatggtg aagatgccgg gcagcaggtc ggggtcaaag   7140
tagtccaggg gcgtgtcgcg gcggtcgagc cgttgctgcc aggcgtgcag ggccagggcc   7200
cgctcgtagg ggttgagggg cgccccccgcg gggaagggat gggtgagggc ggaggcgtac   7260
atgccgcaga tgtcgtagac gtagaggggc tcctcgagga cgccgatgaa ggtggggtag   7320
cagcgccccc cgcggatgct ggcgcggacg tagtcataca actcgtggga gggggcgagg   7380
aggacggagc cgaggtgggg tttctggggg cgctcggctc ggtagaccac ctggcggaag   7440
atggcgtggg agttggagga gatggtgggc cgttggaaga tgttgaaggc gcagaggggg   7500
aggttgacgg actcgtggac gaagcgggcg taggagtctt gcaagcggag gacgagctcg   7560
gcggtgacga ggacgtcgag ggcgcagtag tcgagggtct gcttgacgag atcgtagcgc   7620
tcatcgtggg tctttttgct ttgcagccac agctccttgt tgaggcgata ctcttcggag   7680
tccttccaat acccttcgtc ggggaatcca tcgctgtctg tccggtaagt gcctttcatg   7740
tagaactcgt tgacggcctg gtaggggcag cagcccttct ccacggagag ctcgtaggcc   7800
tgggcggcct tgcgaagaga ggtgtgggtg agggcgaagg tgtcgcggac catgaatttg   7860
agggattggc acttgaaatc ggcgtccccg cagcccccct gctcccagag ggcgtagtcg   7920
gtgccccccct ctttgctgta ctgggggttg ggcagggcga aggtgatgtc gttgaagagg   7980
atcttgccgc agcggggcat gaagttgcga gtgacccgga agggcggggg gatctcgccg   8040
cggtggttga ccacctgggc ggccatgacg atctcgtcga agccgctgat gttgtggccg   8100
atgatgtaaa tttcccagaa gcggggtcgg ccctggaatt tgaggctttt gaagtgttcg   8160
ggttgcaagt cgtctgggga ggagagccct tccttggcgg cgaggtcgtg caggagttgg   8220
aagttttcca gtttgaagag tcgccagagc tggcgggcaa agtgttgctg cagggagtcg   8280
cggaactctt tgaagcggca gccgatggct ttgggctggg gggtgagcag gtagaagacc   8340
cgggggtggg tgagggaccg ccagacttgc cagccctggt cacgtgctag ctgctgggcc   8400
tcggcggcca tctgctcgtc gccgccgata tgcatgacga gcatgaaggg catgagctgc   8460
ttgccgaagc ggttgatgct ggtgtaggtt tccacgtcgt aggtgacaaa gagccgacgg   8520
gtgtctgggt gggccccgag gggggaagaac ttgatctcct gccaccagtg cgaggagtgg   8580
gcttgcacgt gatggaagta gaagtcgcgg cggcggacgg agcaggtgtg ggtctgcttg   8640
```

```
tagtagcgcc cgcagaattc acattttctg ttctgagatg agcgagtgga tgaggtagag   8700
ttggtgttgg cggacgagga agtgcagggg gaagggcagg agatgatgct cgtcgaggtc   8760
ggggacgggg gccacttggg cctgggcccg tccgggttcc acgcgccaga tctcggaggc   8820
ggtgggccgg agctcttgca tcttggagat gagggtgtgc acgtggaggt cttggaaaaa   8880
tgcgtcggga ggctcgtcgc agagatgcac gcgacagagg gtgcggatgg gcgcggcgag   8940
atgcccggcg acgccatagt acttgatttc ggtgggcacg ccggagcggg ggtcgatgac   9000
gtgcagggac ttggtaccgc gggggcgagg acgttgccgc gcagcgggtt gagggggact   9060
actcgggggg tggcagctcg acgtcggcgg cgttgagcgg gggcagggcg agatgcctgg   9120
cccggagact ggaggcgtag tcgatgactc ggcggttcat gcgttggatc tggggtctct   9180
gggtgaagac caccggtccc gtggttttga acctgaaaga caattcgaca gaatcaatct   9240
cggcatcgtt gacggcggcc tgcctgagga tttcgctgac gtcgccggag ttgtcttggt   9300
aggcgatctc ggccatgaac tgctcgactt cctcctcctc gagttccccg tgtccggcgc   9360
gttcgacggt ggcggcgagg tcgttgctga tgcgcccgat gagttgttgg aaggcgttga   9420
ggccgttctc gttccagacg cgcgagtaga ccacgtctcc gtggacgtcg cgggcgcgca   9480
tgaccacctg ggcgaggttg agctccacgt ggcgggcgca gacggggtag ttgcgcagcc   9540
gctggtagag gtaattgagg gtggtggcgg cgtgctcggt gacgaagaag tacatgaccc   9600
agcgccggag ggtgagttcg ttgatgtcgc cgagggcctc gagccgttgc atggcctcgt   9660
agaagtccac ggcgaagttg aagaactggc tgttgcgcgc cgagaccgtg agctcttctt   9720
ccaagagccg gatgagttcg gccaccgtgg cccrgacctc gcggacgaaa gcttcgggtt   9780
cctcttcctc ctcctcttct tcttccaaga tttcttcttc ttcctctacc aactcgggga   9840
tctctgccgg gggtgctaac tcctcttctt ctacagccgc cgctggtgga acagcagcag   9900
caggggcgc tcgacgacga cggcggcgga tgggcagacg gtccacgaac cgttctatca   9960
tctctccgcg gcgacggcgc atggtttcgg tgacgggcac tccgtcttcg cgggggcgca  10020
ggatgaaagt gccggcgtag cgcgtgcgcc tcccggcggt gggccgacgc ctgagcccgg  10080
gccgtgcccc gccttccaag tcatggcggc ggcggtcggg gttgggcagc gacagggcat  10140
tgacgatgca tctgattaaa ttttgtgtag tgagaccagc gtgggatctc aagagctgca  10200
gatcgacggg atctgagaag cgttgaacga aagcttcgag ccaatcgcaa tcgcaaggta  10260
ggctgagcac cgtgctcatc gtgggggtcc cgcctgatgg aggaaggcct tcttggttct  10320
gtccccccag aggttccgca gaggaagagg aggggggcgg gggttgttgc agcgagagca  10380
ggtagttgaa gtaggccgac ttgagacggc ggatggcggc gaggatgacc aggtccttcc  10440
ttccggcttg ctggacgcgc aatctgtcgg ccatgcccca ggcttgatct tgacacacgc  10500
cgaggtcctt gtagaagtct tgcaggagtc tctcgacggg cacgtcttcg gcctgcccac  10560
cttccatgtg ggtgcggccc agcccgcgca ggggctcgat gagggcgagg tcggccacga  10620
ccctttcgct gaggatggcc tgttggatgc tggcgagggt gccttggaag tcgtcgaggt  10680
ccacgaagcg gtggtaggcg ccggtgttga tggcgtagga gcagttggcc atgagggacc  10740
agttgacggt ctgcgagccg gcgtgcacct gttcgcggta cttgaggcgg ctgtaggccc  10800
tggagtcgaa gacgtagtcg ttgcagacgc gcacgaggta ctggtagccc acgaggaagt  10860
ggggcggcgg caggttgtaa cagggccagt gccgggtggc ggcggcgcgc ggggcgaggt  10920
tggccagcat gaggcggtgg tagtggtaga cgtagcgcga catccaagtg atcccggtgg  10980
cggtggkgct ggcccgcgtg ractcccggg cgcggttcca gatgttgcgc agcggtcgga  11040
```

```
agtattccat ggtcggcacg gtctgaccgg tgagccgggc gcagtcgggg atgctctgcg  11100
aatggaggag atatagaatc ttaggcccca ttctgctggt gtgttctttg gcagatgcat  11160
ccggtgctac gtcagatgaa accgccggcg acggcgaccg cctcgtaccc acccccgccc  11220
accacggccc aggcggcggt agctagtgga gccggcgcgg cagcagcagg aggaggagag  11280
ctgacggggg gtcgccgcgt gcccgagggt cttttggacg agggcgaggg tctggcgcgt  11340
ctgggggcgc acgaccccga gcggcacccc cgcgtgcagc tgaagcggga cacgcgcgag  11400
gcgtacgtgc cgcgacgcaa cgcgttcagg gagcgtgagg gccaggaacc cgaggagatg  11460
agggatttga ggtttcgggc cggtcgggag ttgcatgatc tggatcgcga gcgggtgctg  11520
cgatcggagg atttcgaggt ggacccgcgg acgggcgtga gtcccgcgcg ggcgcacgtg  11580
gaggcggcca acctggtgag cgcgtacgag gagacggtga agcaggagat gaactttcag  11640
aagagtttca acaaccacgt gcgcacgttg atcgcgcgcg aggaggtggc catcgggctg  11700
atgcatctgt gggactttgt ggaggcgttc gtgagcaacc ccaacagcaa gcctctgacg  11760
gcgcagctgc tgctgatcgt gcaacattcg cgggacaacg aggtgtttag ggaggcgctg  11820
ctgaacatcg ccgagcccga gggtcgctgg ctgctggacc tgatcaacat cctgcagagt  11880
atcgtggtgc aggagcgttc gctgagtctc ggggagaagg tggccgccat caattatagc  11940
atgttgagtc tgggcaaaca ctacgcccgc aagatttaca agagcccctt cgtgcccatc  12000
gacaaggagg tgaagatcga tagcttttac atgcgcatgg ccctgaaggt gctgacgctg  12060
agcgacgacc tgggcgtcta ccgcaacgac cgcatccaca aggccgtgag cgccagtcgc  12120
cggcgcgagc tcagcgaccg cgagctgatg cactgcttgc atcgggcgct gacctcccac  12180
ggcgacgagc gtctggaggc cgaggagttg ctggccggct cgggcgctct ccgcagtgct  12240
gaaaggcagg agcccagcta ctttgacgcc ggggcggatc tgcgatggca gccgagtcac  12300
cgggccgcgg ccgccgccat ggccctgagc cgctacggtc cgcccgaggc cgaggaggag  12360
gaggcaggct atgaggagta tgatgactac gaggacgaag acgggctcat ggactagaat  12420
tttttgtta gggcaggaag cgagcaagat ggaccccaac ccaccaccac cacgtcagct  12480
gaaccccgag gcccgggcgg tcgtgcagag ccagccttcg gcgcccaccg cctccgacga  12540
ctgggatggc atgatgcagc ggatcatggc gctgacggcg cgcaatcccg acgcgttccg  12600
gcagcagcct caggccaacc gattcgcggc catcttggaa gccgtggtgc cctcgcgccc  12660
cgaccccacc cacgaaaagg tcttggccat cgtcaacgcc ctggcggacg cgggggccat  12720
ccgtcccgac gagggtgggc agatctacag cgccctcttg cagcgcgtgg cccgttacaa  12780
cagcaccaac gtgcagacca atctggaccg cctggtcacg gacgtgaagg aggcggtggc  12840
ccagcgcgag cgttatttca aggagggcaa tctcgggtcc ctggtggccc tgaacgcctt  12900
catcggctcg ctgccggcca acgtggtccg cgggcaggag gactacacgg ctttcatcag  12960
cgcgctgcgg ttgatggtgg ccgaggtgcc ccagagcgag gtctaccagt cgggacccca  13020
atactttttc cagaccagtc gtcagggctt gcagacggtt aatctgacgc gggcctttga  13080
gaacttgcat cagttgtggg gcgtcaaggc ccccgtgggc agcgaccgct cgaccatctc  13140
gtccctgctg acccccaaca cgcgcctgct gctcttgctc atcgccccct tcacggacag  13200
cgggctgatc tcccgcgaca cttacatcgg ccatctgctg accctgtacc gggaggccat  13260
cggccagaac cgggtggatg aaagcacttt ccaggagatc acgagcgtga gccgggccct  13320
gggccaggag gaccccggca gcttggaggc cacgttgaac tttttgctga ccaacaagcg  13380
gcagcgtatc cccacccagt acgccctgaa cacggaggag gagcgcatct tgcgctacgt  13440
```

```
gcagcagtcg gtgtccctgt atctgatgcg cgaggggggcg agtcccaccg ccgcgctgga  13500
cctgacggct gccaatctgg agcccagctt ctacgccagc aaccgggcct tcatcaaccg  13560
cctgatggac tacttgcatc gggcggcggc cattaatccc gattacttta ccaacgccat  13620
tctgaacccc cactggttgc cccctcaggg ctttttcacg gggggagtttg acctgcccga  13680
ggccaacgat ggctttttgt gggacgatat cgacagcagt ctggtggcca agaaggaggg  13740
cggtgacgag cagagccggc gcacgagcct ggcagacctg gggggcggcta gcagcttccc  13800
cagcttgggc tcgttgtttg agagtagcag cagttcagct agcagcagca gacgcccgag  13860
ttctagtacg gggcgggtga cgcggccgcg gctgccgggg gaggacgagt acctgcgcga  13920
ccccctgttg ctgcccagtc gggacaagaa ctttcccaac aacggggtgg agaccctggt  13980
ggataagctg cggcgttgga agacctacgc ccaggagcag cgcgagttga ctcagggcgc  14040
gcggccccgg gaccctcggg atgactcagc gtggcatcag catcggcgcc agcgggagta  14100
tgacgaggac gcggctagcg acagcagcgt gttggatctg ggcgggagcg ggaacccctt  14160
cgcccacctg atgccccgcg gcgggagtcg gcgtctgtaa gcccgcacgc ggtgtgtggc  14220
acgtgcaaaa aagaaaaata aaaaaacacg agtacttacc aaggccatga cggagccgcg  14280
ttgttgtgtc tctctcctct cctctttttt cttctttctc tatctgatcg gcggtgtggc  14340
ggtggcggcg tagaagatgc aacgcagtgt gccggtgccc gcgagcccac ctccgtctta  14400
tgaggaggcg atggcgtcag tgggggcggt gcttcctccg ccggtgatgc aggctccgta  14460
cgtgcctccg cgctacctgg ggccgacaga ggggcggaac agcatccgtt actctgagat  14520
gcaggcgctg tacgacacga cgcggctgta cctggtggac aacaagtccg ccgatatcgc  14580
gtccctgaac taccagaacg accacagtag tttcttgacg agcgtggtgc agaacagcga  14640
ctttagccct caggaggcga gcacgcagac ggtgaatctg gacgagcgct cgcgctgggg  14700
cggggagctc aagaccatcc tgcacacgtg catgcccaac gtcaacgagt tcatgttcag  14760
caacagcttc cgggcgaggc tgatgactca gaaaaagaat ggggtggccg agtacaagtg  14820
ggtggagctg accatccccg agggcaattt cagtgagatc atgaccctgg acctgatgaa  14880
taacgcggtg gtggagcact atttgcaagt ggggcgtcag aacggggtgg aggaggcgga  14940
catcggggtg aagtttgaca cacgcaactt ccgcctgggg tacgacccgg tgacgaagct  15000
ggtgacgccg ggcagctata cgtacgaggc ctttcatccc gacatcattt tgctgcccgg  15060
gtgcgcggtg gactttacct acagccgcct gagcaacctg ctgggcatcc gcaagcggca  15120
gcccttccag gagggtttca tcatcgagta cgatgacctg gtggggggca acatcccggc  15180
tctcctcgac gtggcggcct atgaaggtag tctgcagggt ggcggtggca gcggcggcgg  15240
atcgaccacc gcggccgaga cgcgagacgg gcctgctgaa gacgctgacg gccccgtcct  15300
cgtggacgct gatgacgtgg agtacgagat gcgcggcgat ggtcacatgg tccgcaagag  15360
gcgtagcgcc tcacctgtgg cggagcctgc ggcagatcct atccctaaca gccccgttat  15420
caaaccaatt acaaaagact caaaaaaccg aacctaccat gtagacgagg taaccaacca  15480
gacggcctac cgcagctggt acctggccta caactacggg gacccggaga agggcgtgcg  15540
ctcgtggacg ctgctgacga cgcccgacgt cacgtgcggc tcggagcagg tctactggtc  15600
gctgcccgac atgatggtgg accccgtgac cttccgcccc tcgcagtcgc ccagcaacta  15660
cccggtggtg ggcgccgagc tcatgcccgt gcagtcgcgc acctttttca acgaccaggc  15720
cgtctactcg cagctcatcc gccagaacac ctccaagacg cacgtcttca accgcttccc  15780
cgacaaccag atcctcgtca ggcccccgc gcccaccatc accgccgtca gcgaaaacgt  15840
```

-continued

```
gcccgcgcac accaaccacg gcacgctggc catgcgtcac agcctgcgcg gcgtgcagcg  15900
ggtcaccgtc accgacgcca ggcggcgcac ctgtccctac atctacaaga ccttgggcat  15960
tgtcaccccg cgggtcctct ccagtcgcac cttttaagca tgtccttctc cctcctccat  16020
cctcagcgcg cgcgcggatg tccattctca tctctcccag caacaacacc gggtggggct  16080
tagggaccaa caaaatgtac ggaggagcca agcgccggtc cagcgaatac cccgtgctcg  16140
tcagacgcca tttcagggcc ccctggggag cccgcaaggg acgcctacgt cagcgcacca  16200
ccgtagatga cgtcatcgac agtgtggtcg acgacgcccg cgcctgggcg gatgctcagc  16260
cggcccccgc ggccgtggct gccgccgtgg gtcgtcgggt ggccagacgg gcccgtcgcc  16320
ggccccgggc cagcgcccgc tccaccgtgg acgcggtcat cgatagcgta gtcaggggcg  16380
cgaggcggta cgccgatcgc aaggcccgtc gcgggcgtcg cagcgccgcc gtgtcggccg  16440
ccaggaggct ggtgcgcgga gcccaccgcg tgtaccgccg caagctgcgg cgacgggaca  16500
gtcgacggag gggggccgcc cgggccgcgg ccgctgccat cagaagcatg gcgccgcgcc  16560
ggcgcaacgt gtactgggtc cgggacgcca cgaccggcac ccgggtcccc gtgtattccc  16620
gccccaagta aatttaataa aaattacacc tgattgcacc tcctagctcg cctccgcctt  16680
ttccatccat ccaaccaaca acatgaccac gcgaaagatc aaagaagagc tgctgcaggc  16740
ggtggcgccg gaggtgtaca cgccgctggt ggtgcccaag cgggagatta agagggagtt  16800
gaaaagggag atcaagggcg agctcaagcg ggagcggggg gacgttaagc cctttagaag  16860
caggaagcgc aagaaggacg aggacggcga cgtcctgcta gtgggcgccc ccggcaccga  16920
gggggtggag tttgtcaggg agtttgcccc gcggcgacga gtgcagtgga agggacgcaa  16980
ggtgaggcct ttcttgcggc cgggcgcggt cgtgcagttc accccgggcg agcggtccac  17040
atggcgcctg cacaagcgga gctacgacga ggtgcacacg gacgaagaca tcctgcaaca  17100
ggcggcggcg ttggacaacg agttccgcta cggcaaaaga ccccgaccct acgaggatct  17160
catgatcccg ctggacgagg gcaaccccac gcccagcctc aagcccgtca ccctgcaaca  17220
agtgctgccc gtctccacca ccacggaccg caaacgcgga gtcaaacgcg agcggctggg  17280
cgacctgcag cccaccgtgc agctcatggt gcccaagcgc cgcaagatgg aagacatgct  17340
cgaagacgcc ttcatggacc ccgcggagcc ccccgaggtc aagatccgac ccatcaaggc  17400
ggtggcgccc ggcatcggcg tgcagaccgt ggacgtggag atccccctgc gacaggcggc  17460
cgccgccgtc gccgacgtgg acatgggccc cagcgtgcaa gaagtgggca cggaccccat  17520
tccccagccg ccggccccgg tgtcctccct gatcccgatg ggagcggccg tggcagcggc  17580
ttccaagacg gtctcggcgg ggacgcagac ggacccctgg atgggggcgc ccgtgcagcc  17640
cgcccggcgc cgtcgccgct acccgaccgc cagctcggtg atgcccaact acttgttgca  17700
tccgtccatc accccgacgc ccggctaccg gggtcgacgg gcccctcgcc ggcgcgccgc  17760
cgcctcgtct tcctaccgca gccggaggag acccgcttcg cgccggagcc gcgcggtgac  17820
ccgagtggtg acccgccgcg ggaggcgcct gactctgccc gccgtgcgct accatccgtc  17880
gatcgtcttg taagcttttc cactgctcct accttgcagc tgcgcagcga acatggcttc  17940
caaaatgacg tgccgaatcc gcatccccgt gccctaccac ccgtcgagac ggcggaggag  18000
aggcggactg agcgggagcg gcctgggtgg tggcgcccgg cggctgaggc gacgacgggc  18060
cgtgcgcgga cacatgcgag gggctttttt gcaggccctg atccccatca tcgccgcggc  18120
cgtgggcacc atcccgggca tcgcgtcggt ggccttgcag gcttcgcggc gcaactaggt  18180
tgcttgttcc tcctcctcat caccatggtc tctctgctcc tcctgctgat ctcgtcgccg  18240
```

```
cctctgccgc cgccaccaac gttgccgctg tcggacttca ccaggacact ccatcaccgg  18300
cgcttcgagg atggaagata tcaatttttc ttccctggcc ccgcggcaag gctcgcgtcc  18360
cctgatgggc gcgtggggtg agatcgggac gaaccagatg aacggcgggg ccttcaactg  18420
gggcagcatc tggagcgggc tgaagagttt cggctccacg gtgaaaaatt acggtagcaa  18480
ggcgtggaac agcaccaccg ggcagatgct tcgcgacaag cttaaggaca cgggggtgcg  18540
ggaaaagatc gtggagggcg tcacctcggg catccacggg gcgctggatc tggcgcgcca  18600
ggagatggag aagcatatca actcccgcct ggaccatccg cgtcccgacg tggaggtcga  18660
ggagatgctg ccgggcttga acgagaagcc cccctggcc ccgtcggcgc ctcccaagga  18720
ggaccgtctg cccgagaagc gtccccggcc cgaggctgag gaggagctgg tgatccgcac  18780
ggacgagaag ccccccagct acgaggagat ctttggcaag gacatggcgc ccccgccccc  18840
ggtggcctcc acgtacccca tgacgaagcc gatcgccccc ctggcgcggc cggtgatcgg  18900
gacgtcttct agcaacaaga aagtgccccc tccgcgtcct ccaccgccca cgagacgtcc  18960
caccgtcccg gccgtggccc ccgcgggtcc cgtggatgtt ccggtgacct tggatcttcc  19020
gccgccgccg tctgccgtgg tgactccggc tgctccgcct gtggccatcg cgaccccccgc  19080
caccccggcc gcccgtccct cgtactctcg ccccagccgc cagagttggc agtcgaccct  19140
gagcagcatc acgggtctgg gagttaggag cctgaaacgc cgccgctgtt actaagcaat  19200
ccttcaatac aaccacgact ctgctttacc atgaacacct gtccgctgtt gttttttcat  19260
cgtcgttgcc gtcgccgccg cctccgtcat cgtcgtcgtc tggtctgctg cgcgcgtgtg  19320
acgtcaccat catcaggaag taggaagcta cctccactac acagcctgcg aagatggcga  19380
ccccctcgat gatgccgcaa tggtcttaca tgcacatcgc cggtcaggat gctacggagt  19440
acctgagtcc gggtctggtg cagtttgccc gggcgacgga aagctacttt tctctgggca  19500
acaagttcag gaacccgacg gtggctccga cccacgatgt gaccacggac cgttcccagc  19560
gtctgacgct gcgcttcgtg cccgtggaca aggaggacac cgtgtactcc cacaagtgcc  19620
gcttcaccct ggcggtgggc gacaaccgcg tgctggacat ggccagcact tactttgaca  19680
tccgcgggry mmtcgaccgg gggcccagct tcaaacccta cagcggcacc gcctacaact  19740
gcctcgcccc caagggcgct cccaacaatt gccagtggat gaccacagga gaaaacccta  19800
aaaccagaac atatggccag gcgccatttg aaacagattt cattaaccaa aataacaaca  19860
taggtgttca ggttggttgg acaacagctg aagttcccca accaataata gccgactcca  19920
aataccaacc agaaccacag tctggacaaa atcaatggca gtcagctgta acatcaacgg  19980
ttactgaatt ttctggcaga gttctgaaac cagatactcc tcaacttcca tgctatggtt  20040
cttatgctag acccactaat gattatgggg gtcagtgcag ggaaggtcaa caggtggatc  20100
aagtgtattt caatgttgaa aatcaagtca atgctcctaa agtcattctg tactctgaaa  20160
atgttaacat agaatcgcca gacactcata ttatctttca ccctacaccc aacggtacac  20220
atccaaatgc attggaagat atgttaggac aacaggcctc tcccaataga cccaattaca  20280
ttggtttcag agacaatttc attgggttta tgtactacaa cagcactggc aatcttgggg  20340
tcctggcggg gcaggcgtct cagctcaacg ctgtggtgga cttacaagac agaaacactg  20400
agctgtcgta ccaactgatg cttgatgcgc tgagtgatag aacgcggtac tttgcaatgt  20460
ggaatcaggc tgtggacagt tatgatcccg acgtgaggat cattgaaaac catggttgtg  20520
aagatgaaat gcccaactat tgcttccctc tgggcggggt tggtccaata gagaagtgga  20580
ttggtttaaa aatcaacaaa accgccaatc cagctacttt cagtcaagac aatgaaatat  20640
```

```
ctacggacaa tagaattggt actggtaaca tcaatgccat ggagatcaac atccaggcga  20700
atctgtggcg gagtttcttg tattccaacg tggccctcta cctgcccgac tcatacaaga  20760
tcacccccga taacgtggcc atctctgaca atgaaaattc atacgattac atgaacgggc  20820
gcatcgcccc cgtaggtctg atcgattact tcatagatat cggggcccgg tggtcgccca  20880
accccatgga caacgtcaac cccttcaacc accaccgcaa cgcggggctg cgctaccgtt  20940
cccagatcct gggcaacggc cgatacgtac ccttccacat ccaagtgccc caaaagttct  21000
ttgccatcaa aaacctcctc ctgctgcccg ggtcctacac ctacgagtgg accttccgca  21060
aggacgtcaa catgatcctg cagagcacgc tgggcaatga cctgcgagtg gatggcgcca  21120
aggtcagcat cgacagcgtc aacctctacg ccaacttctt ccccatggcc cacaacaccg  21180
cttccaccct ggaagccatg ctccgcaacg acaccaatga ccaaaacttc aacgactacc  21240
tcagcggagc caacatgctc taccctatcc cggccaacgc caccaacgtg cccatctcca  21300
tcccctcgag aaactgggcc gccttccgag gctggagctt cacccgcatc aaggccaagg  21360
aaacccccctc catcggggcc ggtttcgacc cctatttcaa ctactcgggc accattccct  21420
acctcgatgg caccttctac ctcaaccaca ccttccgccg cgtctccatc atgtatgact  21480
cctccgtcag ctggccgggc aacgaccgcc tgctcacgcc caacgagttt gaaatcaaac  21540
gggccgtgga cggagagggc tacaccgtct gccagagtaa catgaccaag gactggttcc  21600
tcatccagat gttgagccac tacaacatcg gataccaggg cttcttcgcc cccgagtcct  21660
acaaggaccg gctgtactcc ttcttccgca acttccagcc catgagcagg caggtggtcg  21720
accccatcaa ctacaaggac tacaagaagg tcaccgtgcg ctaccagcac aacaacacgg  21780
gcttcacggg cgatgtcacc cccgcggcca tccgggaggg acacgcctac cccgccaacg  21840
cccccctaccc cctcatcggg gccaccgcgg tgccctcgct cacccagaaa aagttcctct  21900
gcgaccgcgt catgtggcgc atccccttct cctccaactt catgtccatg ggcgccctca  21960
ccgacctggg gcagaacatg ctctacgcca actcggccca cgccctggac atgaccttcg  22020
aggtcgaccc catggacgag cccaccctgc tgtatgtctt gtttgaagtc tttgacgtgg  22080
tccgcgtgca ccaacctcac aggggcgtca tcgaggccgt ctacctgcgt accccattct  22140
cggctggtaa cgccaccaca taaacaactg ctgactgatg ggttccagcg aagaggagct  22200
caaagccatc gcgcgagatc tgggctgcgg gccctctttc ttgggcactt tcgataaacg  22260
ttttcccggt ttcatctccc cccacaagct cgcctgcgcc atcgtcaaca ccgcgggccg  22320
agagaccggg ggcgtgcact ggctcgcgct gggatggaac cccaaatcca agacggtcta  22380
cctgttcgac cccttcggct tttcagatca gaggctcatg caaatctatc agttccagta  22440
cgagagcctc ctcaaacgca gcgccctggc cagtaccgag gaccactgcg tgactctggt  22500
caagagcact cagacggtcc agggacccca cagcgcggcc tgcgggctct tctgctgtct  22560
tttcttgcat gccttcgttc actggcccga ccgacccatg tctggaaacc cgaccatgga  22620
cctcgttgac ggagtcccca acgccctcct caactccccc accgtccaac ccaccctgcg  22680
caagaaccag gaggccctct acgccttcct ccgctcccac tccgcttact tccgtcaaca  22740
cgagacccag atccgcgagg ccacccgctt cgataaagcc ctcaaaatgt aaaagaacca  22800
cactggaaac tgttttttgt ctgactgaaa aataaattcc agctttattt gaaaaatcag  22860
acacggctca gactggctca atcaaacagg tcttggcacc cgtcgtccac cgccgcgggg  22920
aaagcgacgt tgcggtactg caagcggggg gaccacttgt gctcggggaa tttcaggggg  22980
ggaagccgct cgccctcaaa cacctccaaa aacatgttgc gcgccagctg cacgctggtg  23040
```

```
atcaggtcag gggcagagat cttgaaatcg caattgcgct gggggttggc cttggtattg  23100
cgatacaccg ggttgcaaca ctggctcacc agcaccacgg ggtacttggc gctggcccgc  23160
atcacgggat cccgaatctc ctcggggtcg ataccctccg agttgggaat gttaaagggg  23220
gtcagcttgc acacctgccg tccgctcagc ggccccgagc gggggtggtg attgcagaag  23280
caggtcatgc acagtaacag acagtcgcga cccttcttgg cctgagggta gcatgcccgc  23340
atgaacgccg ccgcctgttg gaaacccacc tgcgccttgg tgacgtcaga gtaggacatt  23400
ccgcaagaca ggttgctaaa gaccccgtta gggttgctcg cgtcgtgcaa gcacaccacc  23460
gcctcctcgt tacgcaactg caccacgtta cgaccccatc ggttctgggc aatcctggcc  23520
ttctggggct gctctttcaa agcccgttgg gcattctcgc tatttacatc catctccacc  23580
gtctgctcct tcctgatcat catcatgccg tgcaggcact tcacctcccc ctccttcacc  23640
gcactctggt ggtcccacat cacacacccc gtggggttcc agccctcggg ctccacccgc  23700
aactccgcaa agttggccac cagctgccac agcatgcgtc ccattatgtg gacgaagctc  23760
ttgtaagaag tgaaggtcag ctggggcgtg ttgtggctct gattcagcca gctctgacag  23820
accttggaca tcatctcaga atctaccggg ctcatattca agccctccgg gggcagctgc  23880
accttgaact tgttggtcag cgtgaccagc atgttctgag cggtggtgta agcctcaaag  23940
ggaacggccc tcccaacact caaaagcgct acggagccag cgccgctgga cccggcagtc  24000
gtagcactcg ctgcccccga ggtaacagag ggacccgtgt tcgaaccctc cgtctgcccc  24060
ttgctcgggt ccatcttttt tttttaaga ggagcgttcc cgctcaagtc caggctcgtg  24120
ggtctcttca gctgctgctc gctgatgcgt tccttgcttc cgtcggcgtg caccacggtg  24180
ggcgggttgg taaacagcac cttcacgatc tcgggctctg ccgccggctc ttcctcttct  24240
tcgctgctgc ttccgctgct cacgctcacg ggcgacggag gcagctccgg tttcgtttcc  24300
agcttctgct tgcggcggct ccgcttgggg ggcagcggag gcgggggatt tccctcctcc  24360
tgcggctggt tgctgctgct ggtgctctgc tggggcggtt ggtcgctcat ttttttcttc  24420
tcctaggttt ttgggagagg aacagcatga gcgactccgt catcagcatg gaagactttg  24480
aaccacccca gcaagatcaa tcgacagcac cacccaccga tgatgacgtg cccatagaat  24540
cagacgtgga gttcctcact gaggagcagc accgcctgcg tctagagcag gaggctgatc  24600
agcagataat gaagaaagag caggaaaccc agacagagga tgagcaggca aatcatgacg  24660
cagttcagga ggaggatgat tctggggaga agcagcagca gcgacatggc gatggctaca  24720
tcacagacga gatcctgctg acacacatcg cgcgccagag tctcatcgtg caagacgccc  24780
tggccgaccg cagccagatc cccctcaccg cccgcgacct caccgaggcc tacgagcaat  24840
gcctcttctc gccgcgcgtg ccccccaaac gccaacccaa cggcacctgc gagcccaacc  24900
cccgtctcaa cttctacccg cccttcgtcg tgcccgaggt cctcgccacc tatcacatct  24960
tcttccaaaa ttgcaagatc cccctctcct gccgcgccaa ccgcaccgcg gccgacgagc  25020
gcctcgccct cggcgaaggg gatagcatac ctgatatcgc ctccctggaa gaggtgccta  25080
agatcttcga gggtctcggt cgcgacgaga agcgcgcggc aaactccctg caaggcaacg  25140
gagacggaga agagagtcag tcggcgctcg tggagctcga aggcgacaac gcccgtctcg  25200
cggtgctcaa acgcagcatc gatgtcaccc acgcggccta ccccgccatc aacctcccgc  25260
ccaaagtcat gtcggccctc atggatcagc tgctcatcaa acgcgcggcc cccatcgacg  25320
ccgaacgcga aacatacaac cccgacgagg acgacagcga ggacggcaag cccgtggtct  25380
ccgaccagga gctcgctcgc tggctcaacg tggccctcga ctcccccctg ctggaggaac  25440
```

```
gacgcaagac cctcaccgcc gtcctcctcg tcaccctcaa cctcgaatgc ctgcgccgct  25500
tcttctccca ccccgacacc ctgcgcaagc tggaagagtc cctgcactac accttccgcc  25560
acggctacgt caggcaggcc tgcaagatct ccaacgtgga gctctccaac ctcgtctcct  25620
acatgggtat cctgcacgag aaccgactcg ggcagaacgt cctccactcc accctcaagg  25680
gcgaggcccg tcgcgactac atccgcgact gcatctacct ctacctggtc tacacctggc  25740
agaccgccat gggcgtctgg cagcagtgtc tcgaggagcg caacgtccag gagctggaaa  25800
agatcctgca gaagcagcgt cgcgccctct acacgggctt cgacgagcgc accatcgccg  25860
ccgaactggc caccctcgtc ttccccgaga agctcatgca gaccctgcag aacggcctgc  25920
ccgattttgt cagccagagc atgctgcaca acttccgcag cttcatcctc gaacgctcag  25980
gcatcctccc ggccatgtcc tgcgccctcc cgtcagattt cgtccccatc tccttccgcg  26040
agtgtccccc gccgctgtgg gcctacacct acttgtttca gctggccaac tacctcatgt  26100
accacagcga cgtggtcgag gacgccacgg gcgagggtct catggagtgt cactgccgct  26160
gcaacctctg caccccccac cgctcgctga tttgcaaccc cgcgctgttg agcgagagcc  26220
aggtcatcgg taccttcgag attcaagggc cagacgccaa aaagcaagag gccggtgagg  26280
aaacggccgt gggatccacc tccggcttca aactcaccgc gggtctgtgg acctcagcct  26340
acctgcgcaa atttgtacct gaggactacc acgcccacac catcaagttc tacgagcacc  26400
aatccccggt caagagccgg gtcgaaccct cggcctgcgt catcacccag agcagcatcg  26460
tggcccaatt gcaagccatc caaaaagccc gcgagtcctt cctcctgaaa aagggcaaag  26520
gggtctatct ggacccccag accggtgagg agctcaaccc ccttcccccc gccgcgcagt  26580
tatccctcag agatggcccc gcgaaagccg gctcccgcga agaagcaacc tccaccaccg  26640
ccagtccacc ccatctggga ggacgacgag gaggagtaca cggaggacga ggaggacctg  26700
ctgacagacg aggaggacat ggagggtctg gaagacatcg aggaggaaga cgaggaggag  26760
gatctggacg aggatccgca ggaggagccc agggagcagg cggttgcaga cagccagcac  26820
ctagcgccca gggcccctca ggcggctcct gccccgtcag cagcagcagc tccttccaag  26880
agtcgcagta gatgggaccg caagccagct gccgcgggta agggatctta caagtcttgg  26940
cgagcccaca aagcccgact gctgtggtgc ctgggcgaga gcgggggcga cgtgaatttc  27000
acccggcgct acatgctctt ccaccacgga gtcaacatcc cccgtaacgt catccactac  27060
tatcatcaat cctacagcgg cagcgactgg gccgaaatcg ccgcggcagc cagcctcctc  27120
gaggaaggga aaaaccagca gcagcaacag cagcagaagt aaaatccccc tgaggaaaac  27180
acctgctacc ggtagcagca gcggcgaaca gggcagcacg cgagcgctcc gggagaagat  27240
cttccccacc ctctacgcca tcttccaaca gggccgcgga cacagcctcg atctcaaaat  27300
caaaaaccgc tctctgcgtt cccttacccg cagctgtctc taccacaaga gcgaggatca  27360
gctccaacgc actctcgagg acgccgaggc gctctttaat aaatactgcg cctccaccct  27420
cccgcccctc ggtgatcatt aacccgcccg gcccgcgcgc gggaaaacgc cgctgactca  27480
cacctgaggt cagagtccga ttcccaccat gtccaaagtg attcccacgc cttacatgtg  27540
gagctaccag ccgcagatgg gactggcggc gggggcgtcc caagactact ccacgcgcat  27600
gaactggctc agcgccggac ctagcatgat cgcccgggtc aacggggtcc gcgacgagcg  27660
caaccagatc ctcatgaagc aagcggccat caccgccacg ccccgaggga ctctgaaccc  27720
gccaagttgg cccgcggatt tggtgtacca ggaaacgccg ccgcccgaca ccgtgctcct  27780
cccgcgtgac gcacaggccg aagtccagat gacgaattcg ggtgcccagt tggccggggg  27840
```

-continued

```
cggagtcagg ttcacgccct accgccggcc gggcataaat accctgcgct ttcggggcag  27900

aggcgtacag ctcaacgacg agacagtcag ctcctcgttg ggattgagac cagacggagt  27960

cttccaaatc ggaggatccg gcctctcgtc tttcacacct cgccaggtct acctcaccct  28020

ccagaccgct tccagccggc ctcgctccgg tggcatcgga accctccagt tcatcgagga  28080

gttcgtgccc tcggtctacc tcaacccctt ctcgggacac cccggtcact acccggacga  28140

cttcatcccc aactacgatg ccgtcagcga ctcggtagac gggtatgact gatggagatc  28200

tagaggctga agttgaaaaa gctcgcctcc gccatctcgt ccactgccgt cggcctcggt  28260

gctacgcccg ggacctgctc ctgctcgagg gtttcttcta cccgcccaac catcccgaag  28320

gccccgctca cggcctccgc ctcaccgtac ccgagaccca gcgctcccgc ctggacaact  28380

tcttcaccgg tcggcccttg ctcgtcgaga ccacccacgg acccgtgacc ctcagcgtca  28440

cctgcatctg cgccgccaca cagctgcatg aagagctgtt tgagcgtctg tgtactatct  28500

tcaatacttc tacttgccct cagcagtgag ttaataaact tgaactgcac tgaacaacca  28560

gccactcggg gtgatctgtt ctacaacgcc aacgggtcac tgatcgtctt ccttcagtgt  28620

cccaaccact ccagcctctc ctaccccatc cactggtctt acaacttctc cgtccccgtc  28680

gccaacttca ccccggccgt caacgccact cgacagccgc ctctgctcgc ccatcagggt  28740

tggaacgaga ccgtcgccaa cggggttgag tctgtgatcg tcctcgagaa cccaccggag  28800

ggcgtctact gctgcctctc caacctcacc gtctgcagtt gctggaactt cactgacttc  28860

aaccgcaccc tcgagggctt cagcaccacc accacccttg ctaccactac tacctcggta  28920

gaaaccacca gcaccgccgt cgccaccact accgccaccg tcgacctccc actacccgag  28980

ggagctcagg aaggacagga cttttacttt gtggaggaga gggaaactca tctccagcta  29040

gactccaagt tctggactgg tctgactctg ggactagtgc tcttcgtctc cttggttctc  29100

ctctgcctgg tggaatacag gcgaaaccaa gtcggtgatt cctacaccac tcaggagcct  29160

ctcttgcaca cagtctgaga ccactcaggt aaatatgagg gtctggcaat acctcgtcag  29220

ggggctcatg ctctctctgt tttttctcct caaagctgcg agtcccttca cttacatctt  29280

ctccattctc ccgtgggatc atatggttaa cctgccttgt catggggatg ggtctgtggg  29340

cccctgtccc cattcccggg tccacgaatg gaccttcaac gggtcttaca taggctcctt  29400

ccagtgctcc aacggggtga ttcctaatga ctggtctaac atcttagctg gaaacttcac  29460

caccttgtct gtcctcaatc cccctcgagg aaaatactgc tgcactctca gggatcgata  29520

cgaggaatgc ttcggggtgg gcttagaatc ctacgtccac cagttgggag cccatgatag  29580

gaatgtctat gaagaaacca cctctgctcc ttctcttccc ttctccatta tgccttccaa  29640

tcccggggag tttgtgctgc tggtctttct gtttgtgtgc atgttcttgg gggcctacct  29700

cctgtaccgc atcaggcggc tgtatgtgac taaccaggag tctttttctt atgttcaatt  29760

tactaacagc ccagaataaa tcagcatggc caacccacgt ctgctcaccg tcctcgcttg  29820

tctcgctatt cttcttacct ttctaccact ctgtcaaact acttgccatg aaagagattt  29880

cgaggttgaa ataggcggag atttagacat tgatgtattc caagtttttg aacattggca  29940

tatcaccttt aaaaggttgt acaacagaac tgttggccaa cgtttagtat gtgatagcag  30000

ctcaggtcct actgactatg gtttttcttt taatgaccat tttttacaac tcagacatgc  30060

caccaaagat cacattggca tttttacgct ggaagtggaa tacaatgacc ccacatactg  30120

gtttccagca gtagcaagat gtcctattaa cattactctg gttgatttca ctgaaccaaa  30180

atgtattctg ggatgcactg ttgaagacca tggcttcatt aaagatgtaa tgcttatgtg  30240
```

-continued

```
caacacaagc catgacataa taatgacagt tgtcagcgat actgtttcga ctgacatgca  30300
ccaccgtttt ttagctactg cttacacttc aaatttagtc attttagtgg tggctttcaa  30360
taatcagtct actgcaatta cccactttgt aatgacacct ccatggatca atgacaccag  30420
ctgtcccaat ctcattacta ttaacatcac aacaagacac ggtttcaatg acaacagtga  30480
atgggaagaa gttggacagc ttgggttttc acacagtgca cagtcagatg ctgtttgtga  30540
tcacgaccac acttcctaca ttttgatcat cgtcatcgcc ttcctcttca tgctagcaga  30600
gctgctcttt atcctctacc tctaccacaa gtacttcaac tggggcaggg ggtacagagg  30660
gccgcccatc atcctcgaaa acaaatctga cgcacctgcc cccaaatatt cctacaggta  30720
tgcctaggcc gtctgtcatc ctcacagcag tcacagttct ccctgtgctc tgttctctag  30780
tggccctcag cgcatccaac tccctccaag gcacctgcct tccctcctgg gccggactct  30840
tggccttcgc tttgcttaac atcacctgtc tgctcagcac cctctgcttc ttcttctccc  30900
tcgcccaact cattgactac gcgagattca gaagaaatca cagactcaat cgagaagcag  30960
gaccagccgt catcaacctc atcaacctcc cccgcgccca accatgaact gcaccctaga  31020
cttctacgga aaaatcttct tctttagaga cccctgtgaa tgtaccacca tggactatgg  31080
catctacctc atatatgaga tcatgctgct aatctctgcc gggttagcag cggctatcat  31140
gcacactaac tacctcaaac taccatgggt aaaaagcccc aattccaacg ctcctccctc  31200
tccacccccc agccctcctc ctcagcctcc tgccgctgtc gctctcatcc ctccaccgcc  31260
acctccgccc cccgtgtacg cgcgagtaga ccccgacccg ccaccagcct acttcgagat  31320
ctactttgga gacgatggaa cagaatcaga ctgacgtgca gctagagatg gatggcctca  31380
tggcagagca gcgtctcctc ctccagcaag ccaacgaccg ccaccgcaaa atgaaaacag  31440
acgaggtcag aacctatgcc aacctgcacc aatgcaagcg cggcaactac tgcctcgtca  31500
aacaatgcca tctcgagttc accacctgcg ctaacgggga ccacgagctc atcttctccc  31560
taccctgtaa ccgcttctcc agcgtctaca ccgtgggtca gcacaccgtc aggctgggca  31620
tcacccgcgg tgagacttca ggatctatcc gctgctcctg ccacaatcct gattgtctac  31680
acactctaat gaagaccctg tgtggtctca aagataattg ccccatctga ttaaactgtg  31740
attcaataaa gattacctga aatctgacag caggtctccc aagtctagtt tgtctagcac  31800
ctccacgtag cgcccctctt cccagctctg gtactccaga ccccggcggg tggcatactt  31860
cctccacagg ctgaatggga ggtgggtggt ggtaagactg gaaccgcacc agacgtgcat  31920
cgcggtgggg ggtctcatct ctgctctctt gcagatgaag cgggcgcggg tggaagtgga  31980
aggggacttc aaccccgtgt atccctttga taaggatgac gaacaggaca atcaagacgt  32040
caacagcacc ctcccaccct tcctctcctc caatgggctc actgaatccc cggcggggtt  32100
cctcgccctg aaaacttcca accccatgga tttcactgac aaaggcgcac tcacagtcaa  32160
aaccaatccc cccatagagg tcaattcaag tggacagctc agtctcaaat taggatctgg  32220
tctcacagtc tctggggggg cactgcaggc catgggtgag accgtctcag tcacagctcc  32280
catcaccaag actaatggaa acataggctt acaactggcc agtaacccag gcctgcaagt  32340
cagtaatggt ttaaagctta aagtcacagc accattcacc ctcaataata atggtctgaa  32400
cataggcgtg gacgcgccac tcagaataca agataacaaa cttcaattat ccacgggaaa  32460
tggcatagaa gttgccagta acagaacact ggctgttaaa cttaaaagaa caggaaacaa  32520
caatcaagga ttagactttg atggtgtaca gctagtctta aaattgggag atgggttgaa  32580
attaggcaac actgggtatg ttgacataag attaggaaat gccaataact gtggcttaca  32640
```

```
acttgaaaac ggggaattaa aattcaaaat gggggatgga ctgatttatg gcaacacagg  32700
atatgttgat gtcaacgttg ggcaaggtat agagattaat caaagaaagg ttaaagtgaa  32760
aacagcagaa ggcctagcct tcgacaacca aaataggtta aaaatcaagt gcaatacccc  32820
actaggattt gatggcactg gtaatttgaa agtgggttta ggagatggcc tctatatagc  32880
caatgataaa attttttatg aagctcccac actatggaca accgcatctc cacaaactaa  32940
tgccaatgtg agatctgaaa gcgataatca aacaactaaa aatgctaaag tgcagctgac  33000
cctatccaga tgtggagcca tggttctagg gtacatctca gtttatggca ctggagcccc  33060
cctcattccc atcaatacag gtactacgac taatttaaga ctattgctag cctttgatgg  33120
agagggtaga ttagttaatg gtaataacat gctgacgtcc tctttagaag tgaaggcagg  33180
agccacagtt aatgcatcat caggaataga caggagaatc tttatgccca ataaaggttc  33240
ctatctaaac tcaggctctg attcaggaca ggctcacaac gccatattta gaaaggtcta  33300
ccttaacaaa gacataaata aaacatgtga tctaactcta acattaaatg aaaacagagc  33360
aaatggacaa tattcattat actttaagtg gaccaacttc agcgccagtg ttaataatca  33420
aacctttttcc acctgtgtaa cccactttgt ctatctgggt gaaaatccat gaaaataaaa  33480
ccaaactatt ttaaacaaat caacttttta ttttattctg agaaaaagaa gaagcaccgc  33540
caccacgctg ggtctctgg ggagagtaag gaacaaaggt aatcttcttc acgtgtttgg  33600
tgcggatccc cccaccgccc ggccacttcc acccgtacgt caccggtccc acgggaacca  33660
tcaccagtgg ggcgatgtgg ctctggcccc acaccttcac acagtcctgg tgggcgcaac  33720
gggaatcatc cagttgcaaa aagccctgag acacatggga cacatccaaa cagttcttaa  33780
gtctgggatc tgaggtcttc tccaccggct caggctgtgc tgctggcgct gctgccgtcg  33840
acggtgccgg gtcacggggc atctcaaaca aggggtcggg aatctgcagg atctgagcca  33900
gcatgtcggt gtctatctgc ggtgagaagg agggcggtac ggtcgcacgt tgcggcaccg  33960
gtcatacaca tcataactca gcgcccggga ccgccacatc acgctgtcaa acatccgctg  34020
gcgctgccgc tcggtccggc tcgccctcaa aggatgacgg gaaatactgt ccaattcccg  34080
caccgagcga gccagcaggc gccgcgtccg tctggcgcaa cacctgaacc tgatctcctc  34140
gcccgtgcgg cagtacgagc agaccagaac cagcatgttg ttcatcaccc cataatggaa  34200
agcagacagt ccaaaattca cagtcctgat caggtgctcg gcatgctcat cgtatctcac  34260
gttgatgtaa atcagatgca gtcccctcac atacacgctg cccacataca tcatctcctt  34320
gggcatatgg tcgttcaccc aggggcggta ccacgggatc ctcagattca ccaaggatcc  34380
caccaccaac agatagaacc atctcctcaa caacaccgcc cccgcccgac actgcagaga  34440
ccccgggcgg ctacagtgac aatgcaacat ccacacctcc gagcccctga tcatccgaca  34500
gtggacaatg accagcgtcg cgggacaagc acacacatgc atgtactgtc tcatgagatg  34560
ttgttcatac gggctcaaaa agaaatggaa cggagccggc cattccaagt acactgtaaa  34620
catcacactg gacgggaccg atcttaccgt gatcacatcg tgcagggtgt tggtgtcaca  34680
gcgccgggcg aaacattcac cttgggctgg gggatcgggg tccgggagag gtagctgatg  34740
ctgatgaaaa ggggccaagg ggcccggagg cggttgaggg ttccgttgat ccatgagatg  34800
acgaagaaga agaatacaag caggaatatt ccagttctcg ctgctgatcc agttgacggc  34860
gcaccagatt gtatttccga aagcaaaaga aggcccgctg ccaagccgca ggtgaaactc  34920
gccgggaggg tgaggtcacc ctctgcctct caaagtaggc ggcgtgagcc aacaactgac  34980
tcagcccggt caacagtcgc cactgatgac ctgtcaactc ccagcccgtg cgagagcaat  35040
```

```
aagcgatgag gtcatccacc aaagcgcgag tgccgcgaag ccagtccaaa gcagagtggc  35100
ggtcgcgtac cagaggagga gcagggacgg cgggaagaaa aggcaccatg agaagagccc  35160
ccttactgct gaagcaggtc gtccaggatt tcaaactgga ggtcccgaag gtagcatctg  35220
cgtcccccgc tgtgctgatg ataggtcacc gccagatcaa aatggacacg gttctccaag  35280
cccgacacca ccgcatccac caacgcagga agatgaagct tgagataaat caaaaatgtc  35340
accttctggg gattcagatc gttatcctcg aaacaataca tagaacactc atcgatctgc  35400
tgcaactcgt tctcctgctt ccagccatta acgatgcccg tcaggacatc atcaaacacc  35460
aaaattagca tggcggaaga gctgaacgag agcaatctcc acctccagac ggagacacaa  35520
gcggaccatg ggacggtgtg ggcggtgggg gcggcgacgt ttagtcgctg agcgcctcag  35580
gctcttcaga aacctgcaac agatccagaa ggccatcagg cacggtaatc tgctccaaat  35640
gagcctgcca ggtgatctgc tgctttaacg catcgagcag atcttccaac accgcctggg  35700
tctctggcgt ccctgaatct agctcctggg tccccacgca acacaaaagt ctcagctccg  35760
gctcccgctg cagcacgtgt acccccacgt aaacgttctg cctctccccg cgcatgtcta  35820
gaaaacatct ccaaaaaagc tcgaactctt gtttcaggag gcgtaacagg tcaaagccac  35880
gcccctccag gtaagacacc aggggagcgg gcgcttgcaa cagacaccac agaggacggt  35940
ggacagacgc catacctggg agaatacaag aagatcagag ctcagttatt tccaccactt  36000
gcggaaaact ggtgccctgt aagactagac gggccacggg ctcccccgcg cggccgtgat  36060
agtcaaaggg cccattgttc accagcagat tttcaactcg gcctcgaggt tgcagggcac  36120
cagatcggcc tccacataca ggctgtgggt gctcacgttc cgctggagtg aagatagacg  36180
ccccacaaaa ccaacaggca cccgaacaga aggccggtat acaagagcga gcgacctccg  36240
gcatagacag taaaatctgt aagagcataa agatcatagc tgccggtgcc gggtcgctgc  36300
gtcggcaggt gcgcggtctc ctcgaggcgt tgcacaaaaa ggttcagacg ctgccgagaa  36360
gccatacagt aggaaaaaag tggccctcct taccgtctgc tcgctcgggc ggcagtcagc  36420
gagagaaaat ggcgatcgct gactccacac gcgagcccgg cgcaatatat agaccctaac  36480
ccctcccatc gcgtcagaga ccacaggtcg gtatgccctc gttaatggtt aacccgggaa  36540
ttactcggaa aattttccgc cgcacccgtc tgcgcgcgaa aacctgaact tccgcctccc  36600
gcgttcccac gtgacgtcac cgacttacaa catccacttc ccacacccgc gcacaaaatg  36660
gctgccgtgg gaaccgcctc aaaactacag aatccccgaa aactaccaac atggccgccc  36720
cgcgccaaac acgccggaag tcccgcccca cacccctcaa cccccaatcc ccacactccg  36780
cgtttttcac cacaaccgga tgtaaatttg gacgtttttg aggtatatta ttgatgatgg  36840
gc                                                                 36842
```

<210> SEQ ID NO 2
<211> LENGTH: 2046
<212> TYPE: DNA
<213> ORGANISM: Titi Monkey Adenovirus

<400> SEQUENCE: 2

```
atggccttga gcatccccga ctgcgcccgg ctcaccggtc agaccgtgcc gaccatggaa     60
tacttccgac cgctgcgcaa catctggaac cgcgcccggg agtycacgcg ggccagcmcc    120
accgccaccg ggatcacttg gatgtcgcgc tacgtctacc actaccaccg cctcatgctg    180
gccaacctcg ccccgcgcgc cgccgccacc cggcactggc cctgttacaa cctgccgccg    240
ccccacttcc tcgtgggcta ccagtacctc gtgcgcgtct gcaacgacta cgtcttcgac    300
```

```
tccagggcct acagccgcct caagtaccgc gaacaggtgc acgccggctc gcagaccgtc    360
aactggtccc tcatggccaa ctgctcctac gccatcaaca ccggcgccta ccaccgcttc    420
gtggacctcg acgacttcca aggcaccctc gccagcatcc aacaggccat cctcagcgaa    480
agggtcgtgg ccgacctcgc cctcatcgag cccctgcgcg ggctgggccg cacccacatg    540
gaaggtgggc aggccgaaga cgtgcccgtc gagagactcc tgcaagactt ctacaaggac    600
ctcggcgtgt gtcaagatca agcctggggc atggccgaca gattgcgcgt ccagcaagcc    660
ggaaggaagg acctggtcat cctcgccgcc atccgccgtc tcaagtcggc ctacttcaac    720
tacctgctct cgctgcaaca acccccgccc ccctcctctt cctctgcgga acctctgggg    780
ggacagaacc aagaaggcct tcctccatca ggcgggaccc ccacgatgag cacggtgctc    840
agcctacctt gcgattgcga ttggctcgaa gctttcgttc aacgcttctc agatcccgtc    900
gatctgcagc tcttgagatc ccacgctggt ctcactacac aaaatttaat cagatgcatc    960
gtcaatgccc tgtcgctgcc caaccccgac cgccgccgcc atgacttgga aggcggggca   1020
cggcccgggc tcaggcgtcg gcccaccgcc gggaggcgca cgcgctacgc cggcactttc   1080
atcctgcgcc cccgcgaaga cggagtgccc gtcaccgaaa ccatgcgccg tcgccgcgga   1140
gagatgatag aacggttcgt ggaccgtctg cccatccgcc gccgtcgtcg tcgagcgccc   1200
cctgctgctg ctgttccacc agcggcggct gtagaagaag aggagttagc acccccggca   1260
gagatccccg agttggtaga ggaagaagaa gaaatcttgg aagaagaaga ggaggaggaa   1320
gaggaacccg aagctttcgt ccgcgaggtc ygggccacgg tggccgaact catccggctc   1380
ttggaagaag agctcacggt ctcggcgcgc aacagccagt tcttcaactt cgccgtggac   1440
ttctacgagg ccatgcaacg gctcgaggcc ctcggcgaca tcaacgaact caccctccgg   1500
cgctgggtca tgtacttctt cgtcaccgag cacgccgcca ccaccctcaa ttacctctac   1560
cagcggctgc gcaactaccc cgtctgcgcc cgccacgtgg agctcaacct cgcccaggtg   1620
gtcatgcgcg cccgcgacgt ccacggagac gtggtctact cgcgcgtctg gaacgagaac   1680
ggcctcaacg ccttccaaca actcatcggg cgcatcagca acgacctcgc cgccaccgtc   1740
gaacgcgccg gacacgggga actcgaggag gaggaagtcg agcagttcat ggccgagatc   1800
gcctaccaag acaactccgg cgacgtcagc gaaatcctca ggcaggccgc cgtcaacgat   1860
gccgagattg attctgtcga attgtctttc aggttcaaaa ccacgggacc ggtggtcttc   1920
acccagagac cccagatcca acgcatgaac cgccgagtca tcgactacgc ctccagtctc   1980
cgggccaggc atctcgccct gcccccgctc aacgccgccg acgtcgagct gccacccccc   2040
gagtag                                                              2046
```

<210> SEQ ID NO 3
<211> LENGTH: 1374
<212> TYPE: DNA
<213> ORGANISM: Titi Monkey Adenovirus

<400> SEQUENCE: 3

```
ggcggaaacg cccgctacga gaccagtcgc ctcaccctca agcgctcgct cgccagcgtg     60
caagctcaag cccacccctt caccgtcacc gaaaccaccc tccggaggac cctcagaccc    120
tggaaagacc ggaccctggc cccgctcacc cccggggaga tgcatcggct ccggccctac    180
tccaacagcc atcccaaccc aagaaaccaa gaaacctgct ggatcgagat gccctagaac    240
acgtccgcga gatctgggaa aaaacccaaa ccctcgctga ctcactcgcc aagatgtcgc    300
tggccgacgg cctgaaacca ctcaagaact tccagtcctt ccaagaactc ctctccctcg    360
```

```
gcggttccaa gctgctccag gatctcgtcc aagaaaacct catcatgcga gacatgctca    420

actcggtcat gccctacctc aaccccgcgg acggcacctg ccgctcgctc aattacaaca    480

tgcaacccgt catcggggtc atctacggtc ccaccggctg cggcaagtca cagctcctcc    540

gcaacctcat gtccacccag ctcatccagc ccgcccccga gaccgtcttc ttcatcgccc    600

cccaggtcga catgatcccc ccctccgaga tcaaagcctg ggagatgcaa atcttcgaag    660

gcaactacgc ccccgggccc gaaggcaccc tcatccccca atcggggacc ctcaccccca    720

aattcatcaa aatgtcctac gacgagctca cccaagacca caactatgac gtcaccgacc    780

cccgcaacgc cttcgcccgc gccgccgccc ggggacccat cgccatcatc atggacgaat    840

gcatggagaa cctcggcggt cacaaaggcg tcgccaaatt cttccacgcc ttcccttcca    900

agttgcatga caagttcccc aagtgcaccg gctacaccgt cctcgtcgtc ctgcacaaca    960

tgaacccccg tcgagacctg ggcggcaaca tcgccaatct caagatccag gccaagatgc   1020

atctcatcag cccccgcatg catccctccc agctctcccg cttcatcaac acctacacca   1080

aggggctccc cgtggccatc agcatgcttc tcaaagacat cttctcccac cacgcccaga   1140

cctcccagta cgactggatc atctacaaca ccaccccccga gcacgaggcc ctccaatggc   1200

tctacctgca tccccgcgaa ggcctcatgc ccatgtacct caacgtgcag acccatctct   1260

accgagtcct ggaaaagatc catcgcaccc tcaccgaccg caaccgctgg gtccgagcct   1320

accacgcccg caaagcccta ccctcccccc aacagcaata aatggaaacc cgag         1374
```

<210> SEQ ID NO 4
<211> LENGTH: 1602
<212> TYPE: DNA
<213> ORGANISM: Titi Monkey Adenovirus

<400> SEQUENCE: 4

```
atggaagcac acgctgaggg aggggatcct gagaggggtg atgcaggggc cccgggcgcg     60

ggtgaaccgg gagatcaggc gggaggtgga ggagcggctg acgcaggtgc agcgggagtt    120

ggaagagagg gagagggaga ggcagcagcg ggagagggag cagcagcagc aggaggggga    180

aatgactacg agcatatgga ggccttccat ggaggcggag tggccgccgc gggcggggat    240

ggaccccccg ctggaggagc agtgggaggc ggaccacgac ccggaggcat aattcagcag    300

gtggctaggt tgtttcccga gctggccggg cagttgcgag ctcccttgca tcggcccgtg    360

cctcgacccc caccgaggaa tgtggatgag cggcggggca tagtcagacc ctgggatgag    420

gccaatcccc agccagccga tgagcaagcg ggcccctcgg accgcacgcg atcttggatg    480

atgagacgcc gtctggagaa cattacttgg caagaagtct gggatgactt tttgaggggt    540

gacatgtttc tgagggatag atacacgttt gagcagatcc gcacgcactg ggtggacccc    600

cacgaggatc tgggcctggc gatcgctacc cattgcaagg tggctttgca tccagacagg    660

acctatcgtg tgagggacaa aatatttatc cagaactgtt gctatgtcat tgggaacggg    720

gccacgatta tggtggagac gagcgagcgg gtggctttcc agttgggaat gcaacagatg    780

agcccatcca tcacggggat gtttggatgt acttttgtaa actgtcgctt cagttgcgac    840

cctaacgtgt tccgaggaat ttgcatcgcc gcgaacacgt catttctggt ccacggttgt    900

catttctttg gtttcccggg agattgtatc gtggccaacg tgggtggtcg ggtgcggggc    960

acgaccttca cttcttgctt taaggggatc tataatcccg ggcgccatgc tctgtcggtg   1020

agcaagtgca tctttgacaa atgtatgata gccatcagca ccctgggctt ttccaagatc   1080

agacacaatg tggccaccga gtgtttgtgc tttttactgt gccggggctt gggtcgcatc   1140
```

```
cagggcaaca cggtgcacgg gccttacctg agctcccacc ggatggtgac ctgcggggac   1200

gggaccatcc agaccctgcg taccatccac atcgtggccc acccgcgccg cacctggccc   1260

gtgtttgagc ataacgtgct gatgcgcacc agcatgtacc tgggcaaccg gcggggcatc   1320

tttatgccgc gccagagtca ggccttccac accaacctgg tgctggacca gcatgcctcg   1380

acccaggtgt ccatcagcgg gctgtatgac atgagcctgc agatatatcg gacgctgcgc   1440

gtggacgaga cccgcagtcg gctgatgcat tgcgagtgcg gcgagtctca cctggtgaat   1500

ggacacgttt tgggaatctg tacggacgac atgcgagtgg atccgctcca atactcggcg   1560

gctcggaccg agtactcttc ttcggaggat gaagcggact ga                       1602
```

<210> SEQ ID NO 5
<211> LENGTH: 543
<212> TYPE: DNA
<213> ORGANISM: Titi Monkey Adenovirus

<400> SEQUENCE: 5

```
atggatcaac ggaaccctca accgcctccg ggccccttgg ccccttttca tcagcatcag     60

ctacctctcc cggaccccga tcccccagcc caaggtgaat gtttcgcccg gcgctgtgac    120

accaacaccc tgcacgatat gctggctcag atcctgcaga ttcccgaccc cttgtttgag    180

atgccccgtg acccggcacc gtcgacggca gcagcgccag cagcacagcc tgagccggtg    240

gagaagacct cagatcccag acttaagaac tgtttggatg tgtcccatgt gtctcagggc    300

tttttgcaac tggatgattc ccgttgcgcc caccaggact gtgtgaaggt gtggggccag    360

agccacatcg ccccactggt gatggttccc gtgggaccgg tgacgtacgg gtggaagtgg    420

ccgggcggtg gggggatccg caccaaacac gtgaagaaga ttacctttgt tccttactct    480

ccccagagac cccagcgtgg tggcggtgct tcttcttttt ctcagaataa aataaaaagt    540

tga                                                                  543
```

<210> SEQ ID NO 6
<211> LENGTH: 145
<212> TYPE: DNA
<213> ORGANISM: Titi Monkey Adenovirus

<400> SEQUENCE: 6

```
gcccatcatc aataatatac ctcaaaaacg tccaaattta catccggttg tggtgaaaaa     60

cgcggagtgt ggggattggg ggttgagggg tgtggggcgg gacttccggc gtgtttggcg    120

cggggcggcc atgttggtag ttttc                                          145
```

<210> SEQ ID NO 7
<211> LENGTH: 145
<212> TYPE: DNA
<213> ORGANISM: Titi Monkey Adenovirus

<400> SEQUENCE: 7

```
gcccatcatc aataatatac ctcaaaaacg tccaaattta catccggttg tggtgaaaaa     60

cgcggagtgt ggggattggg ggttgagggg tgtggggcgg gacttccggc gtgtttggcg    120

cggggcggcc atgttggtag ttttc                                          145
```

<210> SEQ ID NO 8
<211> LENGTH: 3534
<212> TYPE: DNA
<213> ORGANISM: Titi Monkey Adenovirus

<400> SEQUENCE: 8

```
gttcaaaacc acgggaccgg tggtcttcac ccagagaccc cagatccaac gcatgaaccg     60
ccgagtcatc gactacgcct ccagtctccg ggccaggcat ctcgccctgc cccgctcaa     120
cgccgccgac gtcgagctgc caccccccga gtagtccccc tcaacccgct gcgcggcaac    180
gtcctcgccc ccgcggtacc aagtccctgc acgtcatcga cccccgctcc ggcgtgccca    240
ccgaaatcaa gtactatggc gtcgccgggc atctcgccgc gcccatccgc accctctgtc    300
gcgtgcatct ctgcgacgag cctcccgacg catttttcca agacctccac gtgcacaccc    360
tcatctccaa gatgcaagag ctccggccca ccgcctccga gatctggcgc gtggaacccg    420
gacgggccca ggcccaagtg gcccccgtcc ccgacctcga cgagcatcat ctcctgccct    480
tccccctgca cttcctcgtc cgccaacacc aactctacct catccactcg ctcatctcag    540
aacagaaaat gtgaattctg cgggcgctac tacaagcaga cccacacctg ctccgtccgc    600
cgccgcgact tctacttcca tcacgtgcaa gcccactcct cgcactggtg gcaggagatc    660
aagttcttcc ccctcggggc ccacccagac acccgtcggc tctttgtcac ctacgacgtg    720
gaaacctaca ccagcatcaa ccgcttcggc aagcagctca tgcccttcat gctcgtcatg    780
catatcggcg gcgacgagca gatggccgcc gaggcccagc agctagcacg tgaccagggc    840
tggcaagtct ggcggtccct cacccacccc cgggtcttct acctgctcac cccccagccc    900
aaagccatcg gctgccgctt caaagagttc cgcgactccc tgcagcaaca ctttgcccgc    960
cagctctggc gactcttcaa actggaaaac ttccaactcc tgcacgacct cgccgccaag   1020
gaagggctct cctccccaga cgacttgcaa cccgaacact tcaaaagcct caaattccag   1080
ggccgacccc gcttctggga aatttacatc atcggccaca acatcagcgg cttcgacgag   1140
atcgtcatgg ccgcccaggt ggtcaaccac cgcggcgaga tccccccgcc cttccgggtc   1200
actcgcaact tcatgccccg ctgcggcaag atcctcttca acgacatcac cttcgccctg   1260
cccaacccccc agtacagcaa agaggggggc accgactacg ccctctggga gcagggggggc 1320
tgcggggacg ccgatttcaa gtgccaatcc ctcaaattca tggtccgcga caccttcgcc   1380
ctcacccaca cctctcttcg caaggccgcc caggcctacg agctctccgt ggagaagggc   1440
tgctgcccct accaggccgt caacgagttc tacatgaaag gcacttaccg gacagacagc   1500
gatggattcc ccgacgaagg gtattggaag gactccgaag agtatcgcct caacaaggag   1560
ctgtggctgc aaagcaaaaa gacccacgat gagcgctacg atctcgtcaa gcagaccctc   1620
gactactgcg ccctcgacgt cctcgtcacc gccgagctcg tcctccgctt gcaagactcc   1680
tacgcccgct tcgtccacga gtccgtcaac ctcccccctct gcgccttcaa catcttccaa  1740
cggcccacca tctcctccaa ctcccacgcc atcttccgcc aggtggtcta ccgagccgag   1800
cgcccccaga aaccccacct cggctccgtc ctcctcgccc cctcccacga gttgtatgac   1860
tacgtccgcg ccagcatccg cggggggcgc tgctacccca ccttcatcgg cgtcctcgag   1920
gagcccctct acgtctacga catctgcggc atgtacgcct ccgccctcac ccatcccttc   1980
cccgcggggg cgcccctcaa cccctacgag cgggccctgg ccctgcacgc ctggcagcaa   2040
cggctcgacc gccgcgacac gcccctggac tactttgacc ccgacctgct gcccggcatc   2100
```

```
ttcaccatcg acgccgaccc cccgcccgag gacatgctcg acgtcctgcc cccttctgc   2160

tcgcgcaagg gcggccgtct ctgctggacc aacgagagcc tgcgcggcga ggtggccacc   2220

agcatcgacg tcatgaccct gcacaaccgc ggctggcgcg tgcgcttgca acccgacgag   2280

cgggccaccg tcttccccga gtggcgctgt gtcgcccgcg agtacgtgca actcaacatc   2340

gccgccaagg aacgcgccga tcgcgacaaa aaccaaacgc tccgctccat cgccaaattg   2400

ctctccaacg ccctctatgg ctccttcgcc accaagctgg acaataaaaa gacggtgttt   2460

tctgaccaga tggagggggc cctcgtcaag ggcgtggcct cggggcacta ttccatcaaa   2520

tcctcctcct tcattgaaac tgacaacctc agttctgaat acatggacgc ctgggcggca   2580

gaattcttac ctggacagct ggcgctgcaa gagcccacgg tcgtcgccgg cagcggtagc   2640

gatcccgagg aggacaatga ggaccccca gaacacgccc ccttttatac cccccgcag   2700

ccgacccccg gggacccaga tcacgtgacc tacacttaca agccaatcac cttcctggac   2760

tgcgacgagg acgcgctctg tctccacacc ctggaaaaga acgacccctt gatcgagaac   2820

gaacgctacc cctcgcacat tgccagcttc gtcctcgcct ggaccagagc cttcgtctcc   2880

gagtgggccg gcttcctcta cgacgaggac cgcggcaccc ccctccacct gcgacccctg   2940

aaatctgtct acggagacac cgactccctc ttcgtcaccg aacgcggcca tcgactcatg   3000

gaaacccgag gtaagcatcg catcaagaaa aatggcggag gcctagtctt tgaccccag   3060

catccccagc tcacctggct cgtcgaatgc gagacccagt gtagcaagtg cggcgccgac   3120

gcctacagcc cagagtccgt cttcctcgcc cccaaactct acgccctcaa atccctccgc   3180

tgcccccagt gcggtcacga gggcaaaggc aagctccgag ccaagggaca ccccgcctca   3240

gaactctcct accaactctt gctcaattgt tatctcgagg aataccaagg cggaaacgcc   3300

cgctacgaga ccagtcgcct caccctcaag cgctcgctcg ccagcgtgca agctcaagcc   3360

cacccttca ccgtcaccga aaccaccctc cggaggaccc tcagaccctg gaaagaccgg   3420

accctggccc cgctcacccc cggggagatg catcggctcc ggccctactc caacagccat   3480

cccaacccaa gaaaccaaga aacctgctgg atcgagatgc cctagatggc cttg         3534
```

<210> SEQ ID NO 9
<211> LENGTH: 2790
<212> TYPE: DNA
<213> ORGANISM: Titi Monkey Adenovirus

<400> SEQUENCE: 9

```
atggcgaccc cctcgatgat gccgcaatgg tcttacatgc acatcgccgg tcaggatgct     60

acggagtacc tgagtccggg tctggtgcag tttgcccggg cgacggaaag ctacttttct    120

ctgggcaaca agttcaggaa cccgacggtg gctccgaccc acgatgtgac cacggaccgt    180

tcccagcgtc tgacgctgcg cttcgtgccc gtggacaagg aggacaccgt gtactcccac    240

aagtgccgct tcaccctggc ggtgggcgac aaccgcgtgc tggacatggc cagcacttac    300

tttgacatcc gcgggrymmt cgaccggggg cccagcttca aaccctacag cggcaccgcc    360

tacaactgcc tcgcccccaa gggcgctccc aacaattgcc agtggatgac cacaggagaa    420

aaccctaaaa ccagaacata tggccaggcg ccatttgaaa cagatttcat taaccaaaat    480

aacaacatag gtgttcaggt tggttggaca acagctgaag ttccccaacc aataatagcc    540

gactccaaat accaaccaga accacagtct ggacaaaatc aatggcagtc agctgtaaca    600

tcaacggtta ctgaattttc tggcagagtt ctgaaaccag atactcctca acttccatgc    660

tatggttctt atgctagacc cactaatgat tatgggggtc agtgcaggga aggtcaacag    720
```

```
gtggatcaag tgtatttcaa tgttgaaaat caagtcaatg ctcctaaagt cattctgtac    780

tctgaaaatg ttaacataga atcgccagac actcatatta tctttcaccc tacacccaac    840

ggtacacatc caaatgcatt ggaagatatg ttaggacaac aggcctctcc caatagaccc    900

aattacattg gtttcagaga caatttcatt gggtttatgt actacaacag cactggcaat    960

cttggggtcc tggcggggca ggcgtctcag ctcaacgctg tggtggactt acaagacaga   1020

aacactgagc tgtcgtacca actgatgctt gatgcgctga gtgatagaac gcggtacttt   1080

gcaatgtgga atcaggctgt ggacagttat gatcccgacg tgaggatcat tgaaaaccat   1140

ggttgtgaag atgaaatgcc caactattgc ttccctctgg gcggggttgg tccaatagag   1200

aagtggattg gtttaaaaat caacaaaacc gccaatccag ctactttcag tcaagacaat   1260

gaaatatcta cggacaatag aattggtact ggtaacatca atgccatgga gatcaacatc   1320

caggcgaatc tgtggcggag tttcttgtat tccaacgtgg ccctctacct gcccgactca   1380

tacaagatca cccccgataa cgtggccatc tctgacaatg aaaattcata cgattacatg   1440

aacgggcgca tcgccccgt aggtctgatc gattacttca tagatatcgg ggcccggtgg   1500

tcgcccaacc ccatggacaa cgtcaacccc ttcaaccacc accgcaacgc ggggctgcgc   1560

taccgttccc agatcctggg caacggccga tacgtaccct tccacatcca agtgccccaa   1620

aagttctttg ccatcaaaaa cctcctcctg ctgcccgggt cctacaccta cgagtggacc   1680

ttccgcaagg acgtcaacat gatcctgcag agcacgctgg gcaatgacct gcgagtggat   1740

ggcgccaagg tcagcatcga cagcgtcaac ctctacgcca acttcttccc catggcccac   1800

aacaccgctt ccaccctgga agccatgctc cgcaacgaca ccaatgacca aaacttcaac   1860

gactacctca gcggagccaa catgctctac cctatcccgg ccaacgccac caacgtgccc   1920

atctccatcc cctcgagaaa ctgggccgcc ttccgaggct ggagcttcac ccgcatcaag   1980

gccaaggaaa cccccctccat cggggccggt ttcgacccct atttcaacta ctcgggcacc   2040

attccctacc tcgatggcac cttctacctc aaccacacct tccgccgcgt ctccatcatg   2100

tatgactcct ccgtcagctg gccgggcaac gaccgcctgc tcacgcccaa cgagtttgaa   2160

atcaaacggg ccgtggacgg agagggctac accgtctgcc agagtaacat gaccaaggac   2220

tggttcctca tccagatgtt gagccactac aacatcggat accagggctt cttcgccccc   2280

gagtcctaca aggaccggct gtactccttc ttccgcaact tccagcccat gagcaggcag   2340

gtggtcgacc ccatcaacta caaggactac aagaaggtca ccgtgcgcta ccagcacaac   2400

aacacgggct tcacgggcga tgtcaccccc gcggccatcc gggagggaca cgcctacccc   2460

gccaacgccc cctacccct catcggggcc accgcggtgc cctcgctcac ccagaaaaag   2520

ttcctctgcg accgcgtcat gtggcgcatc cccttctcct ccaacttcat gtccatgggc   2580

gccctcaccg acctggggca gaacatgctc tacgccaact cggcccacgc cctggacatg   2640

accttcgagg tcgaccccat ggacgagccc accctgctgt atgtcttgtt tgaagtcttt   2700

gacgtggtcc gcgtgcacca acctcacagg ggcgtcatcg aggccgtcta cctgcgtacc   2760

ccattctcgg ctggtaacgc caccacataa                                    2790
```

<210> SEQ ID NO 10
<211> LENGTH: 2445
<212> TYPE: DNA
<213> ORGANISM: Titi Monkey Adenovirus

<400> SEQUENCE: 10

```
atgagcgact ccgtcatcag catggaagac tttgaaccac cccagcaaga tcaatcgaca     60
gcaccaccca ccgatgatga cgtgcccata gaatcagacg tggagttcct cactgaggag    120
cagcaccgcc tgcgtctaga gcaggaggct gatcagcaga taatgaagaa agagcaggaa    180
acccagacag aggatgagca ggcaaatcat gacgcagttc aggaggagga tgattctggg    240
gagaagcagc agcagcgaca tggcgatggc tacatcacag acgagatcct gctgacacac    300
atcgcgcgcc agagtctcat cgtgcaagac gccctggccg accgcagcca gatccccctc    360
accgcccgcg acctcaccga ggcctacgag caatgcctct tctcgccgcg cgtgcccccc    420
aaacgccaac ccaacggcac ctgcgagccc aacccccgtc tcaacttcta cccgcccttc    480
gtcgtgcccg aggtcctcgc cacctatcac atcttcttcc aaaattgcaa gatccccctc    540
tcctgccgcg ccaaccgcac cgcggccgac gagcgcctcg ccctcggcga aggggatagc    600
atacctgata tcgcctccct ggaagaggtg cctaagatct tcgagggtct cggtcgcgac    660
gagaagcgcg cggcaaactc cctgcaaggc aacggagacg gagaagagag tcagtcggcg    720
ctcgtggagc tcgaaggcga caacgcccgt ctcgcggtgc tcaaacgcag catcgatgtc    780
acccacgcgg cctaccccgc catcaacctc ccgcccaaag tcatgtcggc cctcatggat    840
cagctgctca tcaaacgcgc ggcccccatc gacgccgaac gcgaaacata caaccccgac    900
gaggacgaca gcgaggacgg caagcccgtg gtctccgacc aggagctcgc tcgctggctc    960
aacgtggccc tcgactcccc cctgctggag gaacgacgca agaccctcac cgccgtcctc   1020
ctcgtcaccc tcaacctcga atgcctgcgc cgcttcttct cccaccccga caccctgcgc   1080
aagctggaag agtccctgca ctacaccttc cgccacggct acgtcaggca ggcctgcaag   1140
atctccaacg tggagctctc caacctcgtc tcctacatgg gtatcctgca cgagaaccga   1200
ctcgggcaga acgtcctcca ctccaccctc aagggcgagg cccgtcgcga ctacatccgc   1260
gactgcatct acctctacct ggtctacacc tggcagaccg ccatgggcgt ctggcagcag   1320
tgtctcgagg agcgcaacgt ccaggagctg gaaaagatcc tgcagaagca gcgtcgcgcc   1380
ctctacacgg gcttcgacga gcgcaccatc gccgccgaac tggccaccct cgtcttcccc   1440
gagaagctca tgcagaccct gcagaacggc ctgcccgatt ttgtcagcca gagcatgctg   1500
cacaacttcc gcagcttcat cctcgaacgc tcaggcatcc tcccggccat gtcctgcgcc   1560
ctcccgtcag atttcgtccc catctccttc cgcgagtgtc ccccgccgct gtgggcctac   1620
acctacttgt ttcagctggc caactacctc atgtaccaca gcgacgtggt cgaggacgcc   1680
acgggcgagg gtctcatgga gtgtcactgc cgctgcaacc tctgcacccc ccaccgctcg   1740
ctgatttgca accccgcgct gttgagcgag agccaggtca tcggtacctt cgagattcaa   1800
gggccagacg ccaaaaagca agaggccggt gaggaaacgg ccgtgggatc cacctccggc   1860
ttcaaactca ccgcgggtct gtggacctca gcctacctgc gcaaatttgt acctgaggac   1920
taccacgccc acaccatcaa gttctacgag caccaatccc cggtcaagag ccgggtcgaa   1980
ccctcggcct gcgtcatcac ccagagcagc atcgtggccc aattgcaagc catccaaaaa   2040
gcccgcgagt ccttcctcct gaaaaagggc aaaggggtct atctggaccc ccagaccggt   2100
gaggagctca accccccttcc ccccgccgcg cagttatccc tcagagatgg ccccgcgaaa   2160
gccggctccc gcgaagaagc aacctccacc accgccagtc caccccatct gggaggacga   2220
cgaggaggag tacacggagg acgaggagga cctgctgaca gacgaggagg acatggaggg   2280
tctggaagac atcgaggagg aagacgagga ggaggatctg gacgaggatc cgcaggagga   2340
```

gcccagggag caggcggttg cagacagcca gcacctagcg cccagggccc ctcaggcggc 2400
tcctgccccg tcagcagcag cagctccttc caagagtcgc agtag 2445

<210> SEQ ID NO 11
<211> LENGTH: 1830
<212> TYPE: DNA
<213> ORGANISM: Titi Monkey Adenovirus

<400> SEQUENCE: 11
atgaggagta tgatgactac gaggacgaag acgggctcat ggactagaat ttttttgtta 60
gggcaggaag cgagcaagat ggaccccaac ccaccaccac cacgtcagct gaaccccgag 120
gcccgggcgg tcgtgcagag ccagccttcg gcgcccaccg cctccgacga ctgggatggc 180
atgatgcagc ggatcatggc gctgacggcg cgcaatcccg acgcgttccg gcagcagcct 240
caggccaacc gattcgcggc catcttggaa gccgtggtgc cctcgcgccc cgaccccacc 300
cacgaaaagg tcttggccat cgtcaacgcc ctggcggacg cgggggccat ccgtcccgac 360
gagggtgggc agatctacag cgccctcttg cagcgcgtgg cccgttacaa cagcaccaac 420
gtgcagacca atctggaccg cctggtcacg gacgtgaagg aggcggtggc ccagcgcgag 480
cgttatttca aggagggcaa tctcgggtcc ctggtggccc tgaacgcctt catcggctcg 540
ctgccggcca acgtggtccg cgggcaggag gactacacgg ctttcatcag cgcgctgcgg 600
ttgatggtgg ccgaggtgcc ccagagcgag gtctaccagt cgggacccca atactttttc 660
cagaccagtc gtcagggctt gcagacggtt aatctgacgc gggcctttga gaacttgcat 720
cagttgtggg gcgtcaaggc cccgtgggc agcgaccgct cgaccatctc gtccctgctg 780
acccccaaca cgcgcctgct gctcttgctc atcgcccct tcacggacag cgggctgatc 840
tcccgcgaca cttacatcgg ccatctgctg accctgtacc gggaggccat cggccagaac 900
cgggtggatg aaagcacttt ccaggagatc acgagcgtga gccgggccct gggccaggag 960
gaccccggca gcttggaggc cacgttgaac tttttgctga ccaacaagcg gcagcgtatc 1020
cccacccagt acgccctgaa cacggaggag gagcgcatct tgcgctacgt gcagcagtcg 1080
gtgtccctgt atctgatgcg cgagggggcg agtcccaccg ccgcgctgga cctgacggct 1140
gccaatctgg agcccagctt ctacgccagc aaccgggcct tcatcaaccg cctgatggac 1200
tacttgcatc gggcggcggc cattaatccc gattacttta ccaacgccat tctgaacccc 1260
cactggttgc cccctcaggg ctttttcacg gggagtttg acctgcccga ggccaacgat 1320
ggctttttgt gggacgatat cgacagcagt ctggtggcca agaaggaggg cggtgacgag 1380
cagagccggc gcacgagcct ggcagacctg gggcggcta gcagcttccc cagcttgggc 1440
tcgttgtttg agagtagcag cagttcagct agcagcagca gacgcccgag ttctagtacg 1500
gggcgggtga cgcggccgcg gctgccgggg gaggacgagt acctgcgcga ccccctgttg 1560
ctgcccagtc gggacaagaa ctttcccaac aacggggtgg agaccctggt ggataagctg 1620
cggcgttgga agacctacgc ccaggagcag cgcgagttga ctcagggcgc gcggccccgg 1680
gaccctcggg atgactcagc gtggcatcag catcggcgcc agcgggagta tgacgaggac 1740
gcggctagcg acagcagcgt gttggatctg ggcgggagcg ggaacccctt cgcccacctg 1800
atgccccgcg gcgggagtcg gcgtctgtaa 1830

<210> SEQ ID NO 12
<211> LENGTH: 1641
<212> TYPE: DNA
<213> ORGANISM: Titi Monkey Adenovirus

<400> SEQUENCE: 12
atgcaacgca gtgtgccggt gcccgcgagc ccacctccgt cttatgagga ggcgatggcg 60
tcagtggggg cggtgcttcc tccgccggtg atgcaggctc cgtacgtgcc tccgcgctac 120
ctggggccga cagaggggcg gaacagcatc cgttactctg agatgcaggc gctgtacgac 180
acgacgcggc tgtacctggt ggacaacaag tccgccgata tcgcgtccct gaactaccag 240
aacgaccaca gtagtttctt gacgagcgtg gtgcagaaca gcgactttag ccctcaggag 300
gcgagcacgc agacggtgaa tctggacgag cgctcgcgct ggggcgggga gctcaagacc 360
atcctgcaca cgtgcatgcc caacgtcaac gagttcatgt tcagcaacag cttccgggcg 420
aggctgatga ctcagaaaaa gaatggggtg gccgagtaca agtgggtgga gctgaccatc 480
cccgagggca atttcagtga gatcatgacc ctggacctga tgaataacgc ggtggtggag 540
cactatttgc aagtggggcg tcagaacggg gtggaggagg cggacatcgg ggtgaagttt 600
gacacacgca acttccgcct ggggtacgac ccggtgacga agctggtgac gccgggcagc 660
tatacgtacg aggcctttca tcccgacatc attttgctgc ccgggtgcgc ggtggacttt 720
acctacagcc gcctgagcaa cctgctgggc atccgcaagc ggcagccctt ccaggagggt 780
ttcatcatcg agtacgatga cctggtgggg ggcaacatcc cggctctcct cgacgtggcg 840
gcctatgaag gtagtctgca gggtggcggt ggcagcggcg gcggatcgac caccgcggcc 900
gagacgcgag acgggcctgc tgaagacgct gacggccccg tcctcgtgga cgctgatgac 960
gtggagtacg agatgcgcgg cgatggtcac atggtccgca agaggcgtag cgcctcacct 1020
gtggcggagc ctgcggcaga tcctatccct aacagccccg ttatcaaacc aattacaaaa 1080
gactcaaaaa accgaaccta ccatgtagac gaggtaacca accagacggc ctaccgcagc 1140
tggtacctgg cctacaacta cggggacccg gagaagggcg tgcgctcgtg gacgctgctg 1200
acgacgcccg acgtcacgtg cggctcggag caggtctact ggtcgctgcc cgacatgatg 1260
gtggaccccg tgaccttccg cccctcgcag tcgcccagca actacccggt ggtgggcgcc 1320
gagctcatgc ccgtgcagtc gcgcaccttt ttcaacgacc aggccgtcta ctcgcagctc 1380
atccgccaga acacctccaa gacgcacgtc ttcaaccgct tccccgacaa ccagatcctc 1440
gtcaggcccc ccgcgcccac catcaccgcc gtcagcgaaa acgtgcccgc gcacaccaac 1500
cacggcacgc tggccatgcg tcacagcctg cgcggcgtgc agcgggtcac cgtcaccgac 1560
gccaggcggc gcacctgtcc ctacatctac aagaccttgg gcattgtcac cccgcgggtc 1620
ctctccagtc gcacctttta a 1641

<210> SEQ ID NO 13
<211> LENGTH: 1533
<212> TYPE: DNA
<213> ORGANISM: Titi Monkey Adenovirus

<400> SEQUENCE: 13
atgagcgacc aaccgcccca gcagagcacc agcagcagca accagccgca ggaggaggga 60
aatcccccgc ctccgctgcc ccccaagcgg agccgccgca agcagaagct ggaaacgaaa 120
ccggagctgc ctccgtcgcc cgtgagcgtg agcagcggaa gcagcagcga agaagaggaa 180
gagccggcgg cagagcccga gatcgtgaag gtgctgttta ccaacccgcc caccgtggtg 240
cacgccgacg gaagcaagga acgcatcagc gagcagcagc tgaagagacc cacgagcctg 300
gacttgagcg ggaacgctcc tcttaaaaaa aaaaagatgg acccgagcaa ggggcagacg 360
gagggttcga acacgggtcc ctctgttacc tcgggggcag cgagtgctac gactgccggg 420

```
tccagcggcg ctggctccgt agcgcttttg agtgttggga gggccgttcc ctttgaggct    480
tacaccaccg ctcagaacat gctggtcacg ctgaccaaca agttcaaggt gcagctgccc    540
ccggagggct tgaatatgag cccggtagat tctgagatga tgtccaaggt ctgtcagagc    600
tggctgaatc agagccacaa cacgccccag ctgaccttca cttcttacaa gagcttcgtc    660
cacataatgg gacgcatgct gtggcagctg gtggccaact ttgcggagtt gcgggtggag    720
cccgagggct ggaaccccac ggggtgtgtg atgtgggacc accagagtgc ggtgaaggag    780
ggggaggtga agtgcctgca cggcatgatg atgatcagga aggagcagac ggtggagatg    840
gatgtaaata gcgagaatgc ccaacgggct ttgaaagagc agccccagaa ggccaggatt    900
gcccagaacc gatggggtcg taacgtggtg cagttgcgta acgaggaggc ggtggtgtgc    960
ttgcacgacg cgagcaaccc taacggggtc tttagcaacc tgtcttgcgg aatgtcctac   1020
tctgacgtca ccaaggcgca ggtgggtttc caacaggcgg cggcgttcat gcgggcatgc   1080
taccctcagg ccaagaaggg tcgcgactgt ctgttactgt gcatgacctg cttctgcaat   1140
caccaccccc gctcggggcc gctgagcgga cggcaggtgt gcaagctgac cccctttaac   1200
attcccaact cggagggtat cgaccccgag gagattcggg atcccgtgat gcgggccagc   1260
gccaagtacc ccgtggtgct ggtgagccag tgttgcaacc cggtgtatcg caataccaag   1320
gccaaccccc agcgcaattg cgatttcaag atctctgccc ctgacctgat caccagcgtg   1380
cagctggcgc gcaacatgtt tttggaggtg tttgagggcg agcggcttcc ccccctgaaa   1440
ttccccgagc acaagtggtc cccccgcttg cagtaccgca acgtcgcttt ccccgcggcg   1500
gtggacgacg ggtgccaaga cctgtttgat tga                                1533
```

<210> SEQ ID NO 14
<211> LENGTH: 1518
<212> TYPE: DNA
<213> ORGANISM: Titi Monkey Adenovirus

<400> SEQUENCE: 14

```
atgaagcggg cgcgggtgga agtggaaggg gacttcaacc ccgtgtatcc ctttgataag     60
gatgacgaac aggacaatca agacgtcaac agcaccctcc caccettcct ctcctccaat    120
gggctcactg aatccccggc ggggttcctc gccctgaaaa cttccaaccc catggatttc    180
actgacaaag gcgcactcac agtcaaaacc aatcccccca tagaggtcaa ttcaagtgga    240
cagctcagtc tcaaattagg atctggtctc acagtctctg ggggggcact gcaggccatg    300
ggtgagaccg tctcagtcac agctcccatc accaagacta atggaaacat aggcttacaa    360
ctggccagta acccaggcct gcaagtcagt aatggtttaa agcttaaagt cacagcacca    420
ttcaccctca ataataatgg tctgaacata ggcgtggacg cgccactcag aatacaagat    480
aacaaacttc aattatccac gggaaatggc atagaagttg ccagtaacag aacactggct    540
gttaaactta aagaacagg aaacaacaat caaggattag actttgatgg tgtacagcta     600
gtcttaaaat tgggagatgg gttgaaatta ggcaacactg ggtatgttga cataagatta    660
ggaaatgcca ataactgtgg cttacaactt gaaaacgggg aattaaaatt caaaatgggg    720
gatggactga tttatggcaa cacaggatat gttgatgtca acgttgggca aggtatagag    780
attaatcaaa gaaaggttaa agtgaaaaca gcagaaggcc tagccttcga caaccaaaat    840
aggttaaaaa tcaagtgcaa taccccacta ggatttgatg gcactggtaa tttgaaagtg    900
ggtttaggag atggcctcta tatagccaat gataaaattt tttatgaagc tcccacacta    960
tggacaaccg catctccaca aactaatgcc aatgtgagat ctgaaagcga taatcaaaca   1020
```

```
actaaaaatg ctaaagtgca gctgacccta tccagatgtg gagccatggt tctagggtac   1080

atctcagttt atggcactgg agccccccctc attcccatca atacaggtac tacgactaat   1140

ttaagactat tgctagcctt tgatggagag ggtagattag ttaatggtaa taacatgctg   1200

acgtcctctt tagaagtgaa ggcaggagcc acagttaatg catcatcagg aatagacagg   1260

agaatcttta tgcccaataa aggttcctat ctaaactcag gctctgattc aggacaggct   1320

cacaacgcca tatttagaaa ggtctacctt aacaaagaca taaataaaac atgtgatcta   1380

actctaacat taaatgaaaa cagagcaaat ggacaatatt cattatactt taagtggacc   1440

aacttcagcg ccagtgttaa taatcaaacc ttttccacct gtgtaaccca ctttgtctat   1500

ctgggtgaaa atccatga                                                 1518
```

<210> SEQ ID NO 15
<211> LENGTH: 993
<212> TYPE: DNA
<213> ORGANISM: Titi Monkey Adenovirus

<400> SEQUENCE: 15

```
atgcatccgg tgctacgtca gatgaaaccg ccggcgacgg cgaccgcctc gtacccaccc     60

ccgcccacca cggcccaggc ggcggtagct agtggagccg gcgcggcagc agcaggagga    120

ggagagctga cggggggtcg ccgcgtgccc gagggtcttt tggacgaggg cgagggtctg    180

gcgcgtctgg gggcgcacga ccccgagcgg cacccccgcg tgcagctgaa gcgggacacg    240

cgcgaggcgt acgtgccgcg acgcaacgcg ttcagggagc gtgagggcca ggaacccgag    300

gagatgaggg atttgaggtt tcgggccggt cgggagttgc atgatctgga tcgcgagcgg    360

gtgctgcgat cggaggattt cgaggtggac ccgcggacgg gcgtgagtcc cgcgcgggcg    420

cacgtggagg cggccaacct ggtgagcgcg tacgaggaga cggtgaagca ggagatgaac    480

tttcagaaga gtttcaacaa ccacgtgcgc acgttgatcg cgcgcgagga ggtggccatc    540

gggctgatgc atctgtggga ctttgtggag gcgttcgtga gcaaccccaa cagcaagcct    600

ctgacggcgc agctgctgct gatcgtgcaa cattcgcggg acaacgaggt gtttagggag    660

gcgctgctga acatcgccga gcccgagggt cgctggctgc tggacctgat caacatcctg    720

cagagtatcg tggtgcagga gcgttcgctg agtctcgggg agaaggtggc cgccatcaat    780

tatagcatgt tgagtctggg caaacactac gcccgcaaga tttacaagag ccccttcgtg    840

cccatcgaca aggaggtgaa gatcgatagc ttttacatgc gcatggccct gaaggtgctg    900

acgctgagcg acgacctggg cgtctaccgc aacgaccgca tccacaaggc cgtgagcgcc    960

agtcgccggc gcgagctcag cgaccgcgag ctg                                 993
```

<210> SEQ ID NO 16
<211> LENGTH: 1191
<212> TYPE: DNA
<213> ORGANISM: Titi Monkey Adenovirus

<400> SEQUENCE: 16

```
atgaccacgc gaaagatcaa agaagagctg ctgcaggcgg tggcgccgga ggtgtacacg     60

ccgctggtgg tgcccaagcg ggagattaag agggagttga aaagggagat caagggcgag    120

ctcaagcggg agcgggggga cgttaagccc tttagaagca ggaagcgcaa gaaggacgag    180

gacggcgacg tcctgctagt gggcgccccc ggcaccgagg gggtggagtt tgtcagggag    240

tttgccccgc ggcgacgagt gcagtggaag ggacgcaagg tgaggccttt cttgcggccg    300

ggcgcggtcg tgcagttcac cccgggcgag cggtccacat ggcgcctgca caagcggagc    360
```

```
tacgacgagg tgcacacgga cgaagacatc ctgcaacagg cggcggcgtt ggacaacgag    420

ttccgctacg gcaaaagacc ccgaccctac gaggatctca tgatcccgct ggacgagggc    480

aaccccacgc ccagcctcaa gcccgtcacc ctgcaacaag tgctgcccgt ctccaccacc    540

acggaccgca aacgcggagt caaacgcgag cggctgggcg acctgcagcc caccgtgcag    600

ctcatggtgc ccaagcgccg caagatggaa gacatgctcg aagacgcctt catggacccc    660

gcggagcccc ccgaggtcaa gatccgaccc atcaaggcgg tggcgcccgg catcggcgtg    720

cagaccgtgg acgtggagat cccccctgcga caggcggccg ccgccgtcgc cgacgtggac    780

atgggcccca gcgtgcaaga agtgggcacg gaccccattc cccagccgcc ggcccccgtg    840

tcctccctga tcccgatggg agcggccgtg gcagcggctt ccaagacggt ctcggcgggg    900

acgcagacgg accccctggat gggggcgccc gtgcagcccg cccggcgccg tcgccgctac    960

ccgaccgcca gctcggtgat gcccaactac ttgttgcatc cgtccatcac cccgacgccc   1020

ggctaccggg gtcgacgggc ccctcgccgg cgcgccgccg cctcgtcttc ctaccgcagc   1080

cggaggagac ccgcttcgcg ccggagccgc gcggtgaccc gagtggtgac ccgccgcggg   1140

aggcgcctga ctctgcccgc cgtgcgctac catccgtcga tcgtcttgta a            1191
```

<210> SEQ ID NO 17
<211> LENGTH: 942
<212> TYPE: DNA
<213> ORGANISM: Titi Monkey Adenovirus

<400> SEQUENCE: 17

```
atggccaacc cacgtctgct caccgtcctc gcttgtctcg ctattcttct tacctttcta     60

ccactctgtc aaactacttg ccatgaaaga gatttcgagg ttgaaatagg cggagattta    120

gacattgatg tattccaagt ttttgaacat tggcatatca cctttaaaag gttgtacaac    180

agaactgttg gccaacgttt agtatgtgat agcagctcag gtcctactga ctatggtttt    240

tcttttaatg accatttttt acaactcaga catgccacca aagatcacat tggcattttt    300

acgctggaag tggaatacaa tgaccccaca tactggtttc cagcagtagc aagatgtcct    360

attaacatta ctctggttga tttcactgaa ccaaaatgta ttctgggatg cactgttgaa    420

gaccatggct tcattaaaga tgtaatgctt atgtgcaaca caagccatga cataataatg    480

acagttgtca gcgatactgt ttcgactgac atgcaccacc gtttttttagc tactgcttac    540

acttcaaatt tagtcatttt agtggtggct ttcaataatc agtctactgc aattacccac    600

tttgtaatga cacctccatg gatcaatgac accagctgtc ccaatctcat tactattaac    660

atcacaacaa gacacggttt caatgacaac agtgaatggg aagaagttgg acagcttggg    720

ttttcacaca gtgcacagtc agatgctgtt tgtgatcacg accacacttc ctacattttg    780

atcatcgtca tcgccttcct cttcatgcta gcagagctgc tctttatcct ctacctctac    840

cacaagtact tcaactgggg cagggggtac agagggccgc ccatcatcct cgaaaacaaa    900

tctgacgcac ctgcccccaa atattcctac aggtatgcct ag                       942
```

<210> SEQ ID NO 18
<211> LENGTH: 884
<212> TYPE: DNA
<213> ORGANISM: Titi Monkey Adenovirus

<400> SEQUENCE: 18

```
tggaagatat caatttttct tccctggccc cgcggcaagg ctcgcgtccc ctgatgggcg     60

cgtggggtga gatcgggacg aaccagatga acggcggggc cttcaactgg ggcagcatct    120
```

```
ggagcgggct gaagagtttc ggctccacgg tgaaaaatta cggtagcaag gcgtggaaca    180
gcaccaccgg gcagatgctt cgcgacaagc ttaaggacac gggggtgcgg gaaaagatcg    240
tggagggcgt cacctcgggc atccacgggg cgctggatct ggcgcgccag gagatggaga    300
agcatatcaa ctcccgcctg gaccatccgc gtcccgacgt ggaggtcgag gagatgctgc    360
cgggcttgaa cgagaagccc cccctggccc cgtcggcgcc tcccaaggag gaccgtctgc    420
ccgagaagcg tccccggccc gaggctgagg aggagctggt gatccgcacg gacgagaagc    480
cccccagcta cgaggagatc tttggcaagg acatggcgcc cccgcccccg gtggcctcca    540
cgtaccccat gacgaagccg atcgcccccc tggcgcggcc ggtgatcggg acgtcttcta    600
gcaacaagaa agtgcccccct ccgcgtcctc caccgcccac gagacgtccc accgtcccgg    660
ccgtggcccc cgcgggtccc gtggatgttc cggtgacctt ggatcttccg ccgccgccgt    720
ctgccgtggt gactccggct gctccgcctg tggccatcgc gacccccgcc accccggccg    780
cccgtccctc gtactctcgc cccagccgcc agagttggca gtcgaccctg agcagcatca    840
cgggtctggg agttaggagc ctgaaacgcc gccgctgtta ctaa                      884
```

```
<210> SEQ ID NO 19
<211> LENGTH: 882
<212> TYPE: DNA
<213> ORGANISM: Titi Monkey Adenovirus

<400> SEQUENCE: 19

atggatcaac ggaaccctca accgcctccg ggccccttgg cccctttca tcagcatcag     60
ctacctctcc cggaccccga tcccccagcc caaggtgaat gtttcgcccg gcgctgtgac    120
accaacaccc tgcacgatgt gatcacggta agatcggtcc cgtccagtgt gatgtttaca    180
gtgtacttgg aatggccggc tccgttccat ttctttttga gcccgtatga acaacatctc    240
atgagacagt acatgcatgt gtgtgcttgt cccgcgacgc tggtcattgt ccactgtcgg    300
atgatcaggg gctcggaggt gtggatgttg cattgtcact gtagccgccc ggggtctctg    360
cagtgtcggg cgggggcggt gttgttgagg agatggttct atctgttggt ggtgggatcc    420
ttggtgaatc tgaggatccc gtggtaccgc ccctgggtga acgaccatat gcccaaggag    480
atgatgtatg tgggcagcgt gtatgtgagg ggactgcatc tgatttacat caacgtgaga    540
tacgatgagc atgccgagca cctgatcagg actgtgaatt ttggactgtc tgctttccat    600
tatggggtga tgaacaacat gctggttctg gtctgctcgt actgccgcac gggcgaggag    660
atcaggttca ggtgttgcgc cagacggacg cggcgcctgc tggctcgctc ggtgcgggaa    720
ttggacagta tttcccgtca tcctttgagg gcgagccgga ccgagcggca gcgccagcgg    780
atgtttgaca gcgtgatgtg gcggtcccgg gcgctgagtt atgatgtgta tgaccggtgc    840
cgcaacgtgc gaccgtaccg ccctccttct caccgcagat ag                        882
```

```
<210> SEQ ID NO 20
<211> LENGTH: 750
<212> TYPE: DNA
<213> ORGANISM: Titi Monkey Adenovirus

<400> SEQUENCE: 20

atggctagca acgggagctc cacctcctct ggagtcagtt ttgacggggc cgtgtacagc     60
ccatttctga cgtgtcgcct gcccacttgg gcgggagtcc gtcagaatgt catcgggtcc    120
accatcgatg ggagcccggt gcttcctact aacgcatctt ccatgcgtta tgagacagtt    180
agcgcgacgg gcggccaggc aactctgcct atttctagct tcgggactcg tgttctacct    240
```

```
gcagatcctg cagcacgctt ctcgacgatc cagaccccg cggcagccta cgcggcggca    300

gcggcggctc gcaacgcaga cttcgaagaa cgcatcgtcg cgggactgac ggatctggcg    360

gagaagatta acctgctgaa cgtgcgccag gagatggacg agcgcgcctt ggacaccgtg    420

ggagccgaca tcgtgcagct gaagcagggc ttggaattct tcgcgcagcg tgtggaggcc    480

ctgaccgggg ctgtgactca gctccaggaa caggtccaac agctgcaaga ggccgccagc    540

gccgcggctg tcgtcattcc cgccactcct gcttctcccc agcctgtggt tccaccagca    600

gctgctgccg aggttgtgcc gctgcccgtc acccccctg attccccgca tgcagccgcc    660

cccaccgctc cacagcctgc cgagaccccc gtggctgcac ccctcacctc tcccgcttcc    720

cccgcccccg ctctcaaccc tgctgtgtaa                                    750
```

```
<210> SEQ ID NO 21
<211> LENGTH: 711
<212> TYPE: DNA
<213> ORGANISM: Titi Monkey Adenovirus

<400> SEQUENCE: 21

atgaagagct gtttgagcgt ctgtgtacta tcttcaatac ttctacttgc cctcagcagt     60

gagttaataa acttgaactg cactgaacaa ccagccactc ggggtgatct gttctacaac    120

gccaacgggt cactgatcgt cttccttcag tgtcccaacc actccagcct ctcctacccc    180

atccactggt cttacaactt ctccgtcccc gtcgccaact tcaccccggc cgtcaacgcc    240

actcgacagc cgcctctgct cgcccatcag ggttggaacg agaccgtcgc caacggggtt    300

gagtctgtga tcgtcctcga gaacccaccg gagggcgtct actgctgcct ctccaacctc    360

accgtctgca gttgctggaa cttcactgac ttcaaccgca ccctcgaggg cttcagcacc    420

accaccaccc ttgctaccac tactacctcg gtagaaacca ccagcaccgc cgtcgccacc    480

actaccgcca ccgtcgacct cccactaccc gagggagctc aggaaggaca ggacttttac    540

tttgtggagg agagggaaac tcatctccag ctagactcca agttctggac tggtctgact    600

ctgggactag tgctcttcgt ctccttggtt ctcctctgcc tggtggaata caggcgaaac    660

caagtcggtg attcctacac cactcaggag cctctcttgc acacagtctg a            711
```

```
<210> SEQ ID NO 22
<211> LENGTH: 683
<212> TYPE: DNA
<213> ORGANISM: Titi Monkey Adenovirus

<400> SEQUENCE: 22

tgtccaaagt gattcccacg ccttacatgt ggagctacca gccgcagatg ggactggcgg     60

cgggggcgtc ccaagactac tccacgcgca tgaactggct cagcgccgga cctagcatga    120

tcgcccgggt caacggggtc cgcgacgagc gcaaccagat cctcatgaag caagcggcca    180

tcaccgccac gccccgaggg actctgaacc cgccaagttg gcccgcggat ttggtgtacc    240

aggaaacgcc gccgcccgac accgtgctcc tcccgcgtga cgcacaggcc gaagtccaga    300

tgacgaattc gggtgcccag ttggccgggg gcggagtcag gttcacgccc taccgccggc    360

cgggcataaa taccctgcgc tttcggggca gaggcgtaca gctcaacgac gagacagtca    420

gctcctcgtt gggattgaga ccagacggag tcttccaaat cggaggatcc ggcctctcgt    480

ctttcacacc tcgccaggtc tacctcaccc tccagaccgc ttccagccgg cctcgctccg    540

gtggcatcgg aaccctccag ttcatcgagg agttcgtgcc ctcggtctac ctcaacccct    600
```

tctcgggaca ccccggtcac tacccggacg acttcatccc caactacgat gccgtcagcg 660
actcggtaga cgggtatgac tga 683

<210> SEQ ID NO 23
<211> LENGTH: 667
<212> TYPE: DNA
<213> ORGANISM: Titi Monkey Adenovirus

<400> SEQUENCE: 23
ttttctctca atggatctct tgaagttcct ggaagacttt gagaattgca gacaagtttt 60
gcagcaggcg tccaagagga ctgggggttg gagccgctgg ctgcttggca atcagctggt 120
tcgcacggtc gctcaggtca agacagacta tagcgagcat ttcgagcagc ttttgcagga 180
gcagaaccga cttctgctga acaacttgga actcggtcac accagggcac tgaacggtgt 240
gctgagggaa ctggactttg agaatacggg acgggtggta gctggtcttg ctttcctcgc 300
gtacctgctc gatcggtggg acgagaacag cgtcctcagc ccgggctacc gcctcgattg 360
cttggccctc gcgatatgga agcacacgct gagggagggg atcctgagag ggtgatgca 420 ggggccccgg gcgcgggtga accgggagat caggcgggag gtggaggagc ggctgacgca 480
ggtgcagcgg gagttggaag agagggagag ggagaggcag cagcgggaga gggagcagca 540
gcagcaggag ggggaaatga ctacgagcat atggaggcct tccatggagg cggagtggcc 600
gccgcgggcg gggatggacc ccccgctgga ggagcagtgg gaggcggacc acgacccgga 660
ggcataa 667

<210> SEQ ID NO 24
<211> LENGTH: 614
<212> TYPE: DNA
<213> ORGANISM: Titi Monkey Adenovirus

<400> SEQUENCE: 24
atgggttcca gcgaagagga gctcaaagcc atcgcgcgag atctgggctg cgggccctct 60
ttcttgggca ctttcgataa acgttttccc ggtttcatct ccccccacaa gctcgcctgc 120
gccatcgtca acaccgcggg ccgagagacc gggggcgtgc actggctcgc gctgggatgg 180
aaccccaaat ccaagacggt ctacctgttc gaccccttcg gcttttcaga tcagaggctc 240
atgcaaatct atcagttcca gtacgagagc ctcctcaaac gcagcgccct ggccagtacc 300
gaggaccact gcgtgactct ggtcaagagc actcagacgg tccagggacc ccacagcgcg 360
gcctgcgggc tcttctgctg tcttttcttg catgccttcg ttcactggcc cgaccgaccc 420
atgtctggaa acccgaccat ggacctcgtt gacggagtcc ccaacgccct cctcaactcc 480
cccaccgtcc aacccaccct gcgcaagaac caggaggccc tctacgcctt cctccgctcc 540
cactccgctt acttccgtca acacgagacc cagatccgcg aggccacccg cttcgataaa 600
gccctcaaaa tgta 614

<210> SEQ ID NO 25
<211> LENGTH: 593
<212> TYPE: DNA
<213> ORGANISM: Titi Monkey Adenovirus

<400> SEQUENCE: 25
tgtccattct catctctccc agcaacaaca ccgggtgggg cttagggacc aacaaaatgt 60
acggaggagc caagcgccgg tccagcgaat accccgtgct cgtcagacgc catttcaggg 120
ccccctgggg agcccgcaag ggacgcctac gtcagcgcac caccgtagat gacgtcatcg 180
acagtgtggt cgacgacgcc cgcgcctggg cggatgctca gccggccccc gcggccgtgg 240
ctgccgccgt gggtcgtcgg gtggccagac gggcccgtcg ccggccccgg gccagcgccc 300
gctccaccgt ggacgcggtc atcgatagcg tagtcagggg cgcgaggcgg tacgccgatc 360
gcaaggcccg tcgcgggcgt cgcagcgccg ccgtgtcggc cgccaggagg ctggtgcgcg 420
gagcccaccg cgtgtaccgc cgcaagctgc ggcgacggga cagtcgacgg aggggggccg 480
cccgggccgc ggccgctgcc atcagaagca tggcgccgcg ccggcgcaac gtgtactggg 540
tccgggacgc cacgaccggc acccgggtcc ccgtgtattc ccgccccaag taa 593

<210> SEQ ID NO 26
<211> LENGTH: 585
<212> TYPE: DNA
<213> ORGANISM: Titi Monkey Adenovirus

<400> SEQUENCE: 26
atgagggtct ggcaatacct cgtcaggggg ctcatgctct ctctgttttt tctcctcaaa 60
gctgcgagtc ccttcactta catcttctcc attctcccgt gggatcatat ggttaacctg 120
ccttgtcatg gggatgggtc tgtgggcccc tgtccccatt cccgggtcca cgaatggacc 180
ttcaacgggt cttacatagg ctccttccag tgctccaacg gggtgattcc taatgactgg 240
tctaacatct tagctggaaa cttcaccacc ttgtctgtcc tcaatccccc tcgaggaaaa 300
tactgctgca ctctcaggga tcgatacgag gaatgcttcg ggtgggctt agaatcctac 360 gtccaccagt tgggagccca tgataggaat gtctatgaag aaaccacctc tgctccttct 420
cttcccttct ccattatgcc ttccaatccc ggggagtttg tgctgctggt ctttctgttt 480
gtgtgcatgt tcttgggggc ctacctcctg taccgcatca ggcggctgta tgtgactaac 540
caggagtctt tttcttatgt tcaatttact aacagcccag aataa 585

<210> SEQ ID NO 27
<211> LENGTH: 569
<212> TYPE: DNA
<213> ORGANISM: Titi Monkey Adenovirus

<400> SEQUENCE: 27
tggccccgcg aaagccggct cccgcgaaga agcaacctcc accaccgcca gtccacccca 60
tctgggagga cgacgaggag gagtacacgg aggacgagga ggacctgctg acagacgagg 120
aggacatgga gggtctggaa gacatcgagg aggaagacga ggaggaggat ctggacgagg 180
atccgcagga ggagcccagg gagcaggcgg ttgcagacag ccagcaccta gcgcccaggg 240
cccctcaggc ggctcctgcc ccgtcagcag cagcagctcc ttccaagagt cgcagtagat 300
gggaccgcaa gccagctgcc gcgggtaagg gatcttacaa gtcttggcga gcccacaaag 360
cccgactgct gtggtgcctg ggcgagagcg ggggcgacgt gaatttcacc cggcgctaca 420
tgctcttcca ccacggagtc aacatccccc gtaacgtcat ccactactat catcaatcct 480
acagcggcag cgactgggcc gaaatcgccg cggcagccag cctcctcgag gaagggaaaa 540
accagcagca gcaacagcag cagaagtaa 569

<210> SEQ ID NO 28
<211> LENGTH: 453
<212> TYPE: DNA
<213> ORGANISM: Titi Monkey Adenovirus

<400> SEQUENCE: 28

```
atggtgcctt ttcttcccgc cgtccctgct cctcctctgg tacgcgaccg ccactctgct     60

ttggactggc ttcgcggcac tcgcgctttg gtggatgacc tcatcgctta ttgctctcgc    120

acgggctggg agttgacagg tcatcagtgg cgactgttga ccgggctgag tcagttgttg    180

gctcacgccg cctactttga gaggcagagg gtgacctcac cctcccggcg agtttcacct    240

gcggcttggc agcgggcctt cttttgcttt cggaaataca atctggtgcg ccgtcaactg    300

gatcagcagc gagaactgga atattcctgc ttgtattctt cttcttcgtc atctcatgga    360

tcaacggaac cctcaaccgc ctccgggccc cttggcccct tttcatcagc atcagctacc    420

tctcccggac cccgatcccc cagcccaagg tga                                 453
```

<210> SEQ ID NO 29
<211> LENGTH: 396
<212> TYPE: DNA
<213> ORGANISM: Titi Monkey Adenovirus

<400> SEQUENCE: 29

```
atggaacaga atcagactga cgtgcagcta gagatggatg gcctcatggc agagcagcgt     60

ctcctcctcc agcaagccaa cgaccgccac cgcaaaatga aaacagacga ggtcagaacc    120

tatgccaacc tgcaccaatg caagcgcggc aactactgcc tcgtcaaaca atgccatctc    180

gagttcacca cctgcgctaa cggggaccac gagctcatct tctccctacc ctgtaaccgc    240

ttctccagcg tctacaccgt gggtcagcac accgtcaggc tgggcatcac ccgcggtgag    300

acttcaggat ctatccgctg ctcctgccac aatcctgatt gtctacacac tctaatgaag    360

accctgtgtg gtctcaaaga taattgcccc atctga                              396
```

<210> SEQ ID NO 30
<211> LENGTH: 393
<212> TYPE: DNA
<213> ORGANISM: Titi Monkey Adenovirus

<400> SEQUENCE: 30

```
atggcgtctg tccaccgtcc tctgtggtgt ctgttgcaag cgcccgctcc cctggtgtct     60

tacctggagg ggcgtggctt tgacctgtta cgcctcctga aacaagagtt cgagcttttt    120

tggagatgtt ttctagacat gcgcggggag aggcagaacg tttacgtggg ggtacacgtg    180

ctgcagcggg agccggagct gagacttttg tgttgcgtgg ggacccagga gctagattca    240

gggacgccag agacccaggc ggtgttggaa gatctgctcg atgcgttaaa gcagcagatc    300

acctggcagg ctcatttgga gcagattacc gtgcctgatg gccttctgga tctgttgcag    360

gtttctgaag agcctgaggc gctcagcgac taa                                 393
```

<210> SEQ ID NO 31
<211> LENGTH: 351
<212> TYPE: DNA
<213> ORGANISM: Titi Monkey Adenovirus

<400> SEQUENCE: 31

```
atgaactgca ccctagactt ctacggaaaa atcttcttct ttagagaccc ctgtgaatgt     60

accaccatgg actatggcat ctacctcata tatgagatca tgctgctaat ctctgccggg    120

ttagcagcgg ctatcatgca cactaactac ctcaaactac catgggtaaa aagccccaat    180

tccaacgctc ctccctctcc accccccagc cctcctcctc agcctcctgc cgctgtcgct    240
```

ctcatccctc caccgccacc tccgcccccc gtgtacgcgc gagtagaccc cgacccgcca 300
ccagcctact tcgagatcta ctttggagac gatggaacag aatcagactg a 351

<210> SEQ ID NO 32
<211> LENGTH: 345
<212> TYPE: DNA
<213> ORGANISM: Titi Monkey Adenovirus

<400> SEQUENCE: 32
atgactgatg gagatctaga ggctgaagtt gaaaaagctc gcctccgcca tctcgtccac 60
tgccgtcggc ctcggtgcta cgcccgggac ctgctcctgc tcgagggttt cttctacccg 120
cccaaccatc ccgaaggccc cgctcacggc ctccgcctca ccgtacccga gacccagcgc 180
tcccgcctgg acaacttctt caccggtcgg cccttgctcg tcgagaccac ccacggaccc 240
gtgaccctca gcgtcacctg catctgcgcc gccacacagc tgcatgaaga gctgtttgag 300
cgtctgtgta ctatcttcaa tacttctact tgccctcagc agtga 345

<210> SEQ ID NO 33
<211> LENGTH: 309
<212> TYPE: DNA
<213> ORGANISM: Titi Monkey Adenovirus

<400> SEQUENCE: 33
atgctaattt tggtgtttga tgatgtcctg acgggcatcg ttaatggctg gaagcaggag 60
aacgagttgc agcagatcga tgagtgttct atgtattgtt tcgaggataa cgatctgaat 120
ccccagaagg tgacattttt gatttatctc aagcttcatc ttcctgcgtt ggtggatgcg 180
gtggtgtcgg gcttggagaa ccgtgtccat tttgatctgg cggtgaccta tcatcagcac 240
agcgggggac gcagatgcta ccttcgggac ctccagtttg aaatcctgga cgacctgctt 300
cagcagtaa 309

<210> SEQ ID NO 34
<211> LENGTH: 303
<212> TYPE: DNA
<213> ORGANISM: Titi Monkey Adenovirus

<400> SEQUENCE: 34
atgatcttta tgctcttaca gattttactg tctatgccgg aggtcgctcg ctcttgtata 60
ccggccttct gttcgggtgc ctgttggttt tgtggggcgt ctatcttcac tccagcggaa 120
cgtgagcacc cacagcctgt atgtggaggc cgatctggtg ccctgcaacc tcgaggccga 180
gttgaaaatc tgctggtgaa caatgggccc tttgactatc acggccgcgc gggggagccc 240
gtggcccgtc tagtcttaca gggcaccagt tttccgcaag tggtggaaat aactgagctc 300
tga 303

<210> SEQ ID NO 35
<211> LENGTH: 288
<212> TYPE: DNA
<213> ORGANISM: Titi Monkey Adenovirus

<400> SEQUENCE: 35
atgcctaggc cgtctgtcat cctcacagca gtcacagttc tccctgtgct ctgttctcta 60
gtggccctca gcgcatccaa ctccctccaa ggcacctgcc ttccctcctg ggccggactc 120
ttggccttcg ctttgcttaa catcacctgt ctgctcagca ccctctgctt cttcttctcc 180

```
ctcgcccaac tcattgacta cgcgagattc agaagaaatc acagactcaa tcgagaagca    240

ggaccagccg tcatcaacct catcaacctc ccccgcgccc aaccatga                288
```

<210> SEQ ID NO 36
<211> LENGTH: 246
<212> TYPE: DNA
<213> ORGANISM: Titi Monkey Adenovirus

<400> SEQUENCE: 36

```
atggcttcca aaatgacgtg ccgaatccgc atccccgtgc cctaccaccc gtcgagacgg     60

cggaggagag gcggactgag cgggagcggc ctgggtggtg gcgcccggcg gctgaggcga    120

cgacgggccg tgcgcggaca catgcgaggg ggctttttgc aggccctgat ccccatcatc    180

gccgcggccg tgggcaccat cccgggcatc gcgtcggtgg ccttgcaggc ttcgcggcgc    240

aactag                                                               246
```

<210> SEQ ID NO 37
<211> LENGTH: 186
<212> TYPE: DNA
<213> ORGANISM: Titi Monkey Adenovirus

<400> SEQUENCE: 37

```
atgagacccc ccaccgcgat gcacgtctgg tgcggttcca gtcttaccac cacccacctc     60

ccattcagcc tgtggaggaa gtatgccacc cgccggggtc tggagtacca gagctgggaa    120

gaggggcgct acgtggaggt gctagacaaa ctagacttgg gagacctgct gtcagatttc    180

aggtaa                                                               186
```

<210> SEQ ID NO 38
<211> LENGTH: 69
<212> TYPE: DNA
<213> ORGANISM: Adenovirus Probe

<400> SEQUENCE: 38

```
ccccgcgggg aagggatggg tgagggcgga ggcgtacatg ccgcagatgt cgtagacgta     60

gaggggctc                                                             69
```

<210> SEQ ID NO 39
<211> LENGTH: 70
<212> TYPE: DNA
<213> ORGANISM: Titi Monkey Adenovirus

<400> SEQUENCE: 39

```
tgccgtgggg catggggtgg gtgagggcgg aggcgtacat accgcatatg tcgaaaacgt     60

atacgggatg                                                            70
```

<210> SEQ ID NO 40
<211> LENGTH: 70
<212> TYPE: DNA
<213> ORGANISM: Adenovirus Probe

<400> SEQUENCE: 40

```
gtgccctttc acattcaggt gccccaaaag ttttttgcca ttaaaaacct cctcctcctg     60

ccaggctcat                                                            70
```

<210> SEQ ID NO 41
<211> LENGTH: 70
<212> TYPE: DNA
<213> ORGANISM: Titi Monkey Adenovirus

```
<400> SEQUENCE: 41

gtacccttcc acatccaagt gccccaaaag ttctttgcca tcaaaaacct cctcctgctg     60

cccgggtcct                                                            70


<210> SEQ ID NO 42
<211> LENGTH: 70
<212> TYPE: DNA
<213> ORGANISM: Adenovirus Probe

<400> SEQUENCE: 42

ccagcttctt tcccatggcc cacaacaccg cctccaccct ggaggccatg ctgcgcaacg     60

acaccaacaa                                                            70


<210> SEQ ID NO 43
<211> LENGTH: 70
<212> TYPE: DNA
<213> ORGANISM: Titi Monkey Adenovirus

<400> SEQUENCE: 43

ccaacttctt ccccatggcc cacaacaccg cttccaccct ggaagccatg ctccgcaacg     60

acaccaatga                                                            70


<210> SEQ ID NO 44
<211> LENGTH: 70
<212> TYPE: DNA
<213> ORGANISM: Adenovirus Probe

<400> SEQUENCE: 44

tcaagaaggt ctccatcacc ttcgactcct ccgtcagctg gcccggcaac gaccgcctcc     60

tgacgcccaa                                                            70


<210> SEQ ID NO 45
<211> LENGTH: 70
<212> TYPE: DNA
<213> ORGANISM: Titi Monkey Adenovirus

<400> SEQUENCE: 45

tccgccgcgt ctccatcatg tatgactcct ccgtcagctg gccgggcaac gaccgcctgc     60

tcacgcccaa                                                            70
```

ADENOVIRUS ISOLATED FROM TITI MONKEYS

CROSS REFERENCE TO RELATED APPLICATIONS

This application is a Continuation of U.S. patent application Ser. No. 13/469,011 filed May 10, 2012 which claims benefit under 35 USC 119(e) to U.S. Provisional Application No. 61/484,536 filed May 10, 2011, both of which are incorporated herein by reference in their entireties for all purposes.

STATEMENT AS TO RIGHTS TO INVENTIONS MADE UNDER FEDERALLY SPONSORED RESEARCH AND DEVELOPMENT

This invention was made with government support under grant nos. R56 AI089532, K08 AI074913, P51 RR000169 and R01 HD053555 awarded by the National Institutes of Health. The government has certain rights in the invention.

FIELD OF THE INVENTION

The present invention relates to the discovery of a new Titi Monkey Adenovirus (TMAdV), nucleic acids, proteins, vaccines, compositions, kits, methods of detecting and diagnosing TMAdV infection, methods of treating or preventing TMAdV infection, and methods for identifying anti-TMAdV compounds.

BACKGROUND OF THE INVENTION

Adenoviruses, first isolated in the 1950s from explanted adenoid tissue, are double-stranded nonenveloped DNA viruses that naturally infect many vertebrates, including nonhuman primates and humans. The human adenoviruses in the Mastadenovirus genus (comprised of all mammalian adenoviruses) are classified into 7 species groups A-G and 54 different serotypes (Harrach, B., et al. *Virus Taxonomy* (*9th Report of the International Committee on Taxonomy of Viruses*) (eds. King, A., Carstens, E., Adams, M. & Lefkowitz, E.) (Elsevier, New York, 2011)). Adenoviruses are the cause of an estimated 5-10% of febrile illnesses in children worldwide (Fox, J. P., Hall, C. E. & Cooney, M. K. *Am J Epidemiol* 105, 362-386 (1977)). Some serotypes, such as human adenovirus type 14 (hAd14), have been associated with severe and potentially fatal outbreaks of pneumonia in residential facilities and military bases (Lewis, P. F., et al., *J Infect Dis* 199, 1427-1434 (2009)). Adenoviruses have also been associated with other clinical syndromes including conjunctivitis, hepatitis, and diarrhea. In nonhuman primates, most epidemiologic studies of adenoviruses have focused on their identification in fecal samples from asymptomatic animals (Banyai, K., et al. *Vet Microbiol* 142, 416-419 (2010); Roy, S., et al. *PLoS Pathog* 5, e1000503 (2009); Wevers, D., et al, *Virol J* 7, 303 (2010)). Overt respiratory disease associated with simian adenoviruses has also been observed (Tong, S., et al., *Am J Trop Med Hyg* 82, 967-970 (2010)). Although adenoviruses are significant pathogens, genetically modified strains are being actively explored as potential vectors for vaccines and gene therapy (Ghosh, S. S., Gopinath, P. & Ramesh, A. *Appl Biochem Biotechnol* 133, 9-29 (2006)).

It is unclear whether or not infection by adenoviruses is species-specific. Human adenoviruses do not usually replicate in monkey cells (or vice versa). Studies of sera from animal handlers and zoo workers exposed to chimpanzees in captivity fail to detect antibodies to chimpanzee adenoviruses (Basnight, M., Jr., Rogers, N. G., Gibbs, C. J., Jr. & Gajdusek, D. C., *Am J Epidemiol* 94, 166-171 (1971); Xiang, Z., et al., *Emerg Infect Dis* 12, 1596-1599 (2006)). However, recent serological surveys have found antibodies to New World or Old World monkey adenoviruses in donor human sera from regions where the monkeys are endemic (Xiang, Z., et al., supra; Ersching, J., et al., *Virology* 407, 1-6 (2010); Roy et al., supra). In addition, phylogenetic analyses of adenoviruses from greater apes reveal that they fall precisely into "human" adenoviral groups B, C, and E. The high degree of sequence relatedness within members of each group suggests that at least some adenoviral strains may be capable of infecting both nonhuman primates and humans.

BRIEF SUMMARY OF THE INVENTION

The claimed subject matter relates to the Applicants' discovery of a Titi Monkey Adenovirus (TMAdV) during a fulminant pneumonia outbreak at a primate research center. A human researcher in close contact with the monkey colony tested positive, demonstrating the potential for cross-species outbreak.

Accordingly, the claimed subject matter provides compositions and methods useful in the detection, treatment and prevention, and modulation of TMAdV infection.

In an embodiment, an isolated nucleic acid is provided. The isolated nucleic acid comprises a nucleotide sequence at least 100 nucleotides in length that has at least 90% sequence identity over its length to SEQ ID NO:1 or its complement. In an embodiment, the nucleic acid comprises at least 95% identity over its length to SEQ ID NO:1. In an embodiment, the nucleic acid comprises at least 90% identity over the full length of SEQ ID NO:1. In an embodiment, the nucleic acid comprises at least 95% identity over the full length SEQ ID NO:1. In yet another embodiment, the nucleotide sequence comprises SEQ ID NO:1.

In an embodiment, an isolated Titi Monkey Adenovirus (TMAdV) is provided. The TMAdV comprises a nucleotide sequence that has at least 90% sequence identity over the full length of SEQ ID NO:1. In an embodiment, the TMAdV comprises at least 95% identity over the full length of SEQ ID NO:1. In an embodiment, the TMAdV comprises SEQ ID NO:1.

In an embodiment, an isolated nucleic acid is provided. The isolated nucleic acid comprises a nucleotide sequence at least 100 nucleotides in length and has at least 90% sequence identity to an open reading frame selected from the group consisting of SEQ ID NOs:2-37. In an embodiment, the isolated nucleotide sequence comprises at least 95% identity to the open reading frame encoded by the nucleotide sequence selected from the group consisting of SEQ ID NOs:2-37. In an embodiment, the nucleotide sequence comprises the open reading frame encoded by the nucleotide sequence selected from the group consisting of SEQ ID NOs:2-37.

In an embodiment, an expression vector is provided. In one aspect, expression vector comprises an isolated nucleic acid comprising a nucleotide sequence at least 100 nucleotides in length that has at least 90% sequence identity over its length to SEQ ID NO:1 or its complement. In another aspect, the expression vector comprises an isolated nucleic acid comprising a nucleotide sequence at least 100 nucleotides in length and has at least 90% sequence identity to an open reading frame selected from the group consisting of SEQ ID NOs:2-37. In another embodiment, a host cell is provided comprising the expression vectors.

In another embodiment, a composition (i.e., pharmaceutical or physiological) is provided. In one aspect, the composition comprises an isolated nucleic acid comprising a nucleotide sequence at least 100 nucleotides in length that has at least 90% sequence identity over its length to SEQ ID NO:1 or its complement. In another aspect, the composition comprises an isolated nucleic acid comprising a nucleotide sequence at least 100 nucleotides in length and has at least 90% sequence identity to an open reading frame selected from the group consisting of SEQ ID NOs:2-37.

In an embodiment, a protein is provided. The protein is encoded by an isolated nucleic acid comprising a nucleotide sequence at least 100 nucleotides in length and has at least 90% sequence identity to an open reading frame selected from the group consisting of SEQ ID NOs:2-37.

In an embodiment, a composition (i.e., pharmaceutical or physiological) is provided. The composition comprises a protein encoded by an isolated nucleic acid comprising a nucleotide sequence at least 100 nucleotides in length and has at least 90% sequence identity to an open reading frame selected from the group consisting of SEQ ID NOs:2-37.

In an embodiment, an isolated antibody is provided. The antibody specifically binds to a protein encoded by an isolated nucleic acid comprising a nucleotide sequence at least 100 nucleotides in length and has at least 90% sequence identity to an open reading frame selected from the group consisting of SEQ ID NOs:2-37. In one aspect, the antibody is a monoclonal antibody. In another aspect, the antibody is a polyclonal antibody. In yet another aspect, purified serum comprising the polyclonal antibodies is provided. In another aspect, a method of producing a TMAdV antibody is provided.

In an embodiment, a method is provided. The method comprises detecting a TMAdV nucleic acid comprising the steps of contacting a sample suspected of comprising a TMAdV nucleic acid with a nucleotide sequence at least 100 nucleotides in length that has 90% identity over its length to the corresponding segment of SEQ ID NO:1, and detecting the presence or absence of specific binding of the nucleotide sequence to a TMAdV nucleic acid.

In another embodiment a method is provided comprising detecting a TMAdV nucleic acid, the method comprising the steps of contacting a sample suspected of comprising the TMAdV nucleic acid with at least one primer that hybridizes to a nucleotide sequence of SEQ ID NO:1, performing a PCR reaction; and detecting the presence or absence of the TMAdV nucleic acid.

In another embodiment a method is provided comprising detecting a TMAdV infection in a sample. The method comprises the steps of contacting a sample suspected of comprising a TMAdV antibody with a TMAdV protein, and detecting the presence or absence of the TMAdV antibody. In another embodiment, a detectable moiety detects the presence or absence of the TMAdV antibody.

In another embodiment a method is provided comprising detecting a TMAdV infection in a sample. The method comprises the steps of contacting a sample suspected of comprising a TMAdV protein with a TMAdV antibody, and detecting the presence or absence of the TMAdV protein. In another embodiment, a detectable moiety detects the presence or absence of the TMAdV protein.

In an embodiment a method is provided comprising assaying for an anti-TMAdV compound, the method comprising the steps of contacting a sample comprising a TMAdV, the TMAdV comprising a genome that has at least 90% identity over its length to the corresponding segment of SEQ ID NO:1; and determining whether the compound has a functional effect on TMAdV.

In an embodiment, a method is provided. The method comprises treating or preventing a TMAdV infection in a subject comprising the step of administering to the subject a therapeutically effective dose of a compound that has a functional effect on TMAdV. In one aspect, the compound comprises an antigen capable of providing an immune response. In another aspect, the antigen is a protein encoded by an isolated nucleic acid comprising a nucleotide sequence at least 100 nucleotides in length and has at least 90% sequence identity to an open reading frame selected from the group consisting of SEQ ID NOs:2-37. In another aspect, the compound comprises an antibody that specifically binds to a protein encoded by an isolated nucleic acid comprising a nucleotide sequence at least 100 nucleotides in length and has at least 90% sequence identity to an open reading frame selected from the group consisting of SEQ ID NOs:2-37. In another aspect, the compound comprises a small organic molecule. In another aspect, the compound comprises an aptamer. In one aspect, the aptamer is an siRNA or antisense molecule comprising a double-stranded region of about 15 to about 60 nucleotides in length and has at least 90% identity over its length to the corresponding segment of SEQ ID NO:1. In another aspect, the compound is administered by means comprising oral, topical, intraarticular, intravenous, intramuscular, intradermal, intraperitoneal or subcutaneous routes.

In an embodiment, a vaccine is provided. In an aspect, the vaccine comprises an isolated protein encoded by an isolated nucleic acid comprising a nucleotide sequence at least 100 nucleotides in length and has at least 90% sequence identity to an open reading frame selected from the group consisting of SEQ ID NOs:2-37. In another aspect, the vaccine comprises an antibody that specifically binds to a protein encoded by an isolated nucleic acid comprising a nucleotide sequence at least 100 nucleotides in length and has at least 90% sequence identity to an open reading frame selected from the group consisting of SEQ ID NOs:2-37.

In an embodiment, a kit is provided. In one aspect, the kit detects a TMAdV nucleic acid, the kit comprising a nucleotide sequence at least 100 nucleotides in length that has at least 90% identity over its length to the corresponding segment of SEQ ID NO:1. In another aspect, the kits detects a TMAdV nucleic acid, the kit comprising at least one primer that hybridizes to a nucleotide sequence comprising SEQ ID NO:1 under highly stringent PCR conditions comprising a denaturation phase of 90° C.-95° C. for 30 sec-2 min., an annealing phase of 50° C. to about 65° C. lasting 30 sec.-2 min., and an extension phase of about 72° C. for 1-2 min., and an extension phase of about 72° C. for 1-2 min for 20-40 cycles. In another aspect, the kit detects TMAdV in a sample and comprises an antibody that specifically binds to a protein encoded by an isolated nucleic acid comprising a nucleotide sequence at least 100 nucleotides in length and has at least 90% sequence identity to an open reading frame selected from the group consisting of SEQ ID NOs:2-37. In one aspect, the antibody is a monoclonal antibody. In another aspect, the antibody is a polyclonal antibody. In another aspect, the kit comprises a protein encoded by the nucleotide sequences selected from the group consisting of SEQ ID NOs:2-37.

In an embodiment, a method of expressing a protein is provided. The method comprises a host cell further comprising an expression vector comprising the nucleotide sequences selected from the group consisting of SEQ ID NOs:2-37. In some embodiments the host cell is a human cell.

BRIEF DESCRIPTION OF THE DRAWINGS

FIG. 9 is the TMAdV sequence. The entire TMAdV sequence is provided with identification of putative open reading frames.

DETAILED DESCRIPTION OF THE INVENTION

Figure 6:
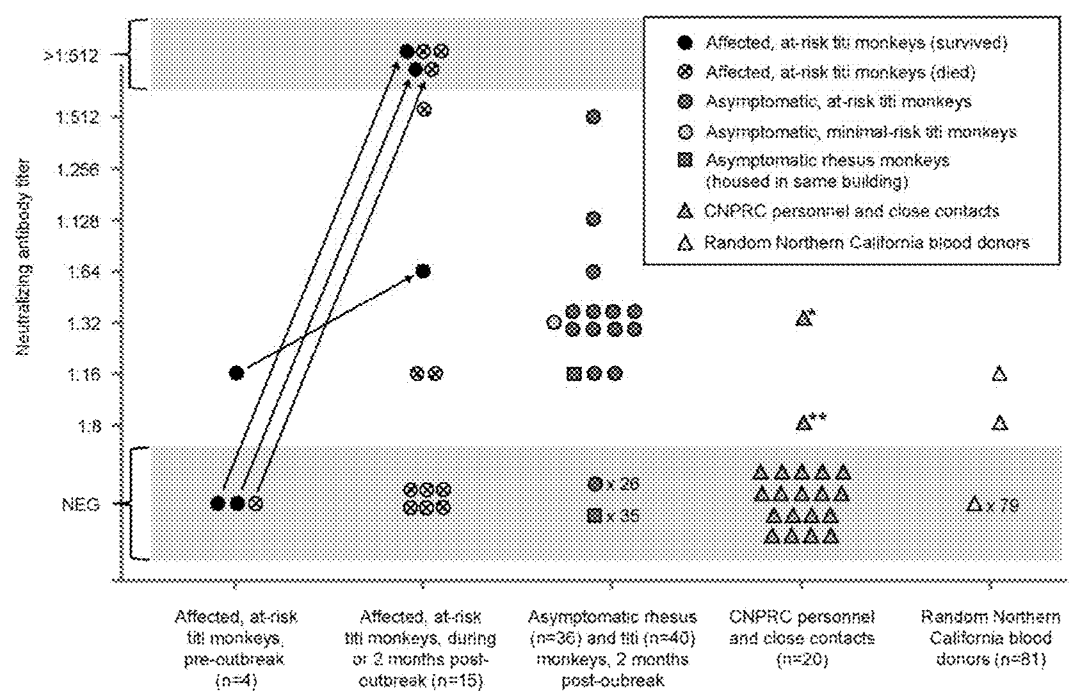
FIG. 6 shows the seroprevalence of TMAdV in humans and monkeys. Sera from titi monkeys (circles), rhesus macaques (squares), and humans (triangles) were tested for antibodies to TMAdV by virus neutralization. Arrows designate pre-outbreak and post-outbreak serum samples from the same individual monkey. Pre-outbreak serum samples were previously banked in 2007. Sera from CNPRC personnel and close contacts (orange triangles) were collected 4 months post-outbreak, except for the two family members of the clinically ill researcher, whose sera were collected 1 year post-outbreak. * denotes a clinically ill researcher; ** denotes a family member of the researcher, who was also sick. Abbreviations: CNPRC, California National Primate Research Center; NEG, negative.

Described herein is the identification of a novel adenovirus associated with a fulminant pneumonia outbreak in a titi monkey colony. Although the absence of an animal model precludes a strict fulfillment of Koch's postulates, there are several lines of evidence implicating this novel adenovirus, TMAdV, as the cause of the outbreak. First, conventional testing for other pathogens was negative, and affected monkeys did not respond to empiric therapy with antibiotics or antivirals. Second, the clinical presentation of pneumonia and hepatitis is consistent with the known spectrum of disease associated with adenoviral infections. Third, TMAdV sequence was recovered by PCR in various body fluids and tissues from affected monkeys, including blood, respiratory secretions, and lung/liver tissue (Table 1). Fourth, the finding of intranuclear inclusions in diseased tissues, as well as direct visualization of adenoviral-like particles (TMAdV) in lung alveoli by electron microscopy (FIGS. 1D-2 to 1D-4) support a role for TMAdV in the pathogenesis of tissue injury in affected monkeys. Finally, the most compelling data for TMAdV as the etiology of this outbreak is the marked neutralizing Ab response to the virus in 2 surviving animals, undetectable prior to the outbreak but >1:512 at convalescence (FIG. 6).

Figure 3:
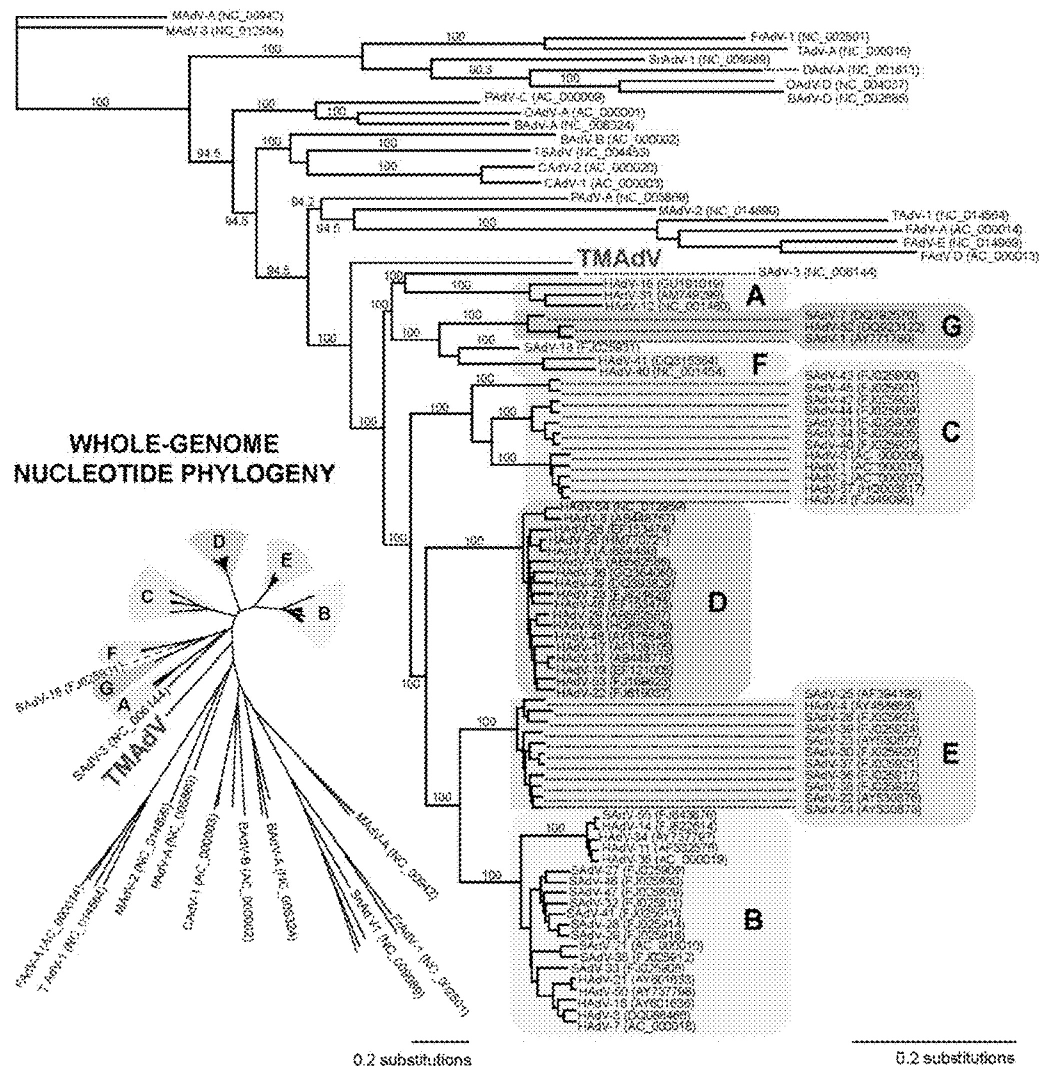
FIG. 3 illustrates the whole-genome phylogenetic analysis of TMAdV. The whole-genome nucleotide phylogenetic tree is reconstructed from a multiple sequence alignment of all 95 unique, fully-sequenced adenovirus genomes in GenBank and TMAdV. Both rectangular cladogram and radial tree layouts are displayed. The branch corresponding to TMAdV is highlighted in boldface red. Abbreviations: HAdV, human adenovirus; SAdV, simian adenovirus; MAdV, mouse adenovirus, FrAdV, frog adenovirus; TAdV, turkey adenovirus; SnAdV, snake adenovirus; DAdV, duck adenovirus; OAdV, ovine adenovirus; BAdV, bovine adenovirus; PAdV, porcine adenovirus; TSAdV, tree shrew adenovirus; CAdV, canine adenovirus.

Although TMAdV retains the core genomic features common to all adenoviruses (FIG. 2C), phylogenetic analysis clearly places TMAdV within a separate group, with no closely related neighbors (FIG. 3). A phylogenetic distance of >10% combined with the lack of cross-neutralization defines TMAdV as a new species. Emerging human adenovirus strains such as hAd14 and hAdV-D53 are known to arise from recombination events among related ancestral strains (Kaj on, A. E., et al., *J Infect Dis* 202, 93-103 (2010); Walsh, M. P., et al., *PLoS ONE* 4, e5635 (2009)). However, bootscanning analysis to look for such events in TMAdV was uninformative because closely related and/or ancestral strains to TMAdV have not yet been identified. Although the presence of an RGD motif in the TMAdV penton base suggests that the virus uses $\alpha_v$ integrins for internalization (Wickham, T. J. et al., *Cell* 73, 309-319 (1993)), the high sequence divergence in the fiber protein (Table 2) implies that the fiber knob of TMAdV does not use human CAR (coxsackievirus-adenovirus receptor) as its primary receptor for attachment (Bergelson, J. M., et al., *Science* 275, 1320-1323 (1997)). This is significant because the attachment of the fiber knob to its receptor determines adenoviral cell tropism (Renaut, L. et al., *Virology* 321, 189-204 (2004)), and choice of receptor may define both the extent and virulence of disease caused by TMAdV. The TMAdV genome is approximately 35 kB with 35 open reading frames.

The virus grew efficiently in human A549 lung adenocarcinoma cells, and a fully adapted strain of TMAdV (after 10 passages in human A549 cells) exhibits an extended host range with the ability to infect all 3 cell lines, both monkey and human. This observation suggests that TMAdV possesses an inherent capacity to cross the species barrier and infect both humans and nonhuman primates.

The virulence of TMAdV in healthy, apparently immunocompetent titi monkeys (83% case fatality rate) is highly unusual for infections by adenovirus. In humans, deaths due to adenovirus infections or outbreaks are generally low (up to 18% for hAd14-associated pneumonia, see e.g., Lewis, P. F., et al., 14. *J Infect Dis* 199, 1427-1434 (2009)). Furthermore, severe infections from adenoviruses are closely associated with older age, immunosuppression, and chronic underlying conditions such as kidney failure (Lewis et al., supra; Carrigan, D. R., *Am J Med* 102, 71-74 (1997)). Young, healthy individuals are much less likely to succumb to adenoviral-related illness. The severity of TMAdV-related illness in affected titi monkeys indicates that this species of monkey may lack pre-existing immunity, and, thus, may not be a native host for the virus. The failure to detect asymptomatic fecal shedding of TMAdV (Table 1) also suggests that the virus does not normally circulate in titi monkeys.

Although the exact origin of TMAdV remains unclear, a cross-species "jump" from captive rhesus macaques to titi monkeys is the most likely precipitant for the outbreak. First, there have been no new introductions of monkeys into the closed colony for the past 6 years. Second, CNPRC personnel who visited macaque areas would occasionally enter titi rooms with no change in personal protective equipment (anecdotal evidence), thus providing a route of transmission for TMAdV. Third, neutralizing Abs to TMAdV were detected in rhesus macaques, but not in asymptomatic titi monkeys, within the same building (FIG. 6). Fourth, the virulence of TMAdV in titi monkeys makes them unlikely to be native hosts for the virus. Finally, the closest known phylogenetic relatives to TMAdV appear to be Old World monkey adenoviruses such as sAd3 and sAd18 (FIG. 4; Table 2). Serological evidence for cross-species adenoviral transmission events between different nonhuman primate species has also been reported in the literature (Mwenda, J. M. et al., *East Afr Med J* 82, 371-375 (2005)).

The decreased levels of neutralizing Abs to TMAdV in t two human cases relative to those in some affected titi monkeys (>1:512) may be secondary to adenovirus-specific T-cell responses in humans, which were found to be largely absent in nonhuman primates. Because 2.5% of random adult blood donors have neutralizing antibody to TMAdV, it can be implied that cross-species transmission of TMAdV may be ongoing in the human population. The newly discovered capacity of adenoviruses such as TMAdV to cross species barriers highlights the need to monitor adenoviruses closely for outbreak or even pandemic potential.

Described herein is the potential for zoonotic transmission of TMAdV. Provided are compositions and methods useful for the identification, isolation, expression, purification, detection, treatment, preventions, and modulation of TMAdV.

Definitions

Unless otherwise noted, the technical terms used herein are according to conventional usage as understood by persons skilled in the art. Definitions of common terms in molecular biology may be found in standard texts (e.g. Benjamin Lewin, Genes V, published by Oxford University Press, 1994 (ISBN 0-19854287-9); Kendrew et al. (eds.), The Encyclopedia of Molecular Biology, published by Blackwell Science Ltd, 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8)).

The term "nucleic acid" refers to deoxyribonucleotides or ribonucleotides and polymers thereof in either single- or double-stranded form, and complements thereof. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide. A particular nucleotide sequence also implicitly encompasses "splice variants," which as the name suggests, are products of alternative splicing of a gene. After transcription, an initial nucleic acid transcript can be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The term "isolated" as used herein with respect to nucleic acids, such as DNA or RNA, refers to molecules separated from other DNAs, or RNAs, respectively that are present in the natural source of the macromolecule. Isolated is meant to include nucleic acid fragments which are not naturally occurring as fragments and would not be found in the natural state. The term isolated as used herein also refers to a nucleic acid or peptide that is substantially free of cellular material, viral material, or culture medium when produced by recombinant DNA techniques, or chemical precursors, or other chemicals when chemically synthesized.

The term "identical" or "identity" or "percent identity," or "sequence identity" in the context of two or more nucleic acids or polypeptide sequences that correspond to each other refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical" and are embraced by the term "substantially identical.' This definition also refers to, or can be applied to, the compliment of a test sequence. The definition also includes sequences that have deletions and/or additions, as well as those that have substitutions. As described below, the preferred algorithms can account for gaps and the like. Preferably, identity exists for a specified entire sequence or a specified portion thereof or over a region of the sequence that is at least about 25 amino acids or nucleotides in length, or more preferably over a region that is 50-100 amino acids or nucleotides in length. A corresponding region is any region within the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters. A comparison window includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted (e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J MoL Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Titi Monkey Adenovirus" or "TMAdV" refers to both the genetic components of the virus, e.g., the genome and RNA transcripts thereof, proteins encoded by the genome (including structural and nonstructural proteins), and viral particles. The term "comprising a nucleic acid sequence" as it refers to TMAdV refers to nucleic acids and polypeptide polymorphic variants, alleles, mutants, and interspecies homologs that: (1) have a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more nucleic acids, up to the full length sequence, to the nucleotide sequence of SEQ ID NO:1; (2) bind to antibodies, e.g., polyclonal or monoclonal antibodies, raised against an immunogen comprising an amino acid sequence of a protein encoded by an open reading frame (ORF) of SEQ ID NOs:2-37; and conservatively modified variants thereof; (3) specifically hybridize under stringent hybridization conditions to an anti-sense strand corresponding to a nucleic acid sequence of SEQ ID NO:1 and conservatively modified variants thereof; (4) encoding a protein having an amino acid sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more amino acids, to a protein (e.g., a N, X, P, M, G, L protein) encoded by an open reading frame of SEQ ID NOs:2-37, and also those of FIG. 2.

"Protein encoded by TMAdV" or "protein encoded by the nucleotide sequence" comprising identity to a TMAdV open reading frame (ORF) refers to structural and non-structural Titi Monkey adenovirus proteins encoded by nucleic acids that: (1) have a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more nucleic acids, up to the full length sequence, to the nucleotide sequence of SEQ ID NO:1; (2) bind to antibodies, e.g., polyclonal or monoclonal antibodies, raised against an immunogen comprising an amino acid sequence of a protein encoded by an open reading frame of SEQ ID NOs:2-37; and conservatively modified variants thereof; (3) specifically hybridize under stringent hybridization conditions to an anti-sense strand corresponding to a nucleic acid sequence of SEQ ID NOs:2-37; and (4) encoding a protein having an amino acid sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of at least about 25, 50, 100, 200, 500, 1000 or more amino acids, to a protein encoded by an open reading frame of SEQ ID NOs:2-37. The amino acid sequence of the structural and non-structural viral proteins encoded by TMAdV can be easily identified by one of skill in the art, using the algorithms disclosed herein, by aligning the TMAdV sequence with other adenovirus sequences, including simian adenovirus 3 (SAdV-3), simian adenovirus 18 (SAdV-18), and the Group D human adenoviruses (e.g HAdV-9).

The term "open reading frame" or "ORF" refers to a length of DNA or RNA sequence capable of being translated into a peptide normally located between a start or initiation signal and a termination signal.

The term "expression vector" indicates a plasmid, a virus or another medium, known in the art, into which a nucleic acid sequence for encoding a desired protein can be inserted or introduced.

The term "host cell" is a cell that is susceptible to transformation, transfection, transduction, conjugation, and the like with a nucleic acid construct or expression vector. Host cells can be derived from plants, bacteria, yeast, fungi, insects, animals, etc.

The terms "polypeptide" or "peptide" or "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Macromolecular structures such as polypeptide structures can be described in terms of various levels of organization. For a general discussion of this organization (see, e.g., Alberts et al., *Molecular Biology of the Cell* (3rd ed., 1994) and Cantor and Schimmel, *Biophysical Chemistry Part I: The Conformation of Biological Macromolecules* (1980)). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity. Typical domains are made up of sections of lesser organization such as stretches of 3-sheet and a-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes. Amino acid substitutions, deletions or additions to individual or a small percentage of amino acids in the encoded sequence is a conservatively modified variant, where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "antibody" refers to a polypeptide comprising a framework region from an immunoglobulin gene or fragments thereof that specifically binds and recognizes an antigen. The term "antigen" refers to any molecule capable of being bound by an antibody or a T cell receptor if presented by MHC molecules. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (Vl) and variable heavy chain ($V_H$) refer to these light and heavy chains respectively. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 bp a disulfide bond. The F(ab)'2 can be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993)). While various antibody fragments are defined in terms of the digestion of an intact antibody, one of skill will appreciate that such fragments can be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies that are raised to TMAdV, polymorphic variants, alleles, orthologs, and conservatively modified variants, or splice variants, or portions thereof, can be selected to obtain only those polyclonal antibodies that are specifically immunoreactive with TMAdV and not with other proteins. This selection can be achieved by subtracting out antibodies that cross-react with other molecules. A variety of immunoassay formats can be used to select antibodies specifically immunoreactive with a particular protein, as described herein.

The term "detectable moiety" or "conjugate" refers to any atom, molecule or a portion thereof, the presence, absence or level of which is directly or indirectly monitorable. A variety of detectable moieties are well known to those skilled in the art, and can be any material detectable by spectroscopic, photochemical, biochemical, immunochemical, electrical, optical or chemical means. Such detectable labels can include, but are not limited to, magnetic beads, fluorescent dyes, radiolabels, enzymes, and colorimetric labels such as colloidal gold or colored glass or plastic beads, each of which is described in greater detail herein.

The term "vaccine" refers to a pharmaceutical composition comprising at least one immunologically active component that induces an immunological response in an animal and possibly but not necessarily one or more additional components that enhance the immunological activity of the active component. A vaccine can additionally comprise further components typical to pharmaceutical compositions. The immunologically active component of a vaccine can comprise complete virus particles in either their original form or as attenuated particles in a so called modified live vaccine (MLV) or particles inactivated by appropriate methods in a so called killed vaccine (KV). A vaccine comprising antigenic substances can be administered for the purpose of inducing a specific and active immunity against a disease provoked by a TMAdV infection. A vaccine can also provide passive immunity in the form of antibodies previously generated against TMAdV antigens.

The term "immune response" refers to a reaction of the immune system to an antigen in the body of a host, which includes generation of an antigen-specific antibody and/or cellular cytotoxic response. The term further refers to an immune system response that leads to a condition of induce sensitivity to an immunogenic product.

A "biological sample" or "sample" includes sections of tissues such as biopsy and autopsy samples, and frozen sections taken for histologic purposes. Such samples include blood and blood fractions or products (e.g., serum, plasma, platelets, red blood cells, and the like), sputum, cloacal swabs, mucosa, tissue, cultured cells, e.g., primary cultures, explants, and transformed cells, biological fluids, stool, urine, etc. A biological sample is typically obtained from a eukaryotic organism. The tissue sampled can be, for instance, skin, brain (e.g., cerebrum, cerebellum, optic lobe), spinal cord, adrenals, pectoral muscle, lung, heart, liver, crop, proventriculus, ventriculus, duodenum, small intestine, large intestine, cloaca, kidney, bursa of fabricus, spleen, pancreas, adrenal gland, bone marrow, lumbosacral spinal cord, or blood. Contacting a sample refers to the plain and ordinary meaning to refer to exposing the sample.

The term "detecting" when in reference to detecting the presence of TMAdV refers to determining the presence, using any method, of the virus or viral particles including viral peptides, inside cells, on cells, and/or in medium with which cells or the virus have come into contact. The methods are exemplified by, but not limited to, the observation of cytopathic effect, detection of viral protein, such as by immunofluorescence, ELISA, or Western blot hybridization, detection of viral nucleic acid sequence, such as by PCR, RT-PCR, Southern blots, and Northern blots, nucleic acid hybridization, nucleic acid arrays, and the like.

The phrase "TMAdV infection" refers to the invasion by, multiplication and/or presence of TMAdV in a cell or a subject with or without symptoms.

The phrase "functional effect" in the context of assays for testing compounds that modulate activity of TMAdV, or for treating or preventing TMAdV infection, includes the determination of a parameter that is indirectly or directly under the influence of TMAdV, e.g., a phenotypic or chemical effect, such as the ability to increase or decrease viral genome replication, viral RNA and protein production, virus packaging, viral particle production (particularly replication competent viral particle production), cell receptor binding, viral transduction, cellular infection, antibody binding, inducing a cellular or humoral immune response, viral protein enzymatic activity, etc. "Functional effects" include in vitro, in vivo, and ex vivo activities. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for a protein; measuring inducible markers or transcriptional activation of a protein; measuring binding activity or binding assays, e.g. binding to antibodies; measuring changes in ligand or substrate binding activity; measuring viral replication; measuring cell surface marker expression; measurement of changes in protein levels; measurement of RNA stability; identification of downstream or reporter gene expression (CAT, luciferase, 0-gal, GFP and the like), e.g., via chemiluminescence, fluorescence, colorimetric reactions, antibody binding, and inducible markers.

The term "test compound" or "compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis. Compounds can be inhibitors, activators, or modulators of TMAdV nucleic acid and polypeptide sequences, and are used to refer to activating, inhibitory, or modulating molecules identified using in vitro and in vivo assays of the TMAdV nucleic acid and polypeptide sequences. Inhibitors are compounds that, e.g., bind to, partially or totally block activity, decrease, prevent, delay activation, inactivate, desensitize, or down regulate the activity or expression of TMAdV, e.g., antagonists. Activators are compounds that increase, open, activate, facilitate, enhance activation, sensitize, agonize, or up regulate TMAdV activity, e.g., agonists. Inhibitors, activators, or modulators also include genetically modified versions of TMAdV, e.g., versions with altered activity, as well as naturally occurring and synthetic ligands, substrates, antagonists, agonists, antibodies, peptides, cyclic peptides, nucleic acids, antisense molecules, ribozymes, or small chemical molecules for example.

The phrase "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

The term "aptamer" refers to a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. Aptamer action can be specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule.

An "siRNA" molecule or an "RNAi" molecule refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length. See also PCT/US03/07237, herein incorporated by reference in its entirety.

The term "antisense" refers to an oligomeric compound or molecule that is at least partially complementary to a target nucleic acid molecule to which it hybridizes. Antisense compounds or molecules can include, but are not limited to, oligonucleotides, oligonucleosides, oligonucleotide analogs, oligonucleotide mimetics, and chimeric combination.

An siRNA or antisense molecule or RNAi molecule is "specific" for a target nucleic acid if it reduces expression of the nucleic acid by at least about 10% when the siRNA or RNAi is expressed in a cell that expresses the target nucleic acid.

The term "treating" or "treatment" includes the application or administration of a composition to a subject, or application or administration of a composition to a cell or tissue from a subject who has been infected with TMAdV, or has symptoms of TMAdV infection, with the purpose of curing, healing, alleviating, relieving, altering, remedying, ameliorating, improving, or affecting the disease or condition, the symptom of the disease or condition, or the risk of the disease or condition.

The term "preventing" or "prevention" includes stopping or hindering a disease, disorder, or symptoms associated with TMAdV infection.

The term "subject" refers to any animal, including, but not limited to, humans, Titi Monkeys, and other non-human primates, that presents one or more symptoms indicative of TMAdV infection.

The term "administering" or "administration" refers to therapeutically or prophylactically administering an effective amount of a composition or medicament during the course of therapy. Prophylactic administration can occur prior to manifestation of symptoms characteristic of a TMAdV infection.

The phrase "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The phrase "stringent conditions" refers to conditions under which a probe will hybridize to its target subsequence, typically in a complex mixture of nucleic acids, but to no other sequences. The term "hybridize" refers to the process by which single strands of nucleic acid sequences form double-helical segments through hydrogen bonding between complementary nucleotides. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The T. is the temperature (under defined ionic strength, pH, and nucleic concentration) at which 50% of the probes complementary to the target hybridize to the target sequence at equilibrium (as the target sequences are present in excess, at T, 50% of the probes are occupied at equilibrium). Stringent conditions can also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference (e.g., and *Current Protocols in Molecular Biology*, ed. Ausubel, et al.).

Isolation, Expression, Purification, and Detection of TMAdV

The subject matter described herein relies on routine techniques in the field of recombinant genetics. Recombinant when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

Basic texts disclose general methods of use in this invention (e.g. Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

TMAdV Expression

To obtain high level expression of a cloned gene or genome, one typically subclones the nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described (e.g., in Sambrook et al., and Ausubel et al, supra. Bacterial expression systems for expressing the protein are available in, e.g., *E. coli, Bacillus* sp., and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are well known in the art and are also commercially available. Retroviral expression systems can be used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function. Heterologous refers to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

In addition to the promoter, the expression vector typically contains a transcription unit or expression cassette that contains all the additional elements required for the expression of the nucleic acid in host cells. A typical expression cassette thus contains a promoter operably linked to the nucleic acid sequence encoding the nucleic acid of choice and signals required for efficient polyadenylation of the transcript, ribosome binding sites, and translation termination. Additional elements of the cassette can include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region can be obtained from the same gene as the promoter sequence or can be obtained from different genes.

The particular expression vector used to transport the genetic information into the cell is not particularly critical. Any of the conventional vectors used for expression in eukaryotic or prokaryotic cells can be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags can be included in an expression cassette for nucleic acid rescue. Markers such as fluorescent proteins, green or red fluorescent protein, 13-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMT010/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can also be regulated using inducible promoters. With inducible promoters, expression levels are tied to the concentration of inducing agents, such as tetracycline, by the incorporation of response elements for these agents into the promoter. Generally, high level expression is obtained from inducible promoters only in the presence of the inducing agent; basal expression levels are minimal.

Vectors can have a regulatable promoter, e.g., tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a sequence of choice under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, as any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J Bact.* 132:349-351 (1977); Clark-Curtiss & Curtiss, *Methods in Enzymology* 101:347-362 (Wu et al., eds, 1983)).

Any of the well-known procedures for introducing foreign nucleotide sequences into host cells can be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing TMAdV proteins and nucleic acids.

After the expression vector is introduced into the cells, the transfected cells are cultured under conditions favoring expression of the protein of choice, which is recovered from the culture using standard techniques identified below.

Either naturally occurring or recombinant TMAdV proteins can be purified for use in diagnostic assays, for making antibodies (for diagnosis and therapy) and vaccines, and for assaying for anti-viral compounds. Naturally occurring protein can be purified, e.g., from primate tissue samples. Recombinant protein can be purified from any suitable expression system.

TMAdV Proteins

The protein can be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant protein is being purified. For example, proteins having established molecular adhesion properties can be reversible fused to the protein. With the appropriate ligand or substrate, a specific protein can be selectively adsorbed to a purification column and then freed from the column in a relatively pure form. The fused protein is then removed by enzymatic activity. Finally, protein could be purified using immunoaffinity columns. Recombinant protein can be purified from any suitable source, include yeast, insect, bacterial, and mammalian cells.

Recombinant proteins can be expressed and purified by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria can form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM MgCl2, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies can be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation can occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, it is possible to purify recombinant protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM MgSO4 and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Solubility fractionation can be used as a standard protein separation technique for purifying proteins. As an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The protein can also be separated from other proteins on the basis of its size, net surface charge, hydrophobicity, and affinity for ligands or substrates using column chromatography. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Detecting the Presence or Absence of TMAdV

Described herein are diagnostic assays to detect TMAdV, TMAdV nucleic acids (genome and genes), TMAdV antibodies in an infected subject, and TMAdV proteins.

Detecting TMAdV Nucleic Acids

TMAdV infection can be detected based on the level of a TMAdV RNA or DNA in a biological sample. Primers from TMAdV can be used for detection of TMAdV, diagnosis, and determination of TMAdV viral load. Any suitable primer can be used to detect the genome, nucleic acid sub sequence, ORF, or protein of choice, using, e.g., methods described in US 20030104009. For example, the subject nucleic acid compositions can be used as single- or double-stranded probes or primers for the detection of TMAdV mRNA or cDNA generated from such mRNA, as obtained can be present in a biological sample (e.g., extracts of human cells). The TMAdV polynucleotides of the invention can also be used to generate additional copies of the polynucleotides, to generate antisense oligonucleotides, and as triple-strand forming oligonucleotides. For example, two oligonucleotide primers can be employed in a polymerase chain reaction (PCR) based assay to amplify a portion of TMAdV cDNA derived from a biological sample, wherein at least one of the oligonucleotide primers is specific for (i.e., hybridizes to) the TMAdV polynucleotide. The primers are preferably at least or about 12, 15, 16, 18, 20, 22, 24, 25, 30, 35, 40, 45, or 50 nt or are, for instance, from about 12 to 50 nt in length, 15 to 30 nt in length, 15 to 25 nt in length, or 20 to 30 nt in length) fragments of a contiguous sequence of SEQ ID NO: 1 or other polynucleotide sequence encoding an TMAdV nucleic acid or polypeptide. The amplified cDNA is then separated and detected using techniques well known in the art, such as gel electrophoresis. Similarly, oligonucleotide probes that specifically hybridize to a TMAdV polynucleotide can be used in a hybridization assay to detect the presence of the TMAdV polynucleotide in a biological sample.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided (e.g., in Innis et al. (1990) *PCR Protocols, A Guide to Methods and Applications*, Academic Press, Inc. N.Y.)).

Nucleic acid probes or primers specific to TMAdV can be generated using the polynucleotide sequences disclosed herein. The probes are preferably at least about 12, 15, 16, 18, 20, 22, 24, or 25 nt fragments of a contiguous sequence of SEQ ID NO: 1 or other polynucleotide sequence encoding a TMAdV nucleic acid or polypeptide. Nucleic acid probes can be less than about 200 bp, 150 bp, 100 bp, 75 bp, 50 bp, 60 bp, 40 bp, 30 bp, 25 bp 2 kb, 1.5 kb, 1 kb, 0.5 kb, 0.25 kb, 0.1 kb, or 0.05 kb in length. The probes can be produced by, for example, chemical synthesis, PCR amplification, generation from longer polynucleotides using restriction enzymes, or other methods well known in the art. Preferred primers and probes are identical to a TMAdV nucleic acid sequence and different from a non-TMAdV sequence.

The polynucleotides described herein, particularly where used as a probe in a diagnostic assay, can be detectably labeled. Exemplary detectable labels include, but are not limited to, radiolabels, fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',T,4,7-hexachlorofluorescein (HEX), 5-carboxyfluorescein (5-FAM) or N,N,N',N'-tetramethyl-6-carboxyrho-damine (TAMRA)), radioactive labels, (e.g. .sup.32p, .sup.35S, and sup.3H), and the like. The detectable label can involve two stage systems (e.g., biotin-avidin, hapten-anti-hapten antibody, and the like).

Non-PCR-based, sequence specific DNA amplification techniques can also be used with the invention to detect TMAdV sequences. An example of such techniques include, but is not necessarily limited to, the Invader assay (see, e.g., Kwiatkowski et al. *Mol Diagn*. December 1999, 4:353-64. See also U.S. Pat. No. 5,846,717).

The claimed subject matter can also include solid substrates, such as arrays, comprising any of the polynucleotides described herein. The polynucleotides are immobilized on the arrays using methods known in the art. An array can have one or more different polynucleotides.

Any suitable qualitative or quantitative methods known in the art for detecting specific TMAdV nucleic acid (e.g., RNA or DNA) can be used. TMAdV nucleic acid can be detected by, for example, in situ hybridization in tissue sections, using methods that detect single base pair differences between hybridizing nucleic acid (e.g., using the Invader® technology described in, for example, U.S. Pat. No. 5,846,717), by reverse transcriptase-PCR, or in Northern blots containing poly A+mRNA, and other methods well known in the art. For detection of TMAdV polynucleotides in blood or blood-derived samples, the use of methods that allow for detection of single base pair mismatches is preferred.

Using the TMAdV nucleic acid as a basis, nucleic acid probes (e.g., including oligomers of at least about 8 nucleotides or more) can be prepared, either by excision from recombinant polynucleotides or synthetically, which probes hybridize with the TMAdV nucleic acid, and thus are useful in detection of TMAdV virus in a sample, and identification of infected individuals, as well as further characterization of the viral genome(s). The probes for TMAdV polynucleotides (natural or derived) are of a length or have a sequence which allows the detection of unique viral sequences by hybridization. While about 6-8 nucleotides may be useful, longer sequences may be preferred, e.g., sequences of about 10-12 nucleotides, or about 20 nucleotides or more. Preferably, these sequences will derive from regions which lack heterogeneity among TMAdV viral isolates.

Nucleic acid probes can be prepared using routine methods, including automated oligonucleotide synthetic methods. A complement to any unique portion of the TMAdV genome will be satisfactory, e.g., a portion of the TMAdV genome that allows for distinguishing TMAdV from other viruses that may be present in the sample, e.g., other TMAdV such as B19. For use as probes, complete complementarity is desirable, though it can be unnecessary as the length of the fragment is increased.

For use of such probes as diagnostics, the biological sample to be analyzed, such as blood or serum, can be treated, if desired, to extract the nucleic acids contained therein. The resulting nucleic acid from the sample can be subjected to gel electrophoresis or other size separation techniques; alternatively, the nucleic acid sample can be dot blotted without size separation. The probes are usually labeled with a detectable label. Suitable labels, and methods for labeling probes are known in the art, can include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies.

The probes can be made completely complementary to the TMAdV genome or portion thereof (e.g., to all or a portion of a sequence encoding a TMAdV GAG polypeptide). Therefore, usually high stringency conditions are desirable in order to prevent or at least minimize false positives. However, conditions of high stringency should only be used if the probes are complementary to regions of the viral genome which lack heterogeneity among TMAdV viral isolates. The stringency of hybridization is determined by a number of factors during hybridization and during the washing procedure, including temperature, ionic strength, length of time, and concentration of formamide (Sambrook et al. (1989), "Molecular Cloning; A Laboratory Manual," Second Edition (Cold Spring Harbor Press, Cold Spring Harbor, N.Y.)).

Generally, it is expected that the TMAdV sequences will be present in a biological sample (e.g., blood, cells, and the liked) obtained from an infected individual at relatively low levels, e.g., at approximately $10^2$-$10^4$ TMAdV sequences per $10^6$ cells. This level can require that amplification techniques be used in hybridization assays. Such techniques are known in the art.

For example, the Enzo Biochemical Corporation "Bio-Bridge" system uses terminal deoxynucleotide transferase to add unmodified 3'-poly-dT-tails to a DNA probe. The poly dT-tailed probe is hybridized to the target nucleotide sequence, and then to a biotin-modified poly-A. PCT Publication No. WO84/03520 and European application no. EPA124221 describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. EPA 204510 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands.

A particularly desirable technique can first involve amplification of the target TMAdV sequences in sera approximately 10,000 fold, e.g., to approximately 10 sequences/mL. This can be accomplished, for example, by the polymerase chain reactions (PCR) technique (Saiki et al. (1986), by Mullis, U.S. Pat. No. 4,683,195, and by Mullis et al. U.S. Pat. No. 4,683,202). Other amplification methods are well known in the art.

The probes, or alternatively nucleic acid from the samples, can be provided in solution for such assays, or can be affixed to a support (e.g., solid or semi-solid support). Examples of supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride, diazotized paper, nylon membranes, activated beads, and Protein A beads.

Probes (or sample nucleic acid) can be provided on an array for detection. Arrays can be created by, for example, spotting polynucleotide probes onto a substrate (e.g., glass, nitrocellulose, and the like) in a two-dimensional matrix or array. The probes can be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, can be detected once the unbound portion of the sample is washed away. Techniques for constructing arrays and methods of using these arrays are described in EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734. Arrays are particularly useful where, for example a single sample is to be analyzed for the presence of two or more nucleic acid target regions, as the probes for each of the target regions, as well as controls (both positive and negative) can be provided on a single array. Arrays thus facilitate rapid and convenience analysis.

TMAdV Antibodies

Antibodies raised against TMAdV can serve a wide variety of purposes, as described herein, which include, but are not limited to, diagnostic assays for the detection of TMAdV. A number of immunogens comprising portions of a TMAdV protein, virus or nucleic acid can be used to produce antibodies specifically reactive with the TMAdV. For example, a recombinant TMAdV protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein can also be used either in pure or impure form. The product is then injected into an animal capable of producing antibodies. Either monoclonal or polyclonal antibodies can be generated, for subsequent use in immunoassays to measure the protein.

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)).

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies can be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells can be enhanced by various techniques, including injection into the peritoneal cavity of a vertebrate host. Alternatively, one can isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-TMAdV proteins and nucleic acids, using a competitive binding immunoassay. Specific polyclonal antisera and monoclonal antibodies will usually bind with a Kd of at least about 0.1 mM, more usually at least about 1 uM, preferably at least about 0.1 uM or better, and most preferably, 0.01 uM or better. Antibodies specific only for a particular TMAdV protein can also be made by subtracting out other cross-reacting proteins. In this manner, antibodies that bind only to the protein of choice can be obtained.

Phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Chimeric antibodies can be used, which is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Humanized or primatized antibodies can be used. Generally, a humanized antibody has one or more amino acid residues introduced into it from a source which is non-human. These non-human amino acid residues are often referred to as import residues, which are typically taken from an import variable domain. Methods for humanizing or primatizing non-human antibodies are well known in the art. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S.

Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Once the specific antibodies against a TMAdV protein, virus or nucleic acid in are available, the antigen can be detected and/or quantified using any of a number of well recognized immunological binding assays (see, e.g., U.S. Pat. Nos. 4,366,241; 4,376,110; 4,517,288; and 4,837,168). TMAdV viral particles can be detected based on an epitope defined by the viral proteins as presented in a viral particle and/or an epitope defined by a viral protein that is separate from a viral particle. As used in this context, then, "antigen" is meant to refer to a TMAdV polypeptide as well as TMAdV viral particles. For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice. The antibody can be produced by any of a number of means well known to those of skill in the art and as described above. Immunoassays for detecting TMAdV protein, virus and nucleic acid in samples can be either competitive or noncompetitive, and can be either quantitative or non-quantitative.

Immunoassays

Noncompetitive immunoassays are assays in which antigen is directly detected and, in some instances the amount of antigen directly measured. Enzyme mediated immunoassays such as immunofluorescence assays (IFA), enzyme linked immunosorbent assays (ELISA), immunoblotting (western), and capture assays can be readily adapted to accomplish the noncompetitive detection of the TMAdV proteins.

An ELISA method effective for the detection of the virus can, for example, be as follows: (1) bind an antibody or antigen to a substrate; (2) contact the bound receptor with a fluid or tissue sample containing the virus, a viral antigen, or antibodies to the virus; (3) contact the above with an antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect presence of an anti-TMAdV antibody in the sample or a specific TMAdV protein as well as the virus.

Western blot (immunoblot) analysis can be used to detect and quantify the presence of TMAdV antigen in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the TMAdV antigen. The anti-TMAdV antigen antibodies specifically bind to the TMAdV antigen on the solid support. These antibodies can be directly labeled or alternatively can be subsequently detected using labeled antibodies (e.g., labeled sheep anti-mouse antibodies) that specifically bind to the anti-TMAdV antigen antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. ClM Prod. Rev.* 5:34-41 (1986)).

A TMAdV antigen and/or a patient's antibodies to the virus can be detected utilizing a capture assay. Briefly, to detect antibodies to TMAdV in a patient sample, antibodies to the patient's immunoglobulin, e.g., anti-IgG (or IgM) are bound to a solid phase substrate and used to capture the patient's immunoglobulin from serum. TMAdV, or reactive fragments of TMAdV, are then contacted with the solid phase followed by addition of a labeled antibody. The amount of patient TMAdV specific antibody can then be quantitated by the amount of labeled antibody binding.

In competitive assays, TMAdV antigen present in a sample can be detected indirectly by detecting a decrease in a detectable signal associated with a known, added (exogenous) TMAdV antigen displaced (competed away) from an anti-TMAdV antigen antibody by the unknown TMAdV antigen present in a sample.

Competitive assays can also be adapted to provide for an indirect measurement of the amount of TMAdV antigen present in the sample. Briefly, serum or other body fluids from the subject is reacted with an antibody bound to a substrate (e.g. an ELISA 96-well plate). Excess serum is thoroughly washed away. A labeled (enzyme-linked, fluorescent, radioactive, etc.) monoclonal antibody is then reacted with the previously reacted TMAdV virus-antibody complex. The amount of inhibition of monoclonal antibody binding is measured relative to a control. MABs can also be used for detection directly in samples by IFA for MABs specifically reactive for the antibody-virus complex.

A hapten inhibition assay is another competitive assay. In this assay the known TMAdV antigen can be immobilized on a solid substrate. A known amount of anti-TMAdV antibody is added to the sample, and the sample is then contacted with the immobilized TMAdV antigen. The amount of anti-TMAdV antibody bound to the known immobilized TMAdV antigen is inversely proportional to the amount of TMAdV antigen present in the sample. The amount of immobilized antibody can be detected by detecting either the immobilized fraction of antibody or the fraction of the antibody that remains in solution. Detection can be direct where the antibody is labeled or indirect by the subsequent addition of a labeled moiety that specifically binds to the antibody as described above.

Immunoassays in the competitive binding format can also be used for crossreactivity determinations. For example, a TMAdV antigen can be immobilized to a solid support. Proteins can be added to the assay that compete for binding of the antisera to the immobilized antigen. The ability of the added proteins to compete for binding of the antisera to the immobilized protein is compared to the ability of the TMAdV antigen to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera can then be used in a competitive binding immunoassay as described above to compare a second protein, thought to be perhaps an allele or polymorphic variant of a TMAdV antigen, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the TMAdV antigen that is required to inhibit 50% of binding, then the second protein is said to specifically bind to the polyclonal antibodies generated to TMAdV antigen.

Immunoassays (both competitive and non-competitive) also often use a labeling agent to specifically bind to and label the complex formed by the antibody and antigen. The labeling agent can itself be one of the moieties comprising the antibody/antigen complex. Thus, the labeling agent can be a labeled TMAdV protein nucleic acid or a labeled anti-TMAdV antibody. Alternatively, the labeling agent can be a third moiety, such a secondary antibody that specifically binds to the antibody/antigen complex (a secondary antibody is typically specific to antibodies of the species from which the first antibody is derived). Other proteins capable of specifically binding immunoglobulin constant regions, such as protein A or protein G can also be used as a label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135: 2589-2542 (1985)). The labeling agent can be modified with a detectable moiety, such as biotin, to which another molecule can specifically bind, such as streptavidin. A variety of detectable moieties are well known to those skilled in the art, and can be any material detectable by spectroscopic, photochemical, biochemical, immunochemical, electrical, optical or chemical means. Such detectable labels have been well-developed in the field of immunoassays and can include, but are not limited to, magnetic beads (e.g., DYNABEADS™), fluorescent dyes (e.g., fluorescein isothiocyanate, Texas red, rhodamine, and the like), radiolabels (e.g., 3H, 125j 35s, 14, e, or —$^{12}$ P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label can be coupled directly or indirectly to the desired component of the assay according to methods well known in the art. As indicated above, a wide variety of labels can be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize TMAdV antigen, or secondary antibodies that recognize anti-TMAdV antigen.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by the use of electronic detectors such as charge coupled devices (CCDs) or photomultipliers and the like. Similarly, enzymatic labels can be detected by providing the appropriate substrates for the enzyme and detecting the resulting reaction product. Colorimetric or chemiluminescent labels can be detected simply by observing the color associated with the label. Thus, in various dipstick assays, conjugated gold often appears pink, while various conjugated beads appear the color of the bead.

Some assay formats do not require the use of labeled components. For instance, a micro-agglutination test can also be used to detect the presence of TMAdV in test samples. Briefly, latex beads are coated with an antibody and mixed with a test sample, such that TMAdV in the tissue or body fluids that is specifically reactive with the antibody crosslink with the receptor, causing agglutination. The agglutinated antibody-virus complexes within a precipitate, visible with the naked eye or by spectrophotometer. Other assays include serologic assays, in which the relative concentrations of IgG and IgM are measured.

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

In the diagnostic methods described above, the sample can be taken directly from a subject or in a partially purified form. The antibody specific for a particular TMAdV (the primary reaction) reacts by binding to the virus. Thereafter, a secondary reaction with an antibody bound to, or labeled with, a detectable moiety can be added to enhance the detection of the primary reaction. Generally, in the secondary reaction, an antibody or other ligand which is reactive, either specifically or nonspecifically with a different binding site (epitope) of the virus will be selected for its ability to react with multiple sites on the complex of antibody and virus. Thus, for example, several molecules of the antibody in the secondary reaction can react with each complex formed by the primary reaction, making the primary reaction more detectable.

Assays for Modulators of TMAdV

Modulation of a TMAdV can be assessed using a variety of in vitro and in vivo assays, including cell-based models. Such assays can be used to test for inhibitors and activators of TMAdV. Modulators of TMAdV are tested using either recombinant or naturally occurring protein of choice. Modulation can include, but is not limited to, modulation of infection, replication, receptor binding, cell entry, particle formation, and the like.

Measurement of modulation of a TMAdV or a cell expressing TMAdV, either recombinant or naturally occurring, can be performed using a variety of assays, in vitro, in vivo, and ex vivo, as described herein. A suitable physical, chemical or phenotypic change that affects activity, e.g., enzymatic activity, cell surface marker expression, viral replication and proliferation can be used to assess the influence of a test compound on the polypeptide of this invention. When the functional effects are determined using intact cells or animals, one can also measure a variety of effects.

Assays to identify compounds with TMAdV modulating activity can be performed in vitro. Such assays can use full length TMAdV or a variant thereof, or a mutant thereof, or a fragment thereof. Purified recombinant or naturally occurring protein can be used in the in vitro methods of the invention. In addition to purified TMAdV, the recombinant or naturally occurring protein can be part of a cellular lysate or a cell membrane. As described below, the binding assay can be either solid state or soluble. Preferably, the protein or membrane is bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

A high throughput binding assay can be performed in which the protein or a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, antibodies, etc. A wide variety of assays can be used to identify TMAdV-modulator binding, including labeled protein-protein binding assays, electrophoretic mobility shifts, immunoassays, enzymatic assays, and the like. In some cases, the binding of the candidate modulator is determined through the use of competitive binding assays, where interference with binding of a known ligand or substrate is measured in the presence of a potential modulator. Either the modulator, the known ligand, or substrate is bound first; then the competitor is added. After the protein is washed, interference with binding, either of the potential modulator or of the known ligand or substrate, is determined. Often, either the potential modulator or the known ligand or substrate is labeled.

A cell-based assay can be used in which the TMAdV is expressed in a cell, and functional, physical, chemical and phenotypic changes are assayed to identify viral modulators. Any suitable functional effect can be measured as described herein, in addition to viral inhibition assays as are well known in the art. The TMAdV can be naturally occurring or recombinant. Also, fragments of the TMAdV or chimeric proteins can be used in cell based assays. In addition, point mutants in essential residues required by the catalytic site can be used in these assays.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *I Amer. Chem. Soc.* 116:2661 (1994)), oligocarbamates (Cho et al., *Science* 261:1303 (1993)), and/or peptidyl phosphonates (Campbell et al., *I Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

A solid state or soluble high throughput assaying using a TMAdV, or a cell or tissue expressing a TMAdV, either naturally occurring or recombinant can be used. A solid phase based in vitro assay can be used in a high throughput format can be used where TMAdV is attached to a solid phase. Any one of the assays described herein can be adapted for high throughput screening.

In high throughput assays, either soluble or solid state, it is possible to screen up to several thousand different modulators or ligands in a single day. This methodology can be used for TMAdV in vitro, or for cell-based or membrane-based assays comprising a TMAdV. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage. A tag for covalent or non-covalent binding can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like (see, e.g., Pigott & Power, *The Adhesion Molecule Facts Book I* (1993)). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, polyethylene glycol linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (e.g., Merrifield, *J Am. Chem. Soc.* 85:2149-2154 (1963) (describing solid phase synthesis of, e.g., peptides); Geysen et al., *J Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates)). Non-chemical approaches for fixing tag binders to substrates include other common methods, such as heat, cross-linking by UV radiation, and the like.

The compounds tested as modulators of TMAdV can be any small organic molecule, or a biological entity, such as a protein, e.g., an antibody or peptide, a sugar, a nucleic acid, e.g., an antisense oligonucleotide or a ribozyme or siRNA, or a lipid. Alternatively, modulators can be genetically altered versions of a TMAdV. Typically, test compounds will be small organic molecules, peptides, circular peptides, siRNA, antisense molecules, ribozymes, and lipids.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

Treating/Preventing TMAdV

Embodiments described herein further relate to the therapeutic, prophylactic and research uses of various techniques to block or modulate the expression of TMAdV viral proteins or propagation of the virus. Modulators of TMAdV useful for treating or preventing TMAdV can include, but is not limited to, genetically modified versions of TMAdV, e.g., versions with altered activity, as well as naturally occurring and synthetic ligands, substrates, antagonists, agonists, antibodies, peptides, cyclic peptides, aptamers, nucleic acids, antisense molecules, ribozymes, siRNA molecules, miRNA molecules, and small chemical molecules, as is well known in the art.

Further described herein are TMAdV vaccines for therapeutic or prophylactic purposes. Within certain aspects, TMAdV virus, proteins or peptides and immunogenic fragments thereof, and/or polynucleotides, as well as anti-TMAdV antibodies and/or T cells, can be incorporated into pharmaceutical compositions or immunogenic compositions. Whole virus vaccines (live and attenuated, or replication incompetent, or killed) or subunit vaccines, such as structural or non-structural TMAdV proteins or immunogenic fragments thereof, can be used to treat or prevent TMAdV infections by eliciting an immune response in a subject. Alternatively, a pharmaceutical composition can comprise an antigen-presenting cell (e.g., a dendritic cell) transfected with a TMAdV polynucleotide such that the antigen-presenting cell expresses a TMAdV peptide.

Nucleic acid vaccines encoding a genome, structural protein or non-structural protein or a fragment thereof of TMAdV can also be used to elicit an immune response to treat or prevent TMAdV infection. Numerous gene delivery techniques are well known in the art, such as those described by Rolland (1998) *Crit. Rev. Therap. Drug Carrier Systems* 15:143-198, and references cited therein. Appropriate nucleic acid expression systems contain the necessary DNA sequences for expression in the patient (such as a suitable promoter and terminating signal). In a preferred embodiment, the DNA can be introduced using a viral expression system (e.g., vaccinia, pox virus, retrovirus, or adenovirus), which can involve the use of a non-pathogenic (defective), replication competent virus. Suitable systems are disclosed, for example, in Fisher-Hoch et al. (1989) *Proc. Natl. Acad. Sci. USA* 86:317-321; Flexner et al. (1989) *Ann. N.Y. Acad. Sci.* 569:86-103; Flexner et al. (1990) *Vaccine* 8:17-21; U.S. Pat. Nos. 4,603,112, 4,769,330, 4,777,127 and 5,017,487; WO 89/01973; GB 2,200,651; EP 0,345,242; WO 91/02805; Berkner (1988) *Biotechniques* 6:616-627; Rosenfeld et al. (1991) *Science* 252:431-434; Kolls et al. (1994) *Proc. Natl. Acad. Sci. USA* 91:215-219; Kass-Eisler et al. (1993) *Proc. Natl. Acad. Sci. USA* 90:11498-11502; Guzman et al. (1993) *Circulation* 88:2838-2848; and Guzman et al. (1993) *Cir. Res.* 73:1202-1207. Techniques for incorporating DNA into such expression systems are well known to those of ordinary skill in the art. The DNA can also be "naked," as described, for example, in Ulmer et al. (1993) *Science* 259:1745-1749 and reviewed by Cohen (1993) *Science* 259:1691-1692. The uptake of naked DNA can be increased by coating the DNA onto biodegradable beads, which are efficiently transported into the cells. It will be apparent that a vaccine can comprise both a polynucleotide and a polypeptide component. Such vaccines can provide for an enhanced immune response.

Vaccine preparation is generally described in, for example, Powell and Newman, eds., *Vaccine Design* (the subunit and adjuvant approach), Plenum Press (NY, 1995). Vaccines can be designed to generate antibody immunity and/or cellular immunity such as that arising from CTL or CD4+ T cells.

A non-specific immune response enhancer can be any substance that enhances an immune response to an exogenous antigen. Examples of non-specific immune response enhancers include adjuvants, biodegradable microspheres (e.g., polylactic galactide) and liposomes (into which the compound is incorporated; see, e.g., U.S. Pat. No. 4,235,877). Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, can also be used as adjuvants.

Pharmaceutical Compositions

Pharmaceutical compositions and vaccines within the scope of the present invention can also contain other compounds, which can be biologically active or inactive. For example, one or more immunogenic portions of other antigens can be present, either incorporated into a fusion polypeptide or as a separate compound, within the composition or vaccine. Polypeptides can, but need not be, conjugated to other macromolecules as described, for example, within U.S. Pat. Nos. 4,372,945 and 4,474,757. Pharmaceutical compositions and vaccines can generally be used for prophylactic and therapeutic purposes.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Such compositions can also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention can be formulated as a lyophilizate. Compounds can also be encapsulated within liposomes using well known technology.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to affect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences,* $17^{th}$ ed., 1989). Administration can be in any convenient manner, e.g., by injection, oral administration, inhalation, transdermal application, or rectal administration.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

Pharmaceutical and vaccine compositions can be presented in unit-dose or multi-dose containers, such as sealed ampoules or vials. Such containers are preferably hermetically sealed to preserve sterility of the formulation until use. In general, formulations can be stored as suspensions, solutions or emulsions in oily or aqueous vehicles. Alternatively, a vaccine or pharmaceutical composition can be stored in a freeze-dried condition requiring only the addition of a sterile liquid carrier immediately prior to use.

Kits

The invention further provides diagnostic reagents and kits comprising one or more such reagents for use in a variety of diagnostic assays, including for example, immunoassays such as ELISA and "sandwich" type immunoassays, as well as nucleic acid assay, e.g., PCR assays. In a related embodiment, the assay is performed in a flow-through or strip test format, wherein the binding agent is immobilized on a membrane, such as nitrocellulose. Such kits can preferably include at least a first peptide, or a first antibody or antigen binding fragment of the invention, a functional fragment thereof, or a cocktail thereof, or a first oligo pair, and means for signal generation. The kit's components can be pre-attached to a solid support, or can be applied to the surface of a solid support when the kit is used. The signal generating means can come pre-associated with an antibody or nucleic acid of the invention or can require combination with one or more components, e.g., buffers, nucleic acids, antibody-enzyme conjugates, enzyme substrates, or the like, prior to use.

Kits can also include additional reagents, e.g., blocking reagents for reducing nonspecific binding to the solid phase surface, washing reagents, enzyme substrates, enzymes, and the like. The solid phase surface can be in the form of microtiter plates, microspheres, or other materials suitable for immobilizing nucleic acids, proteins, peptides, or polypeptides. An enzyme that catalyzes the formation of a chemiluminescent or chromogenic product or the reduction of a chemiluminescent or chromogenic substrate is one such component of the signal generating means. Such enzymes are well known in the art. Where a radiolabel, chromogenic, fluorigenic, or other type of detectable label or detecting means is included within the kit, the labeling agent can be provided either in the same container as the diagnostic or therapeutic composition itself, or can alternatively be placed in a second distinct container means into which this second composition can be placed and suitably aliquoted. Alternatively, the detection reagent and the label can be prepared in a single container means, and in most cases, the kit will also typically include a means for containing the vial(s) in close confinement for commercial sale and/or convenient packaging and delivery.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1: Identification of a New Titi Monkey Adenovirus (TMAdV)

Materials and Methods

The California National Primate Research Center (CNPRC)

The California National Primate Research Center (CNPRC) is a part of the National Primate Research Centers At the beginning of 2009, the CNPRC maintained a colony of 74 New World titi monkeys (*Callicebus cupreus*) for studies of social behavior. Eighty-eight percent of the CNPRC titi monkey population (n=65) occupied 1 quadrant in 1 animal building. The other 3 quadrants housed 133 rhesus macaques (*Macaca mulatta*). Nearby outdoor enclosures containing rhesus macaques and cynomolgus macaques (*Macaca fasicularis*) surrounded this building.

An outbreak of fluminant pneumonia lasted from May 14, 2009 until Aug. 5, 2009. All titi monkeys demonstrating clinical signs of the outbreak were housed in the animal building. Three additional titi monkeys were moved into the building on May 28, 2009, reflecting a total at-risk population of 68 animals. Over the past 6 years, there were no new introductions of titi monkeys into the CNPRC; over the past 2 years, there were no new introduction of rhesus macaques.

Microbial Testing

Bacterial, mycoplasma, and fungal cultures were performed at the CNPRC. Clinical samples were also sent to an outside laboratory (Focus Diagnostics, Cypress, Calif.) for respiratory viral testing by centrifugation-enhanced shell vial culture followed by direct fluorescent antibody staining for 8 viruses (respiratory syncytial virus, adenovirus, influenza virus A and B, parainfluenza virus types 1, 2, and 3, and human metapneumovirus).

Gross, Histophathological, and Ultrastructural Analyses

Gross and histopathological analyses of post-mortem tissues were performed by a board-certified veterinary pathologist at the Morphology Core of the CNPRC. At necropsy, tissue samples from the trachea, lung, and liver were collected and fixed in 10% formalin. Tissues were routinely processed and embedded in paraffin. 3-μm sections were stained with hematoxylin and eosin (HE) and examined by light microscopy. For transmission electron microscopy, tissue fragments (2×2 mm) were excised from paraffin blocks of lung, deparaffinized, and processed as previously described (Woods, et al., *Vet Pathol* 33:125 (1996)).

Nucleic Acid Extraction and cDNA Library Preparation

Total nucleic acid was extracted from body fluid or swab samples using commercially available kits (Qiagen, Valencia, Calif.). 200 μL of sample were passed through a 0.22 μm filter (Millipore, Temecula, Calif.) to remove bacteria and cellular debris and then treated with Turbo DNase (Ambion, Culver City, Calif.) to degrade host genomic DNA prior to extraction. For tissue samples, lung or liver tissue was homogenized in an 15 mL Eppendorf tube using a disposable microtube pestle (Eppendorf, San Diego, Calif.) and scapel; RNA extraction was then performed using TRIzol LS (Invitrogen, Carlsbad, Calif.) followed by isopropanol precipitation and two washes in 70% ethanol. Extracted nucleic acid was amplified using a random PCR method to generate cDNA libraries for Virochip and deep sequencing analyses as previously described (Wang, et al., *PNAS,* 99:150807 (2002); Greninger, et al., *PloS ONE* 5:e13381 (2010)).

Virochip Analysis

Virochip analysis was performed as previously described (Wang, et al., *PNAS,* 99:150807 (2002); Greninger, et al., *PloS ONE* 5:e13381 (2010)). Briefly, samples were labeled with Cy3 or Cy5 fluorescent dye, normalized to 10 μmol of incorporated dye, and hybridized overnight using the Agilent Gene Expression Hybridization kit (Agilent Technologies, Santa Clara, Calif.). The current 8×60 k Virochip arrays used in this study contain 36,000 probes representing all viral species in GenBank, and combine probes from all previous Virochip designs (Greninger, et al., *PloS ONE*: e13381 (2010). Slides were scanned at 2 μm resolution using an Agilent DNA Microarray Scanner. Virochip microarrays were analyzed with Z-score analysis (Chiu, et al., *Clin Infect Dis,* 43:e71 (2006)), hierarchical cluster analysis (Eisen, et al., *PNAS* 95:14863 (1998)), and E-Predict, an automated computational algorithm for viral species prediction from microarrays (Urisman, et al., *Genome Biol* 6:R78 (2005)). Only Z-score analysis, a method for assessing the statistical significance of individual Virochip probes, yielded a credible viral signature on the microarray.

PCR Screening

Consensus primers derived initially from a highly conserved region of the hexon gene to confirm the Virochip finding of a novel adenovirus by PCR. From the sequence of a resulting 301-bp amplicon, a set of specific PCR primers was designed for TMAdV. The TMAdV-specific PCR was performed using a reaction mixture consisting of 17 μL of water, 2.5 μL of 10× Taq buffer, 1 μL of $MgCl_2$ (50 mM), 0.5 μL of deoxynucleoside triophosphates (dNTPs; 12.5 mM), 0.5 μL of each primer (10 μM), and 0.5 μL of Taq polymerase (Invitrogen, Carlsbad, Calif.), in a final volume of 25 μL. Conditions for the PCR reaction were 40 cycles of 94° C. for 30 s, 50° C. for 45 s, and 72° C. for 1 min. Amplicons were purified on a 2% agarose gel, cloned into plasmid vectors using TOPO TA (Invitrogen, Carlsbad, Calif.), and sent to an outside company (Elim Biopharmaceuticals, Hayward, Calif.) for Sanger sequencing in both directions using vector primers M13F and M13R.

PCR assays commonly used to detect human adenoviruses in clinical or public health settings were analyzed to determine the ability to detect TMAdV. Adenovirus PCR was performed on 12 TMAdV-positive clinical samples using an additional 6 pairs of primers, according to previously published protocols (Hierholzer, et al., *J Clin Microbiol* 31:1886 (1993); Lee, et al., *J Clin Microbiol* 45:2626 (2007); Xu, et al., *J Clin Microbiol* 38:4114 (2000)). 5 of the 6 primer pairs, including all of the pairs designed to detect human respiratory adenoviruses, completely failed to amplify TMAdV from positive clinical samples, while the remaining pair was only 75% sensitive relative to TMAdV-specific PCR Whole Genome Sequencing To facilitate whole-genome sequencing of TMAdV, cDNA libraries were prepared and amplified for deep sequencing from lung tissue and a lung swab sample from two different monkeys using previously published protocols (Sorber, et al., *PloS One* 3:e495 (2008)). Briefly, libraries were cleaved with a Type IIs restriction endonuclease (GsuI) and truncated adapters were ligated on the resulting strand ends. Full-length adapters were added via an additional 15 cycles of PCR. Amplified libraries were size-selected on a 2% agarose gel at approximately 350 bp average length and then sent an outside company (Elim Biopharmaceuticals, Hayward, Calif.) for deep sequencing on an Illumina Genome Analyzer IIx (Illumina, San Diego, Calif.). Paired-end reads were sequenced for 73 cycles in each direction. Paired-end reads were subsequently filtered to eliminate low-complexity sequences with a Lempel-Ziv-Welch (LZW) compression ratio below 0.4, Welch, T. A. *Computer* 17, 8-19 (1984), split into individual reads, and stripped of any remaining primer sequences using BLASTN alignments (word size=11, E-value=$1\times10^{-5}$). After low-complexity filtering and primer trimming, 11,950,557 sequence reads remained, with each read consisting of 67 nucleotides, for a total of ~800 megabases of sequence. Remaining reads were then aligned to the genome sequence of sAd18, the closest relative to TMAdV (FIG. 2B) and to a database consisting of all adenovirus genomes and partial sequences deposited in GenBank by BLASTN (word size=11, E-value=$1\times10^{-5}$) and TBLASTX (word size=11, E-value=$1\times10^{-5}$). Reads that aligned to adenoviruses were then used to assemble portions of the TMAdV genome with Geneious software (version 3.6.5) Drummond, A., et al. Geneious v5.3.4, employing the sAd18 genome as a reference sequence and requiring a 20-bp minimum overlap and 95% overlap identity. Aligning reads were also used to design PCR primers to fill in remaining gaps in the TMAdV genome. Amplicons derived from specific TMAdV PCR primers were gel-purified, cloned, and sequenced as described above. The 5' end corresponding to the inverted terminal repeat (ITR) of TMAdV was obtained by PCR with a forward degenerate consensus primer and a reverse TMAdV-specific primer.

Structural Features and Phylogenetic Analysis

To identify coding regions in the TMAdV genome, the fully annotated genomic sequence of simian adenovirus 21 (sAd21) was used as a reference. First, the two genomes and identified all ORFs that were present were aligned with Geneious. An overlapping ORF that best matched the corresponding ORF in the annotated reference genome was considered to be correct. For adenovirus genes that are spliced (e.g. E1A), the identification of a GT-AG intron start-stop signal was used to pinpoint the correct ORF. To verify the accuracy of the coding sequence, the sequence of each identified ORF was aligned to a database containing all adenoviral proteins in GenBank by BLASTX. Alignments were then manually examined to ensure that all ORF assignments were correct.

To generate the phylogeny trees, representative whole-genome sequences from simian and human members of Groups A-G and non-mammalian adenoviruses were first compiled from GenBank. Multiple sequence alignments of the hexon and polymerase genes were then constructed with Geneious. Sliding window analysis (window size, 200 bp; step size 20 bp) was performed with Simplot (Lole, K. S., et al., *J Virol* 73, 152-160 (1999)). Bootscanning was performed using the Jukes and Cantor method, also with Simplot (window size: 200 bp; step size, 20; 1000 replicates). Pairwise amino acid alignments between TMAdV proteins and corresponding proteins in other adenoviruses (Table 3) were performed using Geneious.

Culturing

A549 (human lung adenocarcinoma), PMK (primary rhesus macaque kidney), and BSC-1 (African green monkey kidney epithelial) cell lines were obtained from the Viral and Rickettsial Disease Laboratory (VRDL) branch of the California Department of Public Health. Cell lines were maintained in Dulbecco's modified Eagle's medium (DMEM) supplemented with 1× nonessential amino acids (Invitrogen, Carlsbad, Calif.), 10% fetal bovine serum, 100 U of penicillin/mL, and 100 μg of streptomycin/mL. Anti-SV40 antibodies were added to the cell culture media to prevent growth of SV40 polyomavirus. Clinical samples were clarified by centrifugation for 10 min×4,000×g and passage through a 0.2-μm filter. After achieving 80-90% confluency, cell cultures were inoculated with XXX μL of clinical sample or passaged viral supernatant. Viral replication was monitored over 14 days by visual inspection under light microscopy for cytopathic effect (CPE). To confirm the generation of infectious virus, viral supernatants were quantitated by an end-point dilution assay.

Microarray and Nucleotide Sequence Accession Numbers

All Virochip microarrays used in this study have been submitted to the NCBI GEO database (study accession number GSE26898; microarray accession numbers GSM662370-GSM662391; microarray design accession number GPL 11662). The annotated, whole-genome sequence of TMAdV has been submitted to GenBank (accession number HQ913600). Deep sequencing reads have been submitted to the NCBI Sequence Read Archive (accession number SRA031285).

Results

Outbreak of Fulminant Pneumonia in a Titi Monkey Colony

A healthy adult titi monkey presented on May 14, 2009 with cough, lethargy, and decreased appetite (FIG. 1A, T30). Despite treatment with intravenous fluids and antibiotics, the animal died in 5 days. A second case presented 4 weeks later. In the interim period, 3 healthy titi monkeys were relocated from a separate building, including 2 into the cage formerly occupied by the index case (FIG. 1A, T31 and T32), reflecting an at-risk population of 68. Over the next 2 months, 21 additional monkeys presented with clinical signs similar to those shown by the index case, including one of the relocated monkeys (attack rate=23/68, or 34%) (FIGS. 1A and 1B). Clinical signs in affected animals included cough, lethargy, poor appetite, tachypnea, and abdominal breathing. These symptoms progressed to overt respiratory distress and death within an average of 8 days. Chest radiographs typically revealed diffuse interstitial pulmonary changes and bronchoalveolar consolidation indicative of pneumonia. Right middle lobe involvement was predominant (FIG. 1C). Animals displaying clinical signs were quarantined and aggressively treated by veterinarians with supplemental oxygen, anti-inflammatory medications, broad-spectrum antibiotics, and antivirals (oseltamivir and/or ribavirin). In total, 19 animals died from the illness during the outbreak (case fatality rate=83%). Only 4 monkeys survived, even though the at-risk population consisted of apparently healthy adults and juveniles. Interestingly, none of the 133 rhesus macaques (*Macaca mulatta*) housed in the same building became sick during the outbreak, and neither did any of the Old World monkeys from surrounding outdoor colonies of rhesus and cynomolgus macaques (*Macaca fascicularis*).

Figure 1:
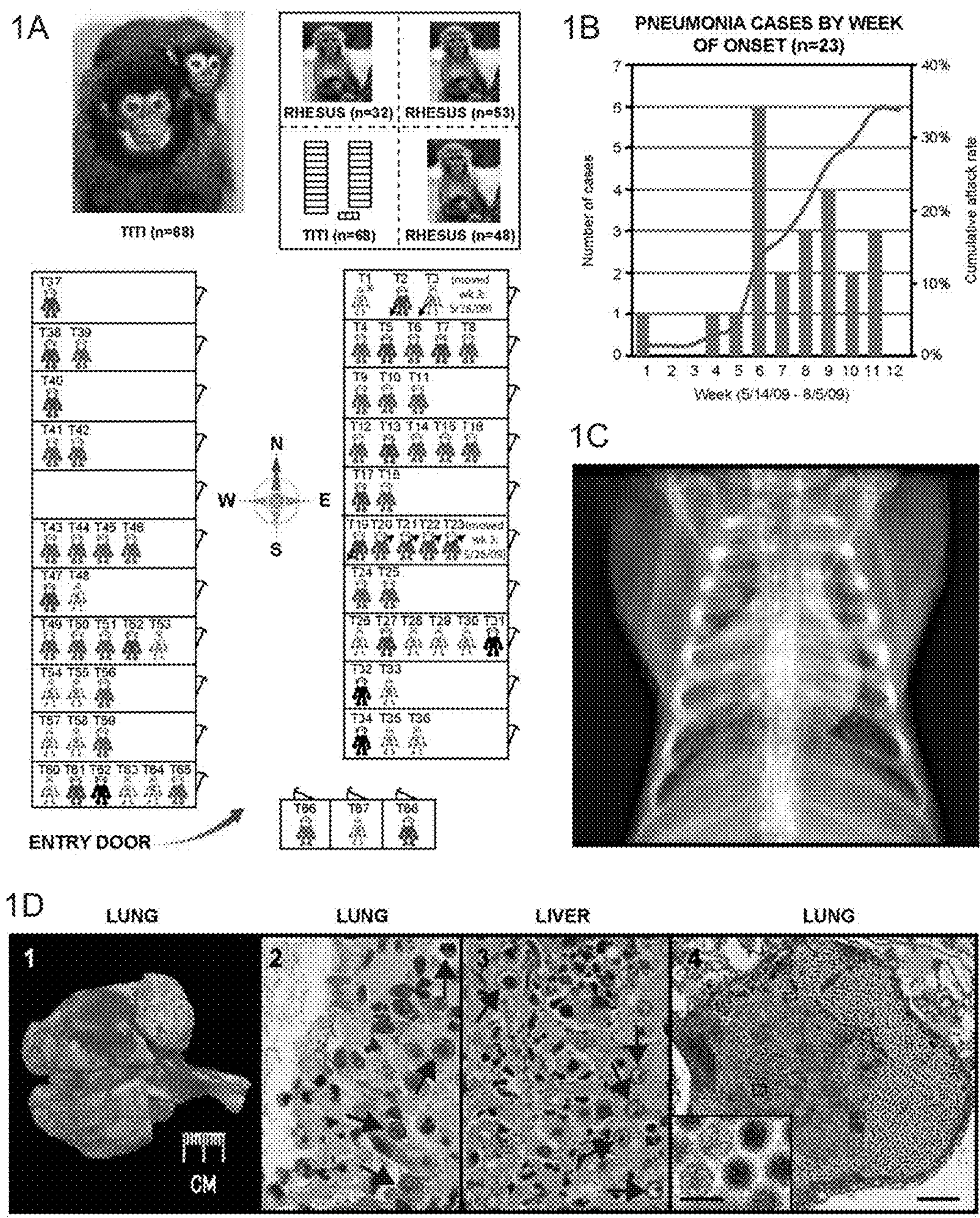
FIG. 1A-FIG. 1D illustrate the clinical and epidemiologic features of the titi monkey outbreak. (A) Map of the titi monkey cages situated in one quadrant of a building, showing the locations of asymptomatic, at-risk monkeys (brown or green), affected surviving monkeys (black), and monkeys who died from their illness (skeleton). 3 monkeys were moved into the building (arrows pointing down and to the left) and 4 monkeys out of the building (arrows pointing up and to the right) during the 3rd week of the outbreak. The upper left photograph shows an image of an adult male titi monkey and his infant. The upper right inset shows the location of the titi monkey cages relative to other rhesus monkey cages in the building. Asymptomatic monkeys with positive serum antibody titers to TMAdV 4 months after the outbreak are shown in green. (B) Epidemic curve of the outbreak, with the number of cases in blue and cumulative attack rate in red. (C) Anteroposterior chest radiograph of an affected titi monkey, showing bilateral basilar infiltrates and a prominent right middle lobe consolidation. (D) 1—gross photograph of lungs at necropsy; the lungs failed to fully collapse upon opening the chest, and a single ~1.5 cm focus of dark red discoloration (hemorrhage) can be seen in the left caudal lobe. 2—photomicrograph of H&E stained lung tissue showing a severe diffuse necrotizing bronchopneumonia characterized by the presence of hemorrhage and intranuclear inclusions (arrows). 3—photomicrograph of H&E stained liver tissue showing a multifocal necrotizing hepatitis with numerous intranuclear inclusions (arrows). 4—transmission electron micrograph of an affected lung alveolus (scale bar=1 μm) filled with adenovirus-like particles (inset, scale bar=0.1 μm).
Figure 2:
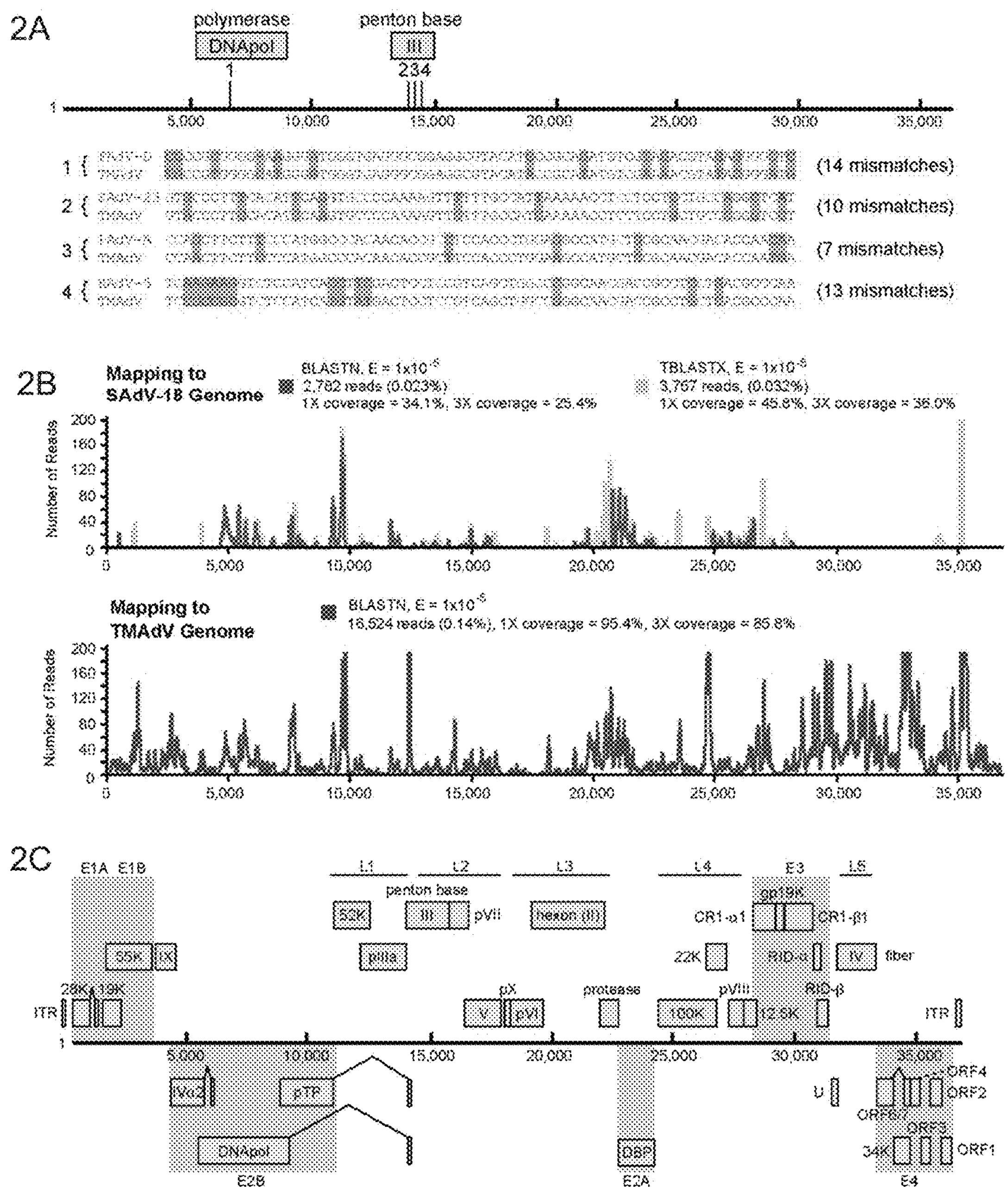
FIG. 2A-FIG. 2C illustrate the discovery and whole-genome characterization of the novel adenovirus TMAdV. (A) The locations of the 4 Virochip probes derived from adenovirus sequences and used to detect TMAdV are mapped onto the ~37 kB genome. The 4 Virochip probe sequences are also aligned with the corresponding sequence in the TMAdV genome, with mismatches highlighted in pink. (B) Coverage map of deep sequencing reads corresponding to TMAdV using BLASTN (blue) and TBLASTX (transparent blue) alignments to the simian adenovirus SAdV-18. The actual coverage achieved by deep sequencing as determined by alignments to the fully sequenced genome of TMAdV is much higher (red). (C) Genome organization of TMAdV. Predicted protein coding regions are shown as boxes. Boxes above the central black line represent open reading frames (ORFs) that are encoded on the forward strand, while boxes underneath the black line represent reverse-strand encoded ORFs. Early region ORFs are shaded in gray. The x-axis refers to the nucleotide position along the ~37 k genome of TMAdV. Abbreviations: FAdV, fowl adenovirus; SAdV, simian adenovirus; PAdV, porcine adenovirus; HAdV, human adenovirus, TMAdV, titi monkey adenovirus.

Gross necropsy findings were similar in all titi monkeys and were characterized primarily by diffuse, consolidated pneumonias, with prominent right middle lobe involvement. Occasional evidence of fibrinous pleuritis, pericardial/pleural edema, and hemorrhage was found (FIG. 1D-1). Some livers, spleens, and lymph nodes were found to be abnormally enlarged. Hepatic necrosis and hemorrhage, along with ascites, were sometimes appreciated. On histologic examination, respiratory epithelium was found to be completely obliterated. Lung architecture was destroyed, and prominent intranuclear inclusion bodies were observed (FIGS. 1D-2 and 1D-3).

A routine microbiological workup for infectious causes of the outbreak, including bacterial, mycoplasma, and fungal cultures, was negative. Respiratory viral testing failed to detect evidence of respiratory syncytial virus, adenovirus, influenza virus A and B, human metapneumovirus, and parainfluenza virus types 1, 2, and 3.

Virochip Identification, PCR Screening and Electron Microscopic (EM) Confirmation of TMAdV Given the clinical presentation of an acute viral respiratory illness and the appearance of intranuclear inclusion bodies on histological examination, it was suspected that a virus that had eluded detection by conventional assays was the cause of the titi monkey outbreak. Nasal, lung, and liver swab samples collected during necropsy were analyzed using the Virochip. Microarrays were analyzed using ranked Z-scores (Chiu, C. Y., et al. *Clin Infect Dis,* 43, e71-76 (2006)), with 5 of the top 50 probes on the Virochip corresponding to adenoviruses and mapping to 4 different regions in the adenovirus genome (FIG. 2A). The 5 probes were derived from 3 different Adenoviridae genera, suggesting the presence of a divergent adenovirus that was not a member of any previously known species.

Using consensus primers (Echavarria, et al., *J Clin Microbiol* 36:3323 (1998)), we amplified a 301 bp fragment of the adenovirus from the hexon gene. The fragment shared ~86% nucleotide identity with its closest phylogenetic relatives, the human group D adenoviruses, and the newly identified adenovirus was designated TMAdV, or titi monkey adenovirus. Specific PCR for TMAdV was used to screen body fluids and tissues from affected monkeys. PCR results were positive from post-necropsy liver and lung tissues as well as from sera, oral swabs, and nasal swabs collected at time of quarantine in 8 different affected monkeys, but were negative from nasal swabs in 3 asymptomatic control animals (Table 1). To confirm the presence of virus in diseased tissues, lung tissue from affected monkeys was examined by transmission electron microscopy, revealing abundant icosahedral particles characteristic of adenovirus filling the alveoli (FIG. 1D-4). Next, to assess persistent subclinical infection from TMAdV, convalescent sera from surviving affected monkeys 1 month post-outbreak was analyzed (n=4). All serum samples were negative for TMAdV by PCR. To assess potential TMAdV shedding, stool samples collected from all cages housing titi monkeys (n=22) were analyzed by PCR, and were found to be negative. In addition, TMAdV was analyzed in rectal swab samples from rhesus macaques housed in the same building as the titi monkeys (n=26) and in wild rodent droppings (n=2) from rodents living near the at-risk titi monkey room. All macaque and rodent fecal samples were negative for TMAdV by PCR.

TABLE 1

PCR screening for TMAdV.

| Sample | Sample Type | PCR Result | Date Presenting with Clinical Signs | Date of Necropsy |
|---|---|---|---|---|
| Affected, at-risk titi monkeys (died) | | | | |
| T1 | serum[§] | − | May 14, 2009 | May 19, 2009 |
| T26 | serum[¶] | + | Jul. 23, 2009 | Jul. 30, 2009 |
| T28 | conjunctival swab[¶] | + | Jul. 16, 2009 | Jul. 25, 2009 |
| | nasal swab[¶] | + | | |
| | liver swab[¶] | + | | |
| | lung swab[¶] | + | | |
| T29 | serum[¶] | + | Jul. 26, 2009 | Jul. 31, 2009 |
| T30 | serum[¶] | − | Jul. 25, 2009 | Jul. 30, 2009 |
| T33 | lung swab[¶] | + | Jun. 23, 2009 | Jun. 29, 2009 |
| | nasal swab[¶] | + | | |
| T36 | lung swab[¶] | + | Jul. 7, 2009 | Jul. 14, 2009 |
| | lung swab[¶] | + | | |
| T60 | serum[¶] | − | Jul. 15, 2009 | Jul. 22, 2009 |
| T63 | serum[¶] | − | Jun. 20, 2009 | Aug. 1, 2009 |
| T67 | nasal swab[#] | − | Jul. 7, 2009 | Aug. 13, 2009 |
| | nasal swab[¶] | + | | |
| Affected, at-risk titi monkeys (survived) | | | | |
| T31 | serum* | − | Jul. 10, 2009 | N/A |
| T32 | serum* | − | Jul. 12, 2009 | N/A |
| T34 | serum* | − | Jun. 23, 2009 | N/A |
| T62 | serum* | − | Jul. 8, 2009 | N/A |
| Asymptomatic at-risk and minimal-risk titi monkeys | | | | |
| T27 | throat swab (n = 1)[¶] | − | N/A | N/A |
| at-risk titi | stool from cages (n = 14)* | − | N/A | N/A |
| at-risk titi | serum (n = 29)* | − | N/A | N/A |
| minimal-risk titi | oral swab (n = 3)[¶] | − | N/A | N/A |
| minimal-risk titi | stool from cages (n = 5)* | − | N/A | N/A |
| minimal-risk titi | serum (n = 8)* | − | N/A | N/A |
| minimal-risk titi | stool from cages (n = 8)* | − | N/A | N/A |
| Other | | | | |
| rhesus | rectal swabs (n = 26)* | − | N/A | N/A |
| human | serum (n = 15)[∞] | − | N/A | N/A |
| rodent | droppings (n = 2)* | − | N/A | N/A |

[§]= initial case;
[#]= collected prior to outbreak;
[¶]= collected during outbreak;
*= collected 2 months after outbreak;
[∞]= collected 4 months after outbreak. For titi monkey cage designations (TXX), please refer to FIG. 1.

Whole Genome Sequencing, Features, and Phylogenetic Analysis of TMAdV

To facilitate whole-genome sequencing of TMAdV, deep sequencing of a lung swab from one affected titi monkey and lung tissue from another affected monkey was performed. Out of ~11.9 million high-quality reads, 2,782 reads and 3,767 reads aligned to the SAdV-18 genome by BLASTN (FIG. 2B, blue) and TBLASTX (FIG. 2B, transparent blue), respectively, with reads mapping to sites across the genome. De novo assembly of the complete TMAdV genome from reads that aligned to SAdV-18 was not possible due to insufficient sequence coverage (<46%). The poor apparent coverage was the result of high sequence divergence of the TMAdV genome from the genomes of known adenoviruses, which hindered the identification of most of the 16,524 actual deep sequencing reads derived from TMAdV (FIG. 2B, red). Thus, after partial assembly of TMAdV using overlapping reads aligning to the SAdV-18 g TMAdV was found to be 36,842 base pairs in length, with a base composition of 20.8% A, 29.8% C, 29.8% G, and 19.6% T, and a GC content of 59.6%, comparable to that of adenoviral species Groups C, D, and E in the *Mastadenovirus* genus. The deduced genomic structure of TMAdV was also similar to that of other mastadenoviruses and consists of 34 open reading frames (FIG. 2C).

Figure 4:
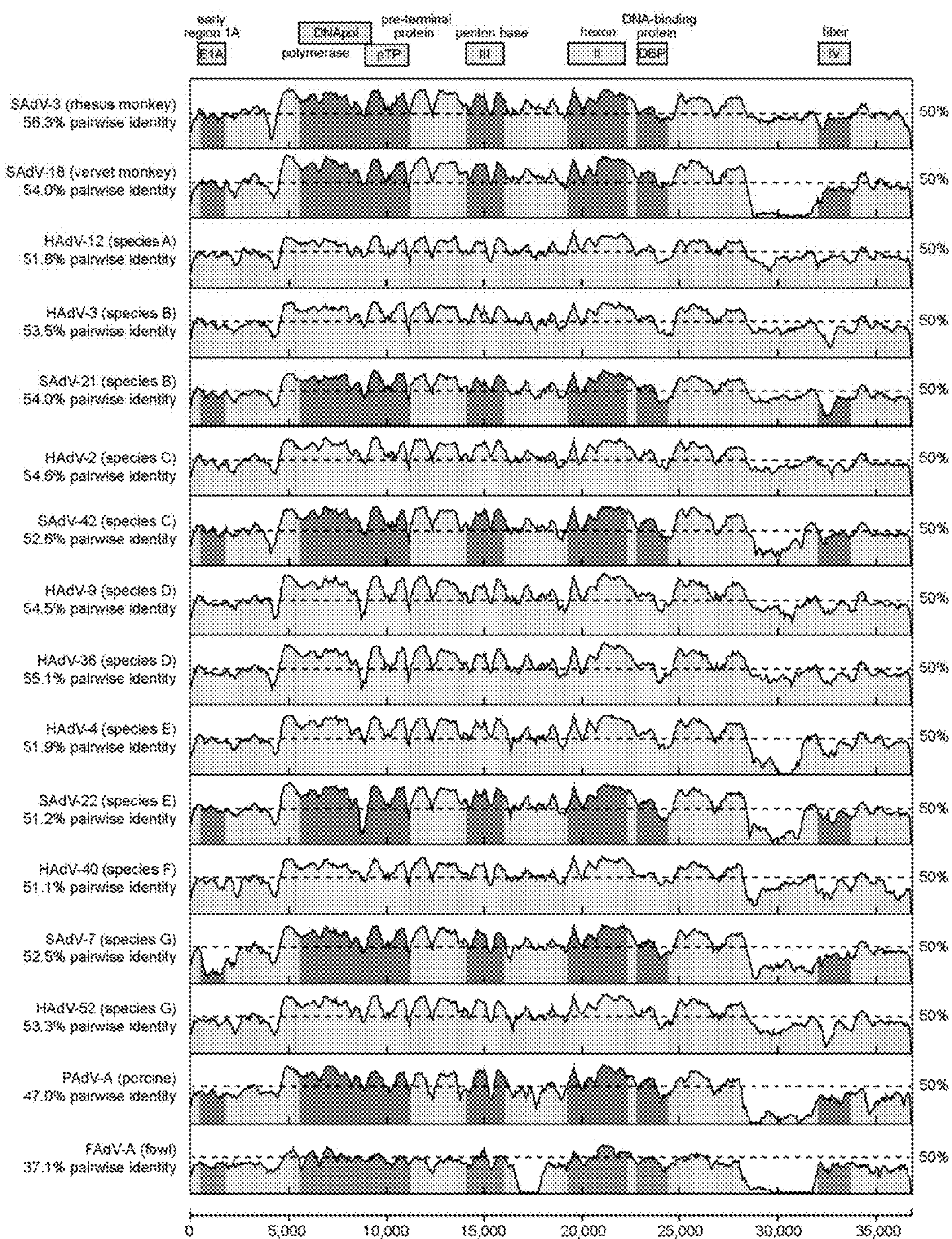
FIG. 4 shows scanning pairwise alignment of representative adenoviruses with TMAdV. The scanning nucleotide pairwise identities of TMAdV relative to representative human (yellow) or simian (brown) adenoviruses in species A-G, porcine adenovirus (red), or fowl adenovirus (green) are shown. The window size is 400 bp with a step size of 40 bp. The x-axis refers to the nucleotide position along the ~37 k genome of TMAdV. Abbreviations: HAdV, human adenovirus; SAdV, simian adenovirus; PAdV, porcine adenovirus; FAdV, fowl adenovirus.
Figure 7:
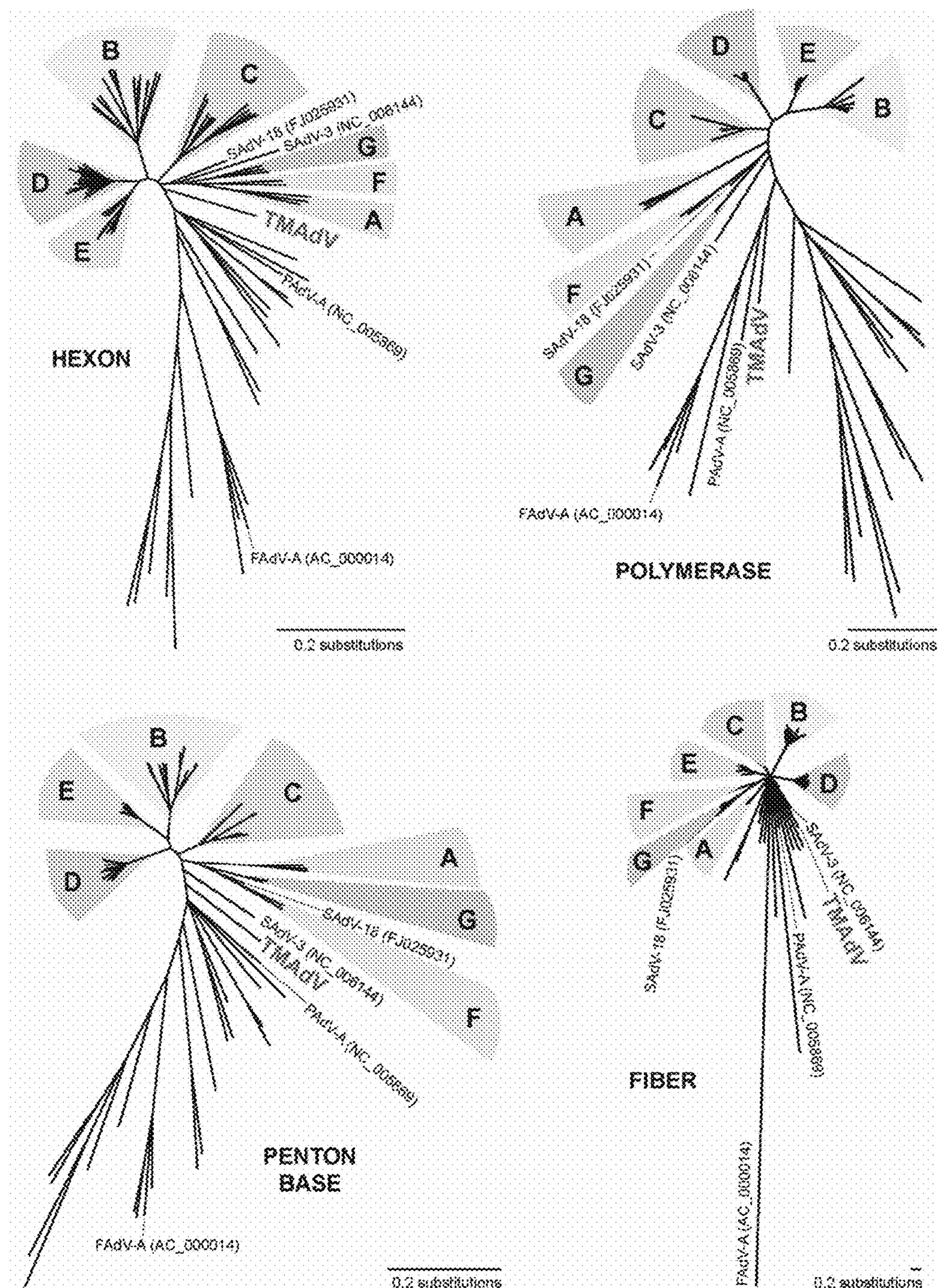
FIG. 7 illustrates phylogenetic analysis of the hexon, polymerase, penton base, and fiber genes of TMAdV. A multiple sequence alignment of selected genes from all 95 unique, fully-sequenced adenovirus genomes in GenBank and TMAdV is performed and the results displayed as a radial phylogenetic tree. The branch corresponding to TMAdV is highlighted in boldface red. Abbreviations: HAdV, human adenovirus, SAdV, simian adenovirus; PAdV, porcine adenovirus; FAdV, fowl adenovirus.

Whole-genome phylogenetic analysis placed TMAdV in an independent species group separate from the known human adenoviral species A-G (FIG. 3). Among all 95 fully-sequenced adenovirus genomes in GenBank, the closest simian adenoviral relatives to TMAdV were SAdV-3, SAdV-18, and SAdV-21, with pairwise nucleotide identities ranging from 54.0% to 56.3% (FIG. 4). The closest human adenoviral relatives were the species D adenoviruses, which share 54.3% to 55.1% identity to TMAdV, with human adenoviruses of other species slightly less similar (51.1%-54.6%). The placement of TMAdV into a separate group by phylogenetic analysis was also observed when looking individually at the hexon, polymerase, penton base, and fiber genes (FIG. 7). Scanning nucleotide pairwise identity plots revealed that, among the major adenovirus genes, the DNA polymerase and hexon are more conserved, whereas the E1A and fiber are more divergent (FIG. 4). The significant overall sequence divergence of TMAdV from known human and simian adenoviruses is highlighted by the finding that PAdV-A (porcine adenovirus A), a non-primate mammalian adenovirus, shared only a slightly less similar whole-genome pairwise identity to TMAdV of 47.0% (FIG. 4). In fact, in the DNA polymerase gene, TMAdV shared a pairwise identity with PAdV-A of 67.2%, comparable to its pairwise identities with the other human adenoviruses, 59%-

71.7% (FIGS. 4 and 7). Although TMAdV was found to be highly divergent from other adenoviruses, different isolates of TMAdV from 3 affected titi monkeys were remarkably conserved, sharing 100% identity across the full-length hexon gene (data not shown).

Figure 8:
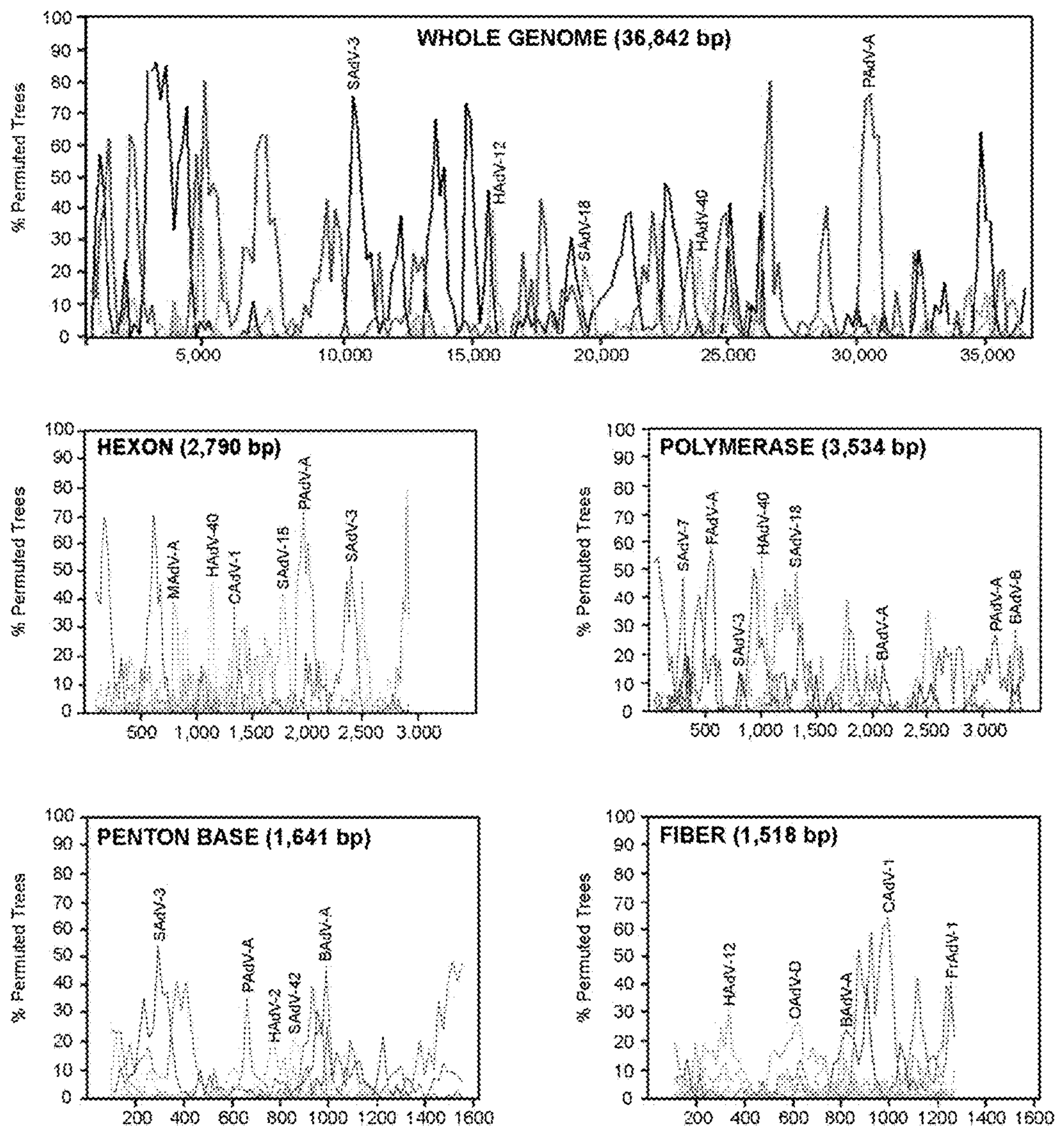
FIG. 8 demonstrates bootscanning recombination analysis of TMAdV. Bootscanning analysis was initially performed with all 95 unique, fully-sequenced adenovirus genomes in GenBank (data not shown), then, after removal of similar viral genomes, with a selected subset representing human/simian adenoviruses in species A-G and all non-primate vertebrate adenoviruses (whole genome, hexon, polymerase, penton base, and fiber). The window size is 400 bp with a step size of 40 bp for the whole genome and 200 bp with a step size of 20 bp for the individual genes. The x-axis refers to the nucleotide position. Please refer to FIG. 3 for definition of abbreviations.

The high level of sequence divergence in TMAdV held true at the amino acid level as well, with amino acid identities relative to other mastadenoviruses ranging from 20.8% to 27.5% for the fiber, the most divergent protein, to 68.7%-78.2% for the hexon (Table 2). Although bearing low sequence similarity to other adenoviruses, the penton base of TMAdV contained an RGD motif that presumably binds $\alpha_v$ integrins. By both nucleotide and amino acid comparisons, the closest phylogenetic relative to TMAdV in GenBank overall was SAdV-3 (FIG. 4; Table 2). Bootscanning analysis revealed no evidence for recombination of TMAdV with other adenoviruses at either the whole-genome or individual gene level (FIG. 8).

dilution. To perform the virus neutralization assay, A549 cells were plated in a 96-well format and allowed to grow to 80-90% confluency. 55 μL of viral supernatant at a concentration of 100 $TCID_{50}$ and 55 μL of serum (starting at a 1:8 dilution) were mixed and incubated for one hour at 37° C. As a control for each serum sample, 55 μL of culture media and 55 μL of serum were mixed and treated in an identical fashion. After incubation, 100 μL of mixture were inoculated into appropriate wells and the entire plate was placed in a 37° C. 5% $CO_2$ incubator. Cells in the plate wells were observed for evidence of CPE every other day for 1 week. For wells that showed inhibition of viral CPE, the corresponding serum samples were diluted in 6 two-fold steps and then retested. The highest dilution that completely inhibited viral CPE was taken as the neutralizing antibody titer.

TABLE 2

Amino acid divergence of TMAdV from other adenoviruses. For each protein, the entry corresponding to the adenovirus with the highest percentage identity relative to TMAdV is highlighted in boldface underline.

| | fiber (IV) | E1A | DBP | polymerase | penton base (III) | pTP | hexon (II) |
|---|---|---|---|---|---|---|---|
| hAd12 (Group A) | 26.4% | 31.0% | 38.0% | 58.3% | 64.3% | 67.5% | 76.4% |
| hAd3 (Group B) | 22.3% | 31.4% | 36.5% | 59.9% | 65.8% | 68.6% | 73.9% |
| sAd21 (Group B) | 22.2% | 30.6% | 36.0% | 60.5% | 66.1% | 68.6% | 72.4% |
| hAd2 (Group C) | 25.0% | 29.4% | 39.5% | 60.5% | 67.0% | 67.8% | 71.6% |
| sAd42 (Group C) | 26.4% | 30.5% | 38.8% | 60.0% | 66.5% | 68.0% | 72.6% |
| hAd9 (Group D) | 21.9% | 28.4% | 38.3% | 61.2% | 66.1% | 68.3% | 74.2% |
| hAd4 (Group E) | 26.3% | 32.6% | 37.1% | 61.6% | 67.9% | 69.7% | 72.9% |
| sAd22 (Group E) | <u>**27.5%**</u> | 31.2% | 36.6% | 61.4% | 67.6% | 70.3% | 74.4% |
| hAd40 (Group F) | 26.9% | 31.0% | <u>**40.1%**</u> | 59.8% | 64.1% | 65.8% | 77.3% |
| sAd7 (Group F) | 25.5% | <u>**32.6%**</u> | 35.7% | 61.3% | 67.0% | 67.9% | 76.7% |
| hAd52 (Group G) | 24.1% | 30.3% | 35.6% | 61.5% | 67.8% | 67.7% | 77.2% |
| sAd3 (rhesus) | 26.6% | 29.9% | 36.8% | 59.4% | <u>**68.2%**</u> | <u>**70.5%**</u> | <u>**78.2%**</u> |
| sAd18 (vervet) | 26.0% | 30.7% | 39.0% | <u>**69.9%**</u> | 66.5% | 67.7% | 76.9% |
| hAd49 (Group D) | 22.1% | 29.2% | 38.3% | 62.9% | 65.6% | 67.6% | 74.8% |
| porcine AdA | 26.4% | 23.6% | 37.4% | 54.4% | 61.7% | 57.6% | 68.7% |
| fowl AdA | 1.6% | N/A* | 25.6% | 36.5% | 41.6% | 31.7% | 48.1% |

Culturing of TMAdV in Human and Monkey Cell Lines

Figure 5:
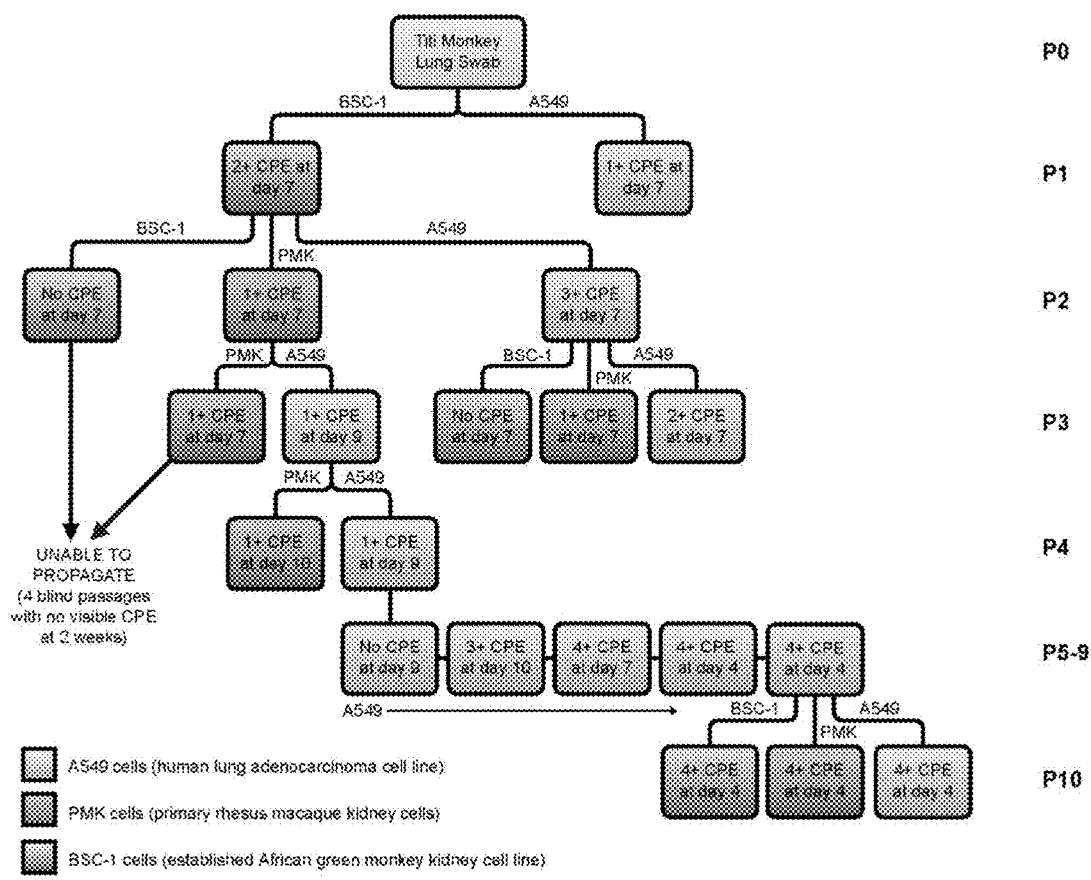
FIG. 5 demonstrates growth and propagation of TMAdV in cell culture. The flow chart displays up to 10 passages (P1-P10) of TMAdV in cell culture in human lung adenocarcinoma (A549, orange), primary rhesus macaque kidney (PMK, brown), or established African green monkey kidney (BSC-1, green) cells.

After identification and characterization of TMAdV, an attempt to culture the virus was undertaken in 2 monkey kidney cell lines (rhesus macaque BSC-1 and African green monkey PMK cells) and 1 human cell line (A549 lung adenocarcinoma cells) (FIG. 5). Direct inoculation of cell cultures with a lung swab from an affected titi monkey produced a weak initial cytopathic effect in macaque BSC-1 and human A549 cells at day 7. However, despite multiple serial passages, propagation of the infected cell culture supernatant in either BSC-1 or PMK cells was unsuccessful. In contrast, propagation in human A549 cells resulted in viral adaptation by passage 6 and generation of a fully adapted strain of TMAdV by passage 10 that was able to productively infect all three cell lines. Thus, culturing and propagation of TMAdV were successful in a human A549 cell line, but not in established or primary monkey kidney cell lines.

Example 2: Seroprevalence of TMAdV in Monkeys and Humans

Materials and Methods

Virus Neutralization Assay

A virus stock of TMAdV (passage 10) was produced on human A549 cells, aliquoted, and quantitated by end-point Results Nineteen serum samples from 16 at-risk, affected titi monkeys were tested. Among 4 affected titi monkeys who survived the outbreak, 2 monkeys mounted a vigorous neutralizing Ab response to TMAdV, with negative pre-outbreak Ab titers (<1:8) but convalescent antibody titers of >1:512, while one monkey exhibited a positive but much weaker response. Affected titi monkeys who died during the outbreak exhibited a wide range of neutralizing Ab titers, from <1:8 to >1:512 (those without Ab likely died before mounting a response). To investigate the possibility of colonization or subclinical infection by TMAdV, serum samples were examined from at-risk asymptomatic titi monkeys (n=3) and nearby rhesus macaques (n=6). All samples from asymptomatic titi monkeys were negative for neutralizing Abs to TMAdV, whereas 1 of the 6 rhesus macaque samples exhibited a titer of 1:16.

One individual at the CNPRC reported becoming ill during the titi monkey outbreak, the researcher in closest, daily contact with the animals. Symptoms began near the onset of the outbreak, although whether they began prior to or after identification of the index case is unclear. The researcher, with a past medical history of multiple sclerosis, initially developed symptoms of a viral upper respiratory infection (URI), including fever, chills, headache, and sore throat, followed by a dry cough, intermittent shortness of breath, and a "burning sensation in the lungs" (suggestive of pleurisy) that lasted 4-6 weeks. Medical care was not sought, and no antibiotics were taken during the illness.

Contact tracing to identify family members and other individuals in close contact with the scientist was conducted. The brother and sister-in-law of the scientist also developed flu-like symptoms about 1-2 weeks after the researcher initially became sick. Their symptoms—fever, cough and muscle aches without shortness of breath or pleurisy—appeared milder and completely resolved within 2 weeks. Neither individual sought medical care for these symptoms. Notably, neither the brother nor the sister-in-law had ever visited the CNPRC.

To explore a potential link between the outbreak and associated illness in humans, CNPRC personnel and close contacts were tested for evidence of recent or prior infection by TMAdV by virus neutralization (FIG. 6).

Approximately 6 months after the outbreak, serum samples were collected from CNPRC personnel in direct contact with the titi monkeys, as well as from 2 family members of the clinically ill CNPRC researcher. Two samples were found positive for neutralizing Abs to TMAdV: (1) Ab titers for the clinically ill researcher were 1:32, and (2) Ab titers for the brother of the clinically ill researcher were 1:8.

Among 80 random blood donors from Northern California with a history of recent travel outside of the United States, 2 individuals (2/80, 2.5%) had positive Ab titers of 1:16 and 1:8. Sera containing antibodies to adenovirus serotypes 1 through 52 were unable to neutralize TMAdV (data not shown), indicating that the results of our serological survey were not due to nonspecific cross-reactivity from prior exposure to known human adenoviruses.

We claim:

1. A heterologous expression vector comprising a promoter operably linked to a heterologous nucleic acid comprising a nucleotide sequence of at least 100 nucleotides in length that has at least 95% sequence identity over its length to SEQ ID NO:1 or its complement.

2. An isolated host cell comprising the expression vector of claim 1.

* * * * *